United States Patent [19]

Hall et al.

[11] 4,010,286
[45] Mar. 1, 1977

[54] FLAVORING WITH 4-METHYL-1-OXASPIRO[5,5]UNDECANE

[75] Inventors: John B. Hall, Rumson; Denis E. Hruza, Sr., Brick Town, both of N.J.; Edward J. Shuster, Brooklyn, N.Y.; Manfred Hugo Vock, Locust; Joaquin Francisco Vinals, Red Bank, both of N.J.

[73] Assignee: International Flavors & Fragrances Inc., New York, N.Y.

[22] Filed: Nov. 20, 1975

[21] Appl. No.: 633,796

Related U.S. Application Data

[63] Continuation-in-part of Ser. No. 547,057, Feb. 4, 1975, abandoned.

[52] U.S. Cl. .......................... 426/536; 260/345.1; 252/522; 131/17 R
[51] Int. Cl.² ................................. A23L 1/226

[58] Field of Search ............... 260/345.1; 426/536

[56] References Cited

UNITED STATES PATENTS 2,422,648  6/1947  Williams et al. ............... 260/345.1

FOREIGN PATENTS OR APPLICATIONS 6,808,496  12/1969  Netherlands

*Primary Examiner*—Joseph M. Golian
*Attorney, Agent, or Firm*—Arthur L. Liberman; Harold Haidt; Franklin D. Wolffe

[57] ABSTRACT

Methods for preparing foodstuffs, flavoring compositions for foodstuffs, chewing gum and flavoring compositions for chewing gums by including therein 4-methyl-1-oxaspiro[5.5]undecane.

2 Claims, 20 Drawing Figures

FIG. 3 FRACTION 2 FROM EXAMPLE II

FRACTION 17 FROM EXAMPLE IV

FRACTION 10 FROM EXAMPLE VII

FIG.6 FRACTION 13 FROM EXAMPLE IX

FIG.7 FRACTION 13 FROM EXAMPLE IX

I.R. SPECTRUM

EXAMPLE II

EXAMPLE II

EXAMPLE III

FRACTION 7 FROM EXAMPLE IV

FIG.13 FRACTION 3 FROM EXAMPLE IV

FIG.14 FRACTION 3 FROM EXAMPLE IV
IR SPECTRUM

FIG.16 FRACTION 9 FROM EXAMPLE LVI

EXAMPLE LVII

EXAMPLE XVII

FIG.19 EXAMPLE LVIII

EXAMPLE LVIII

FLAVORING WITH 4-METHYL-1-OXASPIRO[5.5] UNDECANE

This Application is a continuation-in-part of U.S. Application for Letters Patent Ser. No. 547,057, filed on Feb. 4, 1975 and now abandoned.

BACKGROUND OF THE INVENTION

The present invention relates to novel methods and compositions using novel spiropyran materials.

There has been considerable work performed relating to substances which can be used to impart (or enhance) flavors to (or in) various consumable materials. These substances are used to diminish natural materials, some of which may be in short supply, and to provide more uniform properties in the finished product. Spicey, dill, basil, valerian oil-like, delicate rose, dried fruit, winey, cherry-like, caraway seed-like, thyme-like, piney, raspberry-like, blackberry-like, camphoraceous, herbaceous, eucalyptol-like, cooling, minty, ionone, tea-like, floral, sweet, fruity, woody, apple-like, petit-grain-like, smokey, leafy, peach, wintergreen-like, damascenone-like and green flavor notes or combinations of these for improving the taste and aroma of artificial raspberry or other berry fruit flavoring compositions or tea flavor or synthetic "menthe oil" compositions are particularly desirable for many uses in consumable articles, e.g., foodstuffs, chewing gums and medicinal products. Green, floral, herbal, eucalyptol-like, sweet, minty, woody, fruity, mushroomy, wintergreen oil-like, cornmint and terpineol-like notes are particularly desirable in perfume compositions. Aromatic, sweet, minty and cooling notes are particularly desirable in tobacco.

Chemical compounds having the pyran ring are known to be useful in flavor and fragrance compositions. Thus, published Japanese application 7 4011-073 (Mar. 14, 1974) Mitshi Toatsu Chemicals Inc. discloses 2,5-diethyltetrahydropyran perfumes having rose-like perfume, and good stability in air, sunlight and humidity. Maltol, having the generic name: 3-hydroxy-2-methyl(1,4-pyran) is disclosed in "Perfume and Flavor Chemicals", Arctander Vol. II, No. 1831, to have "a warm-fruity, caramellic-sweet odor with emphasis on the caraway note in the dry state". Saturated polycyclic ethers are disclosed in Chodroff, et al. U.S. Pat. No. 3,417,107 to have attractive ambergris notes as well as a high degree of persistence. The structures of such polycyclic ethers are as follows:

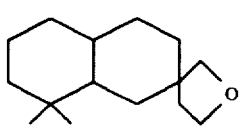 and 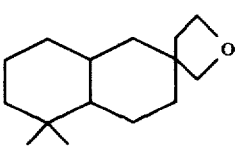

The structures of the compounds in a mix of unsaturated compounds which are precursors of the Chodroff, et al. perfumery compounds are as follows:

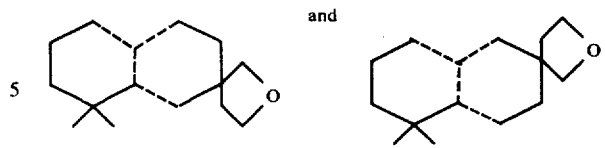

wherein one of the dashed lines represents a carbon-carbon double bond and the other of the dashed lines represents a single carbon.

U.S. Pat. No. 2,422,648 sets forth methods for producing a number of the compounds found to be useful in our invention thus, for example, examples III and IV at columns 6 and 7 of U.S. Pat. NO. 2,422,648 are as follows:

"Example III

A mixture of about 150 parts by weight of 4-methyl-4-pentene-2-ol and about 147.2 parts by weight of cyclohexanone with about 200 parts by weight of benzene and about 2 parts by weight of p-toluenesulfonic acid was refluxed under a column for approximately 4½ hours at about 94° C to about 100° C removing water by azeotropic distillation. Distillation of the neutralized reaction mixture gave about 191.8 parts by weight of material of boiling point 80° to 90° C at 10 mm., from which was obtained the composition corresponding to the formula $C_{12}H_{20}O$ boiling at 87.4° C at 10 mm. which consists substantially of 2,4-dimethyl-6,6-pentamethylene-5,6-dihydro-1,2-pyran.

Example IV

A mixture consisting of about 210 parts by weight of 3,3,5-trimethylcyclohexanone, about 150 parts by weight of 4-methyl-4-pentene-2-ol, about 250 parts by weight of benzene, and about 2 parts by weight of p-toluenesulfonic acid was refluxed under a column at about 91° to 97° C for approximately 10 hours with removal of water by azeotropic distillation. Neutralization and distillation of the reaction mixture gave about 182.3 parts by weight of material having a boiling point of 90° to 96° C at 5 mm. from which was obtained the product having the elemental composition indicated by the formula $C_{15}H_{26}O$ boiling at 94.6° C at 5 mm. and consisting substantially at 2,4-dimethyl-6,6-(2',2',4'-trimethylpentamethylene)-5,6-dihydro-1,2-pyran."

In addition U.S. Pat. No. 2,422,648 at column 5 lines 34–55 states:

"The unsaturated cyclic ethers prepared by the process of the invention are useful as diluents, modifying agents, and processing reagents in the textile industry, and the higher members particularly are valuable as solvents. They may also be used as reagents and/or additives in the formation of synthetic resins, plastics and synthetic rubbers and the higher members may serve as insecticides, fungicides, parasiticides or as constituents of insecticidal, fungicidal and parasiticidal compositions, etc. In addition, they are valuable intermediates in the syntheses of valuable organic products; for example, the substituted dihydropyrans may be hydrogenated, if desired in the presence of a suitable hydrogenation catalyst such as Raney nickel, to produce a novel substituted tetrahydropyran compounds having the formula:

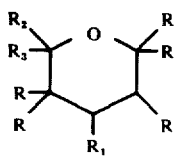

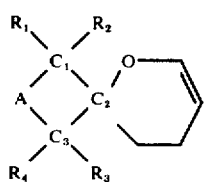

(wherein the R's represent hydrogen or non-olefinic hydrocarbon"

No disclosure of the olfactory properties of such pyran compounds is set forth in U.S. Pat. No. 2,422,648.

Dutch published application No. 6,808,496 published on Dec. 19, 1969 (corresponding to British Pat. No. 1,281,813 published on July 19, 1972) discloses, for use in perfumery in order to provide fruity green scents with an overtone of floral muguet, compounds having the generic structure:

wherein A together with the carbon atoms $C_1$, $C_2$ and $C_3$, forms a cyclic system which may either be monocyclic or polycyclic, e.g. bicyclic or tricyclic, and may carry one or more alkyl groups on the residue A; and $R_1$ to $R_4$ represent hydrogen atoms or alkyl groups having 1 to 5 carbon atoms with the exception that at least one of $R_1$ to $R_4$ represents an alkyl group when A represents a 1,2-ethylidine or 1,3-propylidene group. More specifically, structures 12, 13, 15, 16, 17, 18, 19, 20, 25 and 26 of the published Dutch application No. 6,808,496 are as follows:

12.
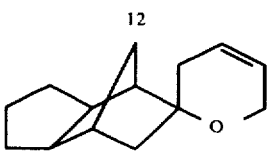

13.
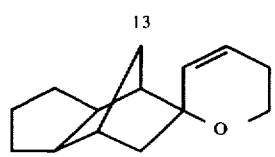

15.
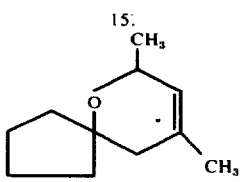

16.
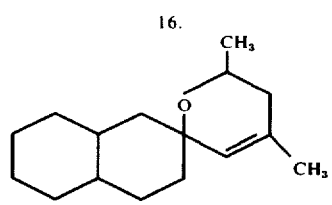

17.
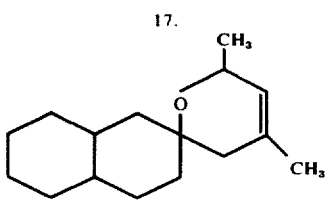

18.
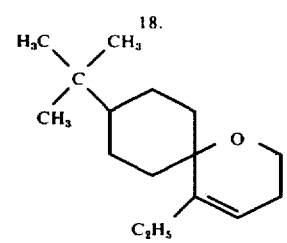

19.
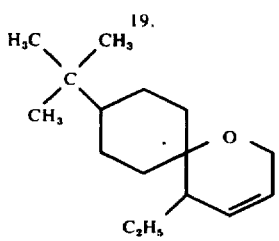

20.
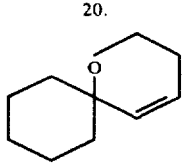

25.
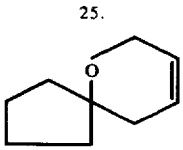

26.
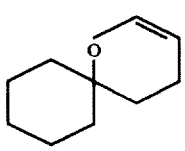

The chemicals defined by these structures are different in kind from the chemical compounds of the instant invention and their fragrance properties are different in kind from those of the instant invention, which are considered to have unexpected, advantageous properties from the standpoint of quality or character of fragrance when used with other perfumery materials and in connection with perfumed articles and colognes.

U.S. Pat. No. 3,901,924, issued on Aug. 26, 1975, discloses certain 1,1-dialkyl naphthopyrans for use in perfumery, having the structure:

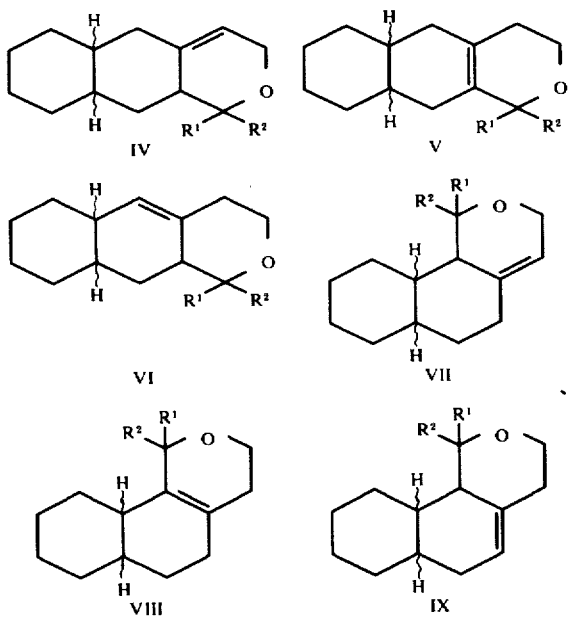

wherein $R_1$ and $R_2$ each represent a lower alkyl group having from one to four carbon atoms, preferably both representing methyl. This patent also discloses chypre and fougere type perfumes in which the naphthopyrans are useful.

The chemicals defined by the structures in U.S. Pat. No. 3,901,924 are different in kind from the chemical compounds of the instant invention from a structural standpoint and from the standpoint of their fragrance properties, the compounds of the instant invention being considered to have unexpected, unobvious and advantageous properties from the standpoint of quality or character or fragrance when used with other perfumes and in connection with perfumed articles and colognes.

THE INVENTION

Figure 1:
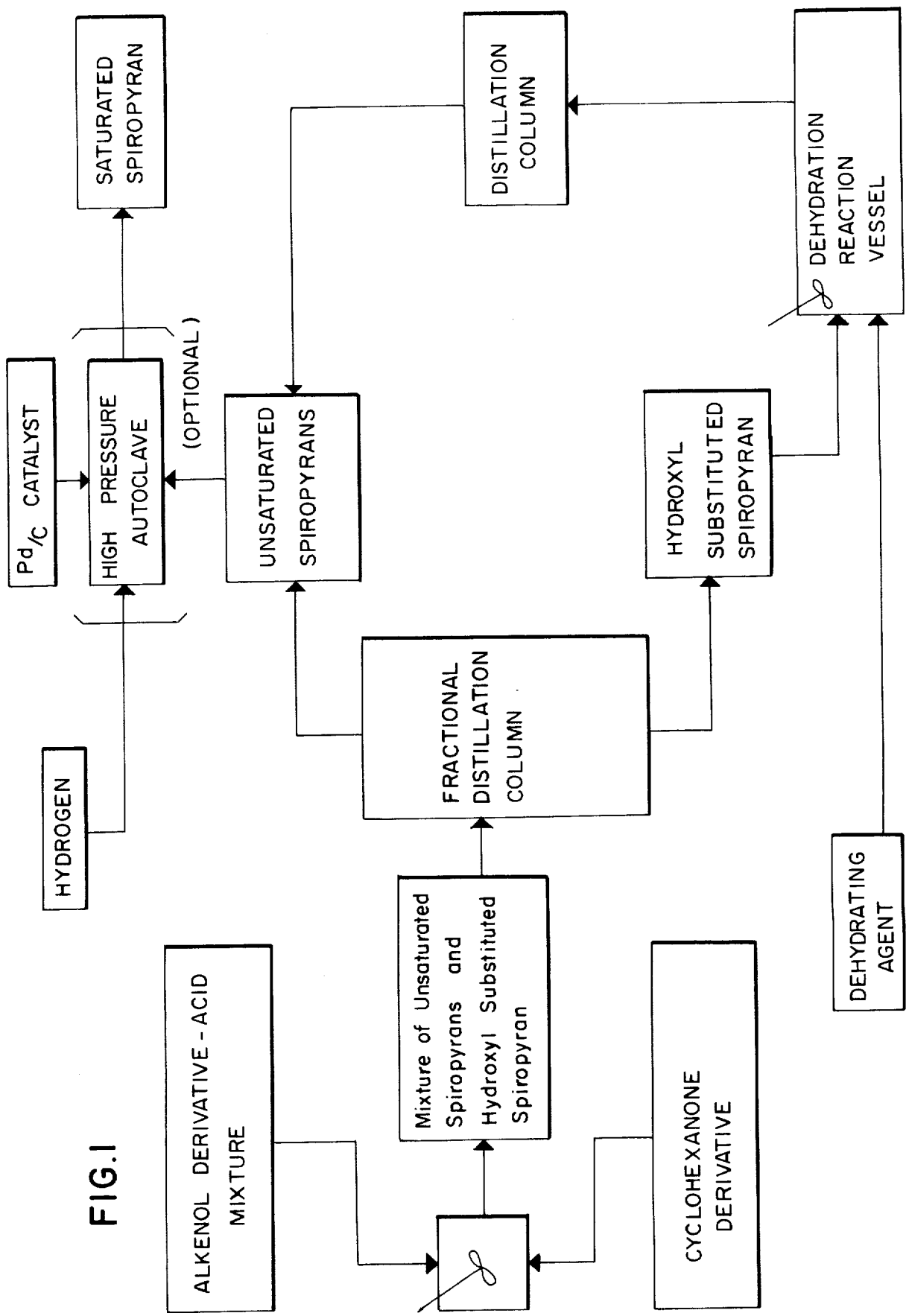
FIG. 1 is a schematic block diagram setting forth the steps of a process to prepare several of the novel spiropyrans of our invention.

It has now been discovered that novel solid and liquid foodstuffs, chewing gum, medicinal products and flavoring compositions for foodstuffs, chewing gums and medical products having spicey, dill, basil, valerain oil-like, delicate rose, dried, fruit, sweet, winey, caraway seed-like, thyme-like, piney, cherry-like, raspberry-like, blackberry-like, camphoraceous, herbaceous, eucalyptol-like, cooling, minty, ionone, tea-like, floral, peach, fruity, woody, apple-like, petitgrain-like, damascenone-like, smokey, leafy, wintergreen-like and green flavor notes for improving the taste and aroma of artificial raspberry or other fruit flavoring compositions or menthe oil or tea flavor compositions; novel perfume aroma imparting compositions and perfumed articles having woody, green, floral, sweet, fruity, herbal, eucalyptol-like, sweet, mushroomy, minty, wintergreen oil-like, cornmint and terpineol-like notes; and novel tobacco flavoring compositions having aromatic, sweet, minty and cooling notes can be created by the utilization of the novel spiropyran materials having the generic structure:

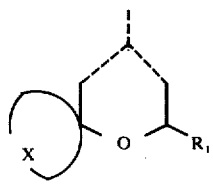

wherein R is hydrogen or methyl and X is a moiety having a structure selected from the group consisting of one of the following structures:

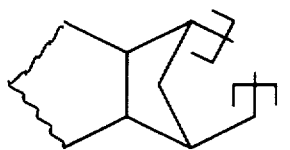
A.

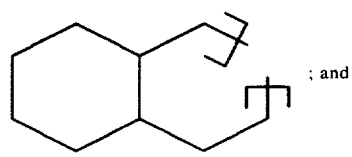
; and
B.

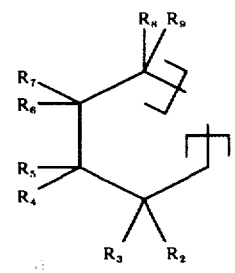
C.

wherein one of the wavy lines is a carbon-carbon single bond or a carbon-carbon double bond and the other of the wavy lines is a carbon-carbon single bond; wherein $R_2$, $R_3$, $R_4$, $R_5$, $R_6$, $R_7$, $R_8$, and $R_9$ represents hydrogen or $C_1$–$C_5$ lower alkyl with the proviso that when any one of $R_2$, $R_3$, $R_4$, $R_5$, $R_6$, $R_7$, $R_8$, and $R_9$ is on of $C_2$—$C_5$ lower alkyl one of $R_2$, $R_3$, $R_4$, $R_5$, $R_6$, $R_7$, $R_8$ and $R_9$ is methyl or hydrogen and each of the other of $R_2$, $R_3$, $R_4$, $R_5$, $R_6$, $R_7$, $R_8$ and $R_9$ is hydrogen; and wherein each of the dashed lines represents a carbon-carbon single bond or a carbon-carbon double bond, with at least two of the dashed lines being carbon-carbon single bonds in flavor and fragrance formulae and/or in foodstuffs, chewing gums, medicinal products, perfumes, tobaccos, soaps, liquid and solid detergent compositions, colognes and cosmetic powders.

The following table sets forth examples of a number of the spiropyrans useful in the practice of our invention, as well as their olfactory properties:

| Spiropyran Material | Structure Representation | Flavor Properties | Fragrance Properties |
| --- | --- | --- | --- |
| Mixture of 4-methylene-1-oxaspiro (5.5)undecane, 4-methyl-1-oxaspiro (5.5)-undec-3-ene and 4-methyl-1-oxaspiro (5.5)undec-4-ene | | Dill, basil, valerian oil, aroma with caraway nuances and dill, basil, valerian oil flavor with thyme, piney, and mouthfeel nuances. | Ready, green, basil, floral, herbal and eucalyptol notes. |
| 4-methyl-1-oxaspiro (5.5)undecane | | Camphoraceous, blackberry and berry aroma with herbaceous nuances and camphoraceous, eucalyptol and piney flavor with basil, berry, cooling minty and herbaceous nuances. | Basil, herbaceous, and eucalyptol notes. |

-continued

| Spiropyran Material | Structure Representation | Flavor Properties | Fragrance Properties |
|---|---|---|---|
| Mixture of 2,4-dimethyl-1-oxaspiro (5.5)undec-3-ene, 2,4-dimethyl-1-oxaspiro (5.5)undec-4-ene and 2-methyl-4-methylene-1-oxaspiro (5.5)undecane | | Ionone, tea, and red-berry aroma with herbaceous "damascenone-like", floral sweet, fruity, woody and apple-like nuances and woody, petitgrain-like fruity flavor with apple, smokey, and astringent nuances. | Green, herbaceous, sweet oily, slightly minty aroma with "pickled", green olive top notes. |
| Mixture of 8,8,10-trimethyl-4-methylene-1-oxaspiro (5.5) undecane, 4,8,8,10-tetra-methyl-1-oxaspiro (5.5) undec-3-ene and 4,8,8,10 tetramethyl-1-oxaspiro(5.5) undec-4-ene | | Green, leafy, minty (parsley-like) aroma with green, minty, herbaceous (parsley-like) flavor. | Green, floral, minty and terpineol-like notes. |
| Mixture of 9-t-butyl-4-methylene-1-oxaspiro (5.5) undecane, 4-methyl-9-t-butyl-1-oxaspiro (5.5)undec-3-ene and 4-methyl-9-t-butyl-1-oxaspiro (5.5)undec-4-ene | | At 1 ppm has a weedy, green, herbaceous aroma and a taste which gives an initial sweet effect changing to an astringent note; and at 5 ppm has a strong weedy, green aroma with vegetable, green, over-ripe green pepper-like notes; and a taste wherein the vegetable character dominates, having sweet artichoke-like undertones. | Green, floral and warm linen notes. |
| Mixture of 7-isopropyl-10-methyl-4-methylene-1-oxaspiro(5.5)undecane, 7-isopropyl-4-10-dimethyl-1-oxaspiro(5.5)undec-3-ene and 7-isopropyl-4-10-dimetyl-1-oxaspiro(5.5)undec-4-ene | | Damascenone-like, rosey, minty aroma with floral, peach and tea nuances and a hay, tea, apple flavor with damascenone-like cooling, spicy and astringent nuances. | Minty, woody, cornmint note with weedy topnote fragrance. |
| 4-10-dimethyl-7-isopropyl-1-oxaspiro(5.5)undecane | | Sweet, delicate rose, dried fruit, winey apple fruit aroma and sweet, apple, delicate rosey, juicy, dried fruit, yeasty and winey flavor. | Low-keyed, sweet, floral, fruity aroma. |
| Reaction product of dihydro verdyl ketone and 3-methyl-3-buten-1-ol | | Green weedy aroma with green weedy and fatty flavor characteristics at a concentration of 0.1 ppm. | Green, floral, woody aroma with fruity and tomato nuances. |
| Reaction product of verdyl ketone and 3-methyl-3-buten-1-ol | | Weedy, green aroma and fatty, green, weedy, flavor at 0.05 ppm. | Green, floral mushroomy, rich fragrance with an underlying borneol note. |
| Reaction product of beta-decalone and 3-methyl-3-buten-1-ol | | Weedy, green aroma character and a weedy, green, fatty, sweet flavor character. | — |

-continued

| Spiropyran Material | Structure Representation | Flavor Properties | Fragrance Properties |
|---|---|---|---|
| a-t-butyl-4-methyl-1-oxa-spiro(5.5)undecane | 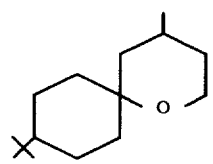 | Green, floral, methylsalicylate aroma and a methyl salicylate-type green, floral flavor with phenolic and astringent notes. | A low-keyed, floral, woody aroma reminiscent of hexenyl salicylate and also has buttery, sulfurous notes. |
| 4,8,8,10-tetramethyl-1-oxaspiro(5.5)undecane | 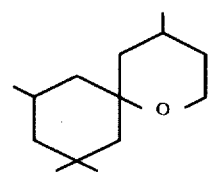 | Sweet, fruity, berry aroma and a sweet, fruity, berry flavor with cherry and green nuances at 5 ppm. | Fruity, strawberry, metallic note with underlying valeric notes and as it dries out it becomes more fruity, floral, sweet and "benzyl salicylate-like". |

The dashed lines in each of the structures representations of Table I represent double bonds. Where two dashed lines are set forth in the same structure, a mixture of double bond isomers is indicated. The wavy lines in the structure representation of Table I also represent possible double bonds. Where two wavy lines are set forth in the same structure, a mixture of double bond isomers is indicated.

For the purposes of our invention, where possible the foregoing structures are intended to cover the "dextro", "laevo" and mixtures of dextro and laevo stereoisomers (where saturated spiropyran derivatives are involved) as well as the "cis", "trans" and mixtures of cis and trans isomers of the spiropyrans useful in practicing our invention.

When the spiropyran derivatives of our invention are used as food flavor adjuvants, the nature of the co-ingredients included with the said spiropyran derivatives in formulating the product composition will also serve to alter the organoleptic characteristics of the ultimate foodstuffs treated therewith.

As used herein in regard to flavor, the term "alter" in its various forms means "supplying or imparting flavor character or note to otherwise bland, relatively tasteless substance or augmenting or enhancing the existing flavor characteristics where a natural flavor is deficient in some regard or supplementing the existing flavor impression to modify its quality, character or taste".

As used herein, the term "enhance" is intended to mean the intensification (without effecting a change in kind of quality of aroma or taste) of one or more taste and/or aroma nuances present in the organoleptic impression of a consumable material, e.g. foodstuff, tobacco, chewing gum, medicinal product, perfume composition or perfumed article.

As used herein, the term "chewing gum" is intended to mean a composition which comprises a substantially water insoluble, chewable plastic gum base such as chicle, or substitutes therefor, including jelutong, guttakay rubber and/or certain comestible natural or synthetic resins or waxes. Incorporated within the gum base, in admixture therewith may be plasticizers or softening agents, e.g. glycerin; and a flavoring composition which incorporates the spiropyran materials of our invention and, in addition, sweetening agents which may be sugars, including sucrose or dextrose and/or artificial sweetners including dipeptides, cyclamates and saccharin. Other optional ingredients may also be present.

The term "medicinal product" includes both solids and liquids which are ingestible, non-toxic materials having medicinal value such as cough syrups, cough drops, toothpaste, aspirin and chewable medicinal tablets as further exemplified herein.

As used herein the term "foodstuff" includes both solid and liquid ingestible materials which usually do, but need not have nutritional value. Thus, foodstuffs include meats, gravies, soups, convenience foods, beverages, dairy products, candies, vegetable, cereals, soft drinks, snacks, chewing gum, chewable vitamin tablets and the like.

Substances suitable for use herein as co-ingredients or flavoring adjuvants are well known in the art for such use being extensively described in the relevant literature. Such material is required to be "ingestibly" acceptable and thus non-toxic or otherwise non-deleterious. Particularly critical is the additional requirement that such material be organoleptically compatible with the spiropyran materials of our invention individually or in admixture. Also critical is the additional requirement that such material be nonreactive (within the range of storage conditions and room temperature use conditions) with spiropyran materials of our invention.

Accordingly, such materials which may in general be characterized as flavoring adjuvants or vehicles comprising broadly stabilizers, thickeners, surface active agents, conditioners, other flavorants and flavor intensifiers.

Stabilizer compounds include preservatives, e.g., sodium chloride, antioxidants, e.g., calcium and sodium ascorbate, ascorbic acid, butylate hydroxyanisole (mixture of 2- and 3-tertiary-butyl-4-hydroxyanisole), butylate hydroxy toluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agaragar; carrageenan; cellulose; and cellulose derivatives such as carboxymethyl cellulose and methyl cellulose; natural and synthetic gums such as gum arabic, gum tragacanth; gelatin, proteinaceous materials, lipids; carbohydrates; starches pectins, and emulsifiers, e.g., mono-and diglycerides of fatty acids, skim milk powder, hexoses, pentoses, disaccharides, e.g., sucrose, corn syrup solids and the like.

Surface active agents include emulsifying agents, e.g., fatty acids such as capric acid, caprylic acid, palmitic acid, myristic acid and the like, mono-and diglycerides of fatty acids, lecithin, defoaming and flavor-dispersing agents such as sorbitan monosterate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, turmeric and curcumin and the like; firming agents such as aluminum sodium sulfate, calcium chloride and calcium gluconate; texturizers; anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources, such as zinc chloride, zinc sulfate and the like.

Other flavorants and flavor intensifiers include organic acid, e.g., fatty saturated acids, unsaturated acids and amino acids; alcohols, e.g., primary and secondary alcohols, esters; carbonyl compounds, e.g., aldehydes and ketones as well as lactones; cyclic organic materials including benzene derivatives, isocyclics, heterocyclics such as furans particularly 2,5-dimethyl-3-acetyl furan and 2-methyl-2,3-dihydro furan-3-one, pyridines, pyrazines (particularly monoalkyl, dialkyl, trialkyl and tetraalkyl substituted pyrazines) and the like, sulfur-containing materials including thiazoles, disulfides, thiols, sulfides, aldehydes (for example, 3-phenyl-4-pentenal, 3-phenyl-3-pentenal, 3-phenyl-2-pentenal, 2-phenyl-2-pentenal and 2-phenyl-3-methyl-2-butenal); tri-sulfides and the like; other flavor potentiators such as monosodium glutamate, guanylates, inosinates, natural and synthetic flavorants such as vanillin, ethyl vanillin, diacetyl, phenethyl-2-furoate, maltol, natural gums and the like; spices, herbs, essential oils and extractives including "bitterness principles" such as theobromine, caffeine, naringin and other suitable materials creating a bitter effect.

The specific flavoring adjuvant selected for use may be either solid or liquid depending upon the desired physical form of the ultimate product, i.e., foodstuff, whether simulated or natural, and should, in any event, be capable of providing an environment in which the spiropyran material can be dispersed or admixed to provide a homogeneous medium. In addition, selection of one or more flavoring adjuvants as well as the quantities thereof will depend upon the precise organoleptic character desired in the finished product. Thus, in the case of flavoring compositions, ingredient selection will vary in accordance with the foodstuff to which the flavor and aroma are to be imparted. In contradistinction, in the preparation of solid products, e.g., simulated foodstuffs, ingredients capable of providing normally solid compositions should be selected such as various cellulose derivatives.

As will be appreciated by those skilled in the art, the amount of spiropyran material employed in a particular instance can vary over a relatively wide range whereby to its desired organoleptic effects. All parts and percentages given herein are by weight unless otherwise specified. Thus, correspondingly, greater amounts would be necessary in those instances wherein the ultimate food composition to be flavored is relatively bland to the taste, whereas relatively minor quantities may suffice for purposes of enhancing the composition merely deficient in natural flavor or aroma. Thus, the primary requirement is that the amount selected to be effective, i.e., sufficient to alter the organoleptic characteristics of the parent composition, whether foodstuff per se or flavoring composition. Thus, the use of insufficient quantities of spiropyran material will, of course, substantially vitiate any possibility of obtaining the desired results while excess quantities prove needlessly costly and in extreme cases, may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions it has been found that quantities of spiropyran material ranging from a small but effective amount, e.g., 0.5 parts per million up to about 0.1% (1000 parts per million) by weight based on total composition are suitable. Concentrations in excess of the maximum quantity stated are not normally recommended since they fail to provide commensurate enhancement of organoleptic properties. In those cases, wherein the spiropyran material is added to the foodstuff as an integral component of the flavoring composition, it is, of course, essential that the total quantity of flavoring composition employed be sufficient to yield an effective spiropyran material concentration in the foodstuff product.

Food flavoring compositions prepared in accordance with the present invention preferably contain the spiropyran material in concentrations ranging from about 0.001% up to about 10% by weight based on a total weight of said flavoring composition.

The compositions described herein can be prepared according to conventional techniques well known as typified by cake batters and fruit juices and vegetable juices and an be formulated by merely admixing the involved ingredients within the proportions stated in a suitable blender to obtain the desired consistency, homogeneity of dispersion, etc. Alternatively, flavoring compositions in the form of particulate solids can be conveniently prepared by admixing the spiropyran material with for example gum arabic, gum tragacanth, carrageenan and the like and thereafter spray-during the resultant mixture whereby to obtain the particular solid product. Pre-prepared flavor mixes in powder form, e.g., a red currant mix or a berry fruit (e.g., red raspberry) flavored powder obtained by mixing dried solid components, e.g., starch, sugar, and the like and one or more of the spiropyran materials of our invention in a dry blender until the requisite degree of uniformity is achieved.

It is presently preferred to combine one or more of spiropyran materials of our invention with the following adjuvants:

Organic acids, e.g., acetic acid, butyric acid, caproic acid, caprylic acid, formic acid, 2-hexenoic acid, 3-hexenoic acid, isobutyric acid, isovaleric acid, propionic acid and valeric acid; ketones and aldehydes, e.g., acetaldehyde, acetone, acetyl methyl carbinol, acrolein, diacetyl, beta, beta-dimethylacrolein, hexanal, 2-hexenal, cis-3-hexenal, 4(p-hydroxyphenyl)-2-butanone, alpha-ionone, beta-ionone, and 2-pentenal; alcohols, such as 1-butanol, trans-2-buten-1-ol, ethanol, geraniol, 1-hexanol, cis-3-hexen-1-ol, 3-methyl-3-buten-1-ol, 1-pentanol, 1-penten-3-ol and 2-(4-hydroxy-4-methyl pentyl) norbornadiene; esters, such as butyl acetate, ethyl acetate, ethyl butyrate, ethyl crotonate, ethyl propionate, 2-hexenyl acetate, 2-hexenyl butyrate, hexyl acetate, hexyl butyrate, isoamyl acetate, isopropyl butyrate, methyl butyrate, methyl caproate, methyl caprylate, propyl acetate, amyl acetate, amyl butyrate, benzyl salicylate, dimethyl anthranilate, ethyl methylphenylglycidate, ethyl succinate, isobutyl cinnamate and terpenyl acetate, essential oils such as jasmine absolute, rose absolute, orris absolute, lemon essential oil and vanilla; lactones, sulfides, e.g., methyl sulfide and other materials such as maltol and citral, as well as natural raspberry oil.

One or more spiropyran materials of our invention and an auxiliary perfume ingredient, for example, alcohols, aldehydes, nitriles, esters, cyclic esters, and natural essential oils may be admixed so that the combined odors of the individual components produce a pleasant or desired fragrance. Such perfume compositions usually contain (a) the main note or the "bouquet" or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual component will contribute its particular olfactory characteristics but the over-all effect of the perfume composition will be the sum of the effects of each of the ingredients. Thus, one or more of the spiropyran materials of our invention can be used to alter the aroma characteristics of a perfume composition, for example, by utilizing or moderating the olfactory reaction contributed by another ingredient in the composition.

The amount of the spiropyran material of our invention which will be effective in perfume compositions depend on many factors including the other ingredients, their amounts and the effects which are desired. It has been found that perfume compositions containing as little as 0.05% of one or more of the spiropyran materials of our invention or even less can be used to impart a green, floral, and herbaceous aroma found in hyacinth; or a green, minty aroma essential to geranium bourbon or a green, herbal aroma essential to basil, to soaps, cosmetics, and other products. The amount employed can range from 1% up to 100% of the fragrance components and will depend on considerations of cost, nature of the end product, the effect desired in the finished product and the particular fragrance sought.

The spiropyran materials of our invention are useful in perfume compositions as olfactory components in detergents, and soaps; space odorants and deodorants; perfumes; colognes; toilet water; bath preparations such as bath oils and bath solids; hair preparations such as lacquers, brilliantines, pomades and shampoo; cosmetic preparations such as creams, deodorants, hand lotions and sunscreens; powders such as talcs, dusting powders, face powders and the like. When used as an olfactory component of a perfumed article, as little as 100 parts per million of one of more of the spiropyran materials of our invention will suffice to impart spicey, green, basil, damascenone-like, floral, herbal, eucalyptol-like, berry, sweet oily and minty aromas thereto. Generally, no more than 3.0% of one or more of the spiropyran materials of our invention based on the ultimate end product is required in the perfume composition.

In addition, the perfume composition or fragrance composition of this invention contain a vehicle or carrier for the spiropyran material. The vehicle can be a liquid such as an alcohol, a non-toxic alcohol, a non-toxic glycol or the like. The carrier can also be an absorbent solid such as a gum (e.g., gum arabic) or components for encapsulating the composition (such as gelatine).

It will thus be apparent that one or more of the spiropyran materials of our invention can be utilized to alter the sensory properties, particularly organoleptic properties such as flavor and/or fragrances of a wide variety of consumable materials.

An additional aspect of our invention provides an organoleptically improved smoking tabacco product and additives therefor as well as methods of making the same which overcome specific problems heretofore encountered in which specific desired aromatic, sweet, minty and "cooling" flavor characteristics are created or enhanced and may be readily controlled and maintained at the desired uniform level regardless of variations in the tobacco components of the blend; or the nature of the filter used in conjunction with the tobacco article.

This invention further provides improved tobacco additives and additives for materials used in the fabrication of tobacco articles and methods whereby desirable sweet, aromatic, minty and cooling flavor characteristics may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of the spiropyran materials of our invention.

In addition to the spiropyran materials of our invention, other flavoring and aroma additives may be added to the smoking tabacco material or substitute therefor either separately or in mixture with one or more of the spiropyran materials:

I. Synthetic Materials
Beta-methyl-cinnamaldehyde;
Eugenol;
Dipentene;
Damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1-1;
2-methyl-5-isopropyl-1,3-nonadiene-8-one;
2-Methyl-5-isopropyl acetophenone;
2-Hydroxy-2,5,5,8a-tetramethyl-1-(2-hydroxyethyl)-decahydronaphthalene;

Dodecahydro-3a-6,6,9a-tetramethyl naphtho-(2,1-b)-furan;
4-Hydroxy hexanoic acid, gamma lactone;
Polyisoprenoid hydrocarbons defined in Example V of U.S. Pat. No. 3,589,372 issued on June 29, 1971.

II. Natural Oils
Celery seed oil;
Coffee extract;
Bergamot oil;
Cocoa extract;
Nutmeg oil;
Origanum oil An aroma and flavoring concentrate containing one or more of the spiropyran materials of our invention and, if desired, one or more of the above indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tabacco substitutes (e.g., lettuce leaves) or mixtures thereof. The proportions of flavoring additives may be varied in accordance with taste but insofar as enhancement or the imparting of sweet, minty, aromatic and cooling notes, we have found that satisfactory results are obtained if the proportion by weight of the sum total of spiropyran material to smoking tobacco material is between 50 ppm and 500 ppm (0.005%–0.05%) of the active ingredients to the smoking tobacco material. We have further found that satisfactory results are obtained if the proportion by weight of the sum total of spiropyran material used to flavoring material is between 0.05 and 0.50.

Any convenient method for incorporating the spiropyran material in the tobacco product may be employed. Thus, the spiropyran material taken alone or along with other flavoring additives may be dissolved in a suitable solvent such as ethanol, pentane, diethyl ether and/or other volatile organic solvents and the resulting solution may either be spread on the cured, cased and blended tobacco material or the tobacco material or filter may be dipped into such solution. Under certain circumstances, a solution of spiropyran material taken alone or taken further together with other flavoring additives as set forth above, may be applied by means of a suitable applicator such as a brush or roller on the paper or leaf wrapper for the smoking product, or it may be applied to the filter by either spraying, or dipping or coating.

Furthermore, it will be apparent that only a portion of the tobacco or substitute therefor need be treated and the thus treated tobacco may be blended with other tobaccos before the ultimate tobacco product is formed. In such cases, the tobacco treated may have one or more spiropyran materials of our invention in excess of the amounts or concentrations above indicated so that when blended with other tobaccos, the final product will have the percentage within the indicated range.

In accordance with one specific example of our invention, an aged, cured and shredded domestic burley tobacco is spread with a 20% ethyl alcohol solution of 2,4-dimethyl-1-oxaspiro(5.5)undec-3-ene in an amount to provide a tobacco composition containing 800 ppm by weight of 2,4-dimethyl-1-oxaspiro (5.5)undec-3-ene on a dry basis. Thereafter, the alcohol is removed by evaporation and the tobacco is manufactured into cigarettes by the usual techniques. The cigarette when treated as indicated has a desired and pleasing aromatic, minty and cooling aroma which is detectable in the main and side streams when the cigarette is smoked.

While our invention is particularly useful in the manufacture of smoking tobacco, such as cigarette tobacco, cigar tobacco, and pipe tobacco, other tobacco products formed from sheeted tobacco dust or fines may also be used. As stated supra, the spiropyran materials of our invention can be incorporated with materials such as filter tip materials, seam paste, packaging materials and the like which are used along with the tobacco to form a product adapted for smoking. Furthermore, the spiropyran materials of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

The following examples are given to illustrate embodiments of the invention as it is presently preferred to practice it. It will be understood that these examples are illustrative, and the invention is not to be considered as restricted thereto except as indicated in the appended claims. All parts and percentages are by weight unless otherwise indicated.

EXAMPLE I

Preparation of Mixture of
4-Methylene-1-Oxaspiro(5.5) Undecane,
4-Methyl-1-Oxaspiro(5.5) Undec-3-ene,
4-Methyl-1-Oxaspiro(5.5) Undec-4-ene and
4-Hydroxy-4-Methyl-1-Oxaspiro(5.5) Undecane Reaction:

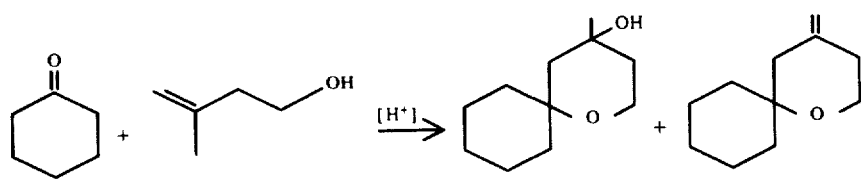

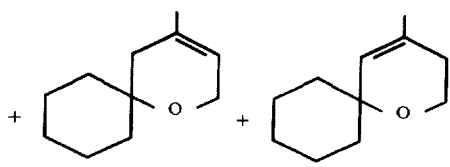

Into a 500 ml reaction flask equipped with stirrer, thermometer, reflux condenser and addition funnel is place 98 gms. (1 mole) of cyclohexanone which is then heated to 80° C and maintained at that temperature. In a separate reaction vessel is placed 86 gms. (1 mole) of 3-methyl-3-buten-1-ol and 1 gm. of concentrated sulfuric acid is added thereto dropwise while maintaining the temperature of 10° C. The resulting mixture of sulfuric acid and 3-methyl-3-buten-1-ol is then added over a period of 45 minutes to the cyclohexanone while maintaining the reaction mass temperature in the range of 80°–85° C.

After the addition, the reaction mass is stirred maintaining its temperature at 80°–85° C for a period of 6 hours.

The reaction mass is then cooled to room temperature and is washed with a 100 ml portion of 10% aqueous sodium hydroxide. The aqueous phase is then extracted with one 50 ml portion of cyclohexane. The reaction mass is then combined with the cyclohexane extract and the resultant material is washed with one 100 ml portion of 10% sodium chloride solution.

The crude reaction product is stripped and rushed over after adding thereto 10 gms. of Primol (See Note 1) and 0.1 gms. of Ionol (See Note 2) at a vapor temperature of 57°–136° C, a liquid temperature of 105°–200° C and a vacuum of 15.0 – 0.75 mm Hg.

The rushed over material is then fractionated after adding thereto 4.5 gms. of Primol, 0.1 gms. of Ionol and 0.5 gms. of triethanolamine as follows:

| Fraction No. | Vapor Temp. | Liquid Temp. | Pressure (mm Hg) | Weight of Fraction | Reflux Ratio |
|---|---|---|---|---|---|
| 1 | 49–55° C | 119–123° C | 15 | 4.7 | 20:1 |
| 2 | 105 | 125 | 15 | 6.9 | 20:1 |
| 3 | 105 | 128 | 15 | 6.2 | 20:1 |
| 4 | 106 | 137 | 15 | 14.7 | 20:1 |
| 5 | 107 | 144 | 15 | 8.5 | 20:1 |
| 6 | 113 | 147 | 15 | 7.1 | 20:1 |
| 7 | 122 | 134 | 8.7 | 9.0 | 20:1 |
| 8 | 122 | 136 | 8.6 | 10.1 | 9:1 |
| 9 | 122 | 139 | 8.1 | 7.6 | 9:1 |
| 10 | 122 | 142 | 8.0 | 8.1 | 9:1 |
| 11 | 122 | 148 | 8.0 | 6.3 | 9:1 |
| 12 | 127 | 156 | 8.0 | 5.6 | 9:1 |
| 13 | 126 | 168 | 8.0 | 8.1 | 9:1 |
| 14 | 140 | 175 | 8.0 | 7.9 | 9:1 |
| 15 | 145 | 200 | 8.0 | 4.7 | 9:1 |

Fractions 3–6, when bulked, consist essentially of compounds having the structures:

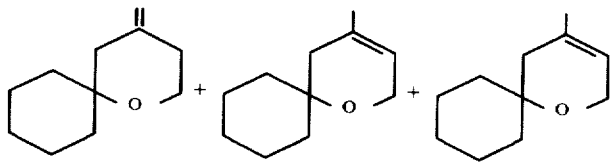

as confirmed by capillary GLC (conditions: SF-96 capillary column; 500 feet × 0.03 inch; programmed 80°–185° C at 2°C/minute), NMR, mass spectral and infra-red analyses.

Figure 2:
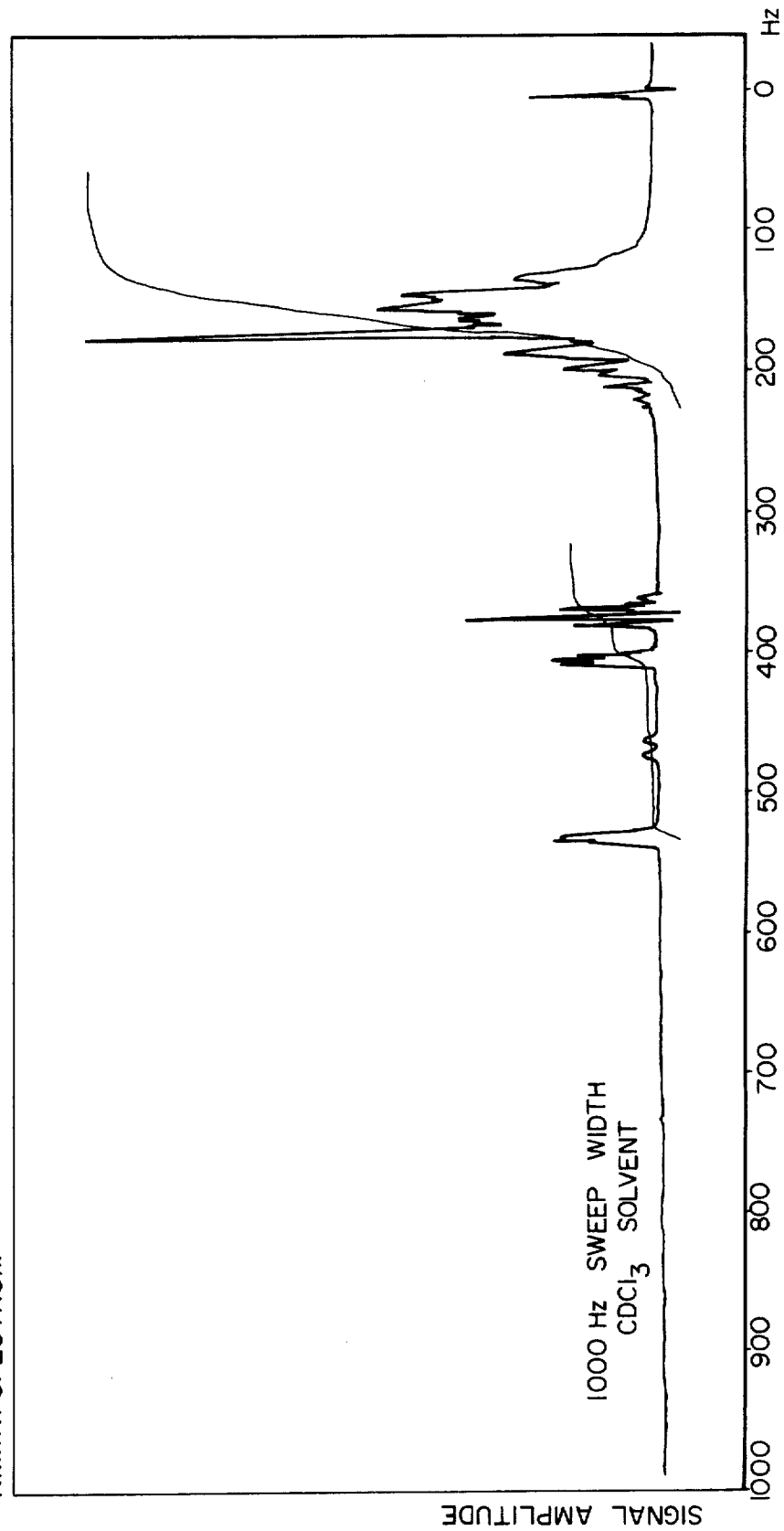
FIG. 2 represents the nuclear magnetic resonance spectrum for Fractions 3–6 resulting from the fractional distillation carried out on a product produced according to Example I, a mixture of 4-methylene-1-oxaspiro[5.5]undecane, 4-methyl-1-oxaspiro[5.5]undec-3-ene, 4-methyl-1-oxaspiro[5.5]undec-4-ene.

The NMR spectrum for fractions 3–6 is set forth in FIG. 2.

Mass Spectral Data: Molecular ion, then, in decreasing order of intensity: m/e = 166/123, 166, 68, 55, 41.

Infra-red Data: 755, 780, 810, 820, 840, 870, 875, 900, 960, 985, 1000, 1010, 1070, 1085, 1105, 1145, 1160, 1175, 1210, 1255, 1270, 1280, 1355, 1375, 1440, 1460, 2820, 2850, 2920, 3000.

| Nuclear Magnetic Resonance Data | Interpretation |
|---|---|
| 1.67 (s) | $=C-CH_3-$ |
| 2.20–1.30 (m) | $-CH_2-$ |
| 3.74 (diffuse t) | $-CH_2-O-$ |
| 4.06 (m) | $=C-CH_2-O$ |
| 4.70 (d) | $\begin{array}{c}H\\ \diagdown \phantom{=} \diagup \\ -C=C \\ \phantom{==} \diagdown \\ \phantom{====} H\end{array}$ |
| 5.26 (m) | Olefinic proton |

Fractions 8–12 consists essentially of the compound having the structure:

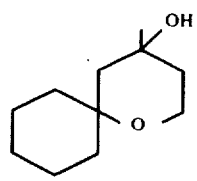

Note 1: Primol is a registered trademark identifying a hydrocarbon mineral oil produced by Exxon Incorporation of Linden, New Jersey.

Note 2: Ionol is a registered trademark identifying the compound 2,6-di-t-butyl-4-methyl phenol.

EXAMPLE II

Preparation of 4-Methyl-1-Oxaspiro(5.5) Undecane

Reaction:

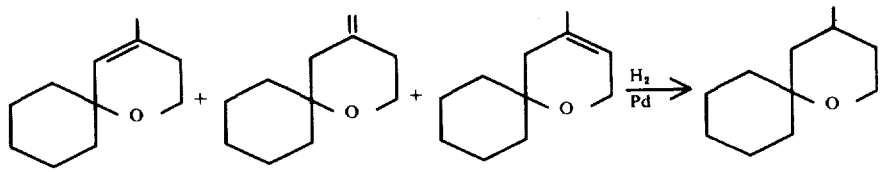

Into a 300 ml autoclave equipped with a heating coil and stirrer, the following materials are added:

| Isopropyl alcohol | 120 gms. |
|---|---|
| 5% Palladium on carbon catalyst | 0.8 gms. |
| Mixture of 4-methylene-1-oxaspiro[5.5]undecane,4-methyl-1-oxaspiro[5.5]undec-3-ene and 4-methyl-1-oxaspiro[5.5]undec-4-ene produced according to Example 1 (Fractions 3-6) | 166 gms. |

The autoclave is then pressurized with hydrogen gas over a period of 11 hours and operated at 20°–30° C, periodically repressurizing the autoclave to 50 psig. After 11 hours, 1 mole of hydrogen is absorbed.

The contents of the autoclave is then filtered, the solvent stripped off and the material is then distilled through a 2 inch splash column after adding thereto 5 gms. of Primol, at a vapor temperature of 69°–71° C and a pressure of 3.3 – 3.7 mm Hg.

This material consists essentially of a compound having the structure:

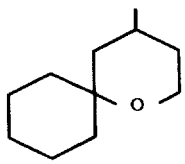

as confirmed by infra-red, mass spectral and NMR analyses.

Figure 3:
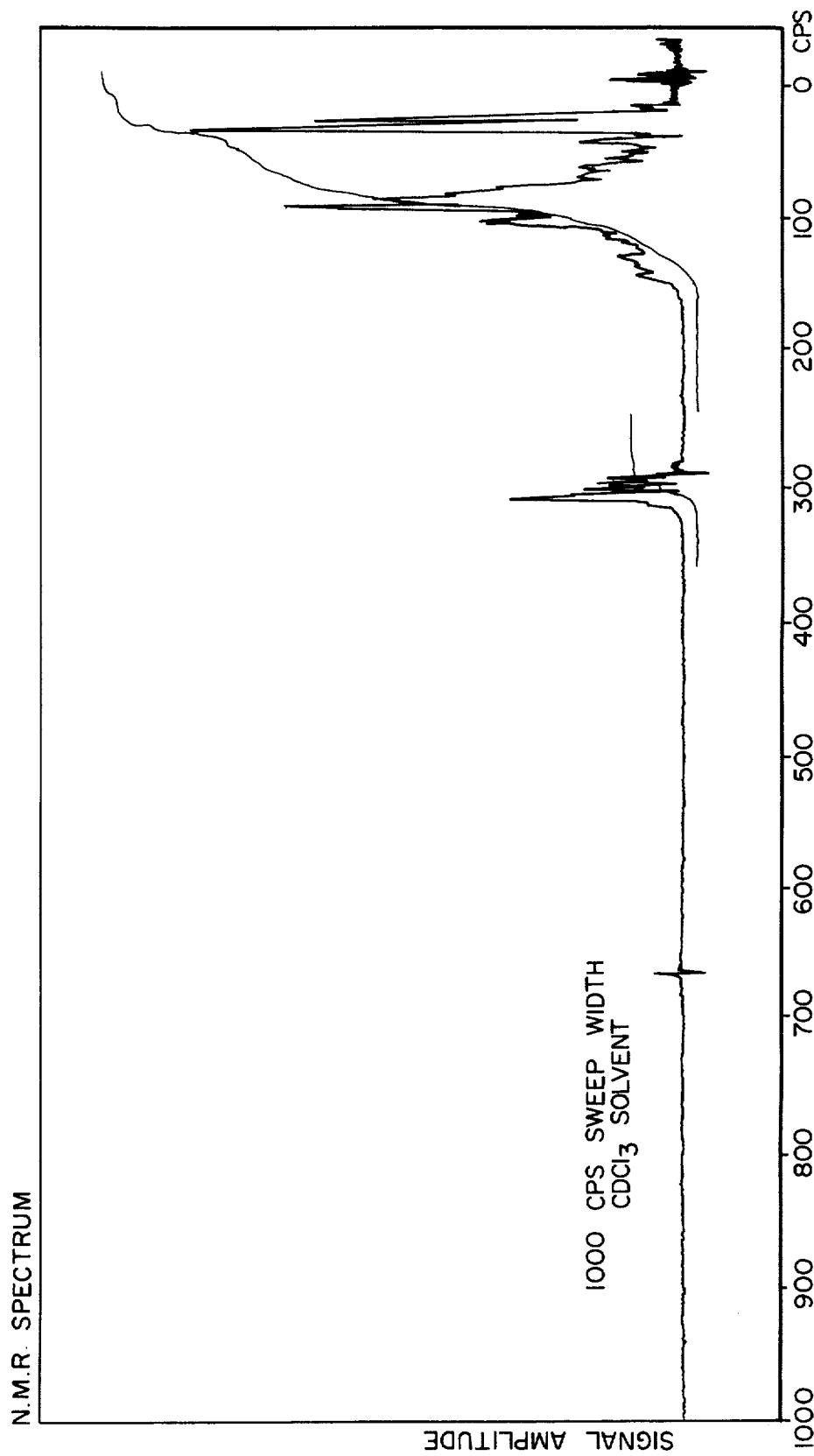
FIG. 3 represents the nuclear magnetic resonance spectrum for Fraction 2 resulting from the distillation of 4-methyl-1-oxaspiro[5.5]undecane produced according to Example II.

The NMR Spectrum for Fraction 2 is set forth in FIG. 3.

Mass Spectral Data: Molecular ion, then, in order of decreasing intensity: m/e = 168/125, 55, 112, 41, 27, 39.

Infra-red Data: 500, 720, 820, 840, 880, 900, 970, 975, 980, 1045, 1060, 1080, 1100, 1120, 1140, 1175, 1185, 1260, 1290, 1300, 1375, 1440, 1450, 2850, 2920.

NMR Data:

| NMR Data: | | |
|---|---|---|
| .86 (d) | $CH_3-\overset{H}{C}$ | 3H |
| 2.04–1.00 (m) | Methylene and methine protons | 15H |
| 3.62 (m) | $-CH_2-O$ | 2H |

EXAMPLE III

Dehydration of 4-Hydroxy-4-Methyl-1-Oxaspiro(5.5) Undecane

Reaction:

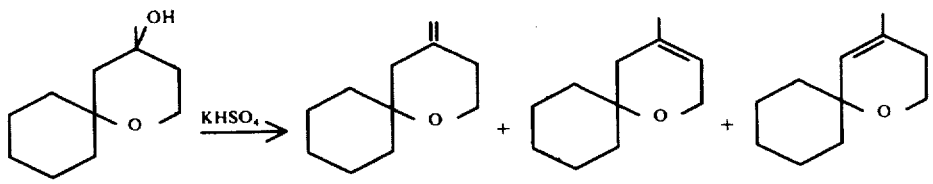

Into a 2 liter distillation flask fitted with a thermometer and a 12 inch Goodloe column (which in turn is fitted with an automatic head and fraction cutter) the following materials and placed:

| Amount | Ingredient |
|---|---|
| 1300 g | 4-hydroxy-4-methyl-1-oxaspiro (5.5) undecane |
| 65 g | Primol (See Note 3) |
| 65 g | KHSO$_4$ |
| 1 g | Ionol (See Note 4) |

At 15 mm Hg pressure and a vapor temperature of 105°–113° C the reaction mass is distilled yielding a mixture of compounds having the structures:

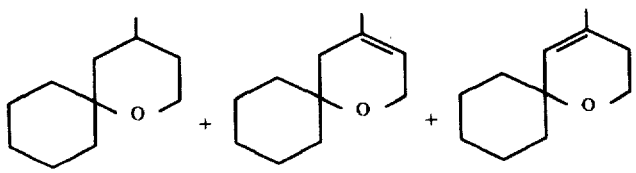

as confirmed by infrared analysis, mass spectral analysis and NMR analysis.

Note 3: Primol is a registered trademark identifying a hydrocarbon mineral oil produced by Exxon Incorporation of Linden, N.J.

Note 4: Ionol is a registered trademark identifying the compound 2,6-di-t-butyl-4-methylphenol.

EXAMPLE IV

Preparation of Mixture of
2-Methyl-4-Methylene-1-Oxaspiro[5.5]Undecane,
2,4-Dimethyl-1-Oxaspiro[5.5]Undec-3-ene,
2,4-Dimethyl-1-Oxaspiro[5.5]Undec-4-ene and
2,4-Dimethyl-4-Hydroxy-Oxaspiro[5.5]Undecane Reaction:

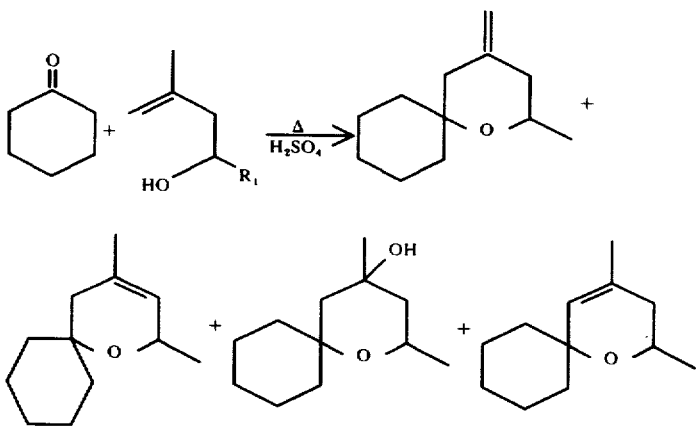

Into a 500 ml reaction flask equipped with stirrer, thermometer, Barrett trap reflux condenser and addition funnel is placed 490 gms. (5 moles) of cyclohexanone and 150 gm cyclohexane. The mixture is then heated to reflux and maintained at reflux. In a separate vessel, 597 gms. (5 moles) of 2-methyl-1-penten-4-ol, is placed, and 5 gm. concentrated sulfuric acid is added thereto dropwise while maintaining the temperature of 10° C. The resulting mixture of sulfuric acid and 2-methyl-1-penten-4-ol is then added over a period of one hour to the refluxing cyclohexanone. Refluxing is continued for a period of 4 hours. 85 ml H$_2$O is collected in the Barrett trap.

The reaction mass is then cooled to room temperature and 250 ml aqueous 10% NaOH is added thereto resulting in an aqueous and an organic phase. The organic phase is washed with one 250 ml portion of 10% aqueous sodium chloride.

The crude reaction product is stripped and rushed over after adding thereto 10 gms. of Primol and 0.1 gms. of Ionol at a vapor temperature of 55°–170° C; a liquid temperature of 94°–200° C and a vacuum of 15–7 mm Hg.

The rushed over material is then fractionated after adding thereto 10 gms. of Primol and 0.1 gms. of Ionox as follows:

| Fraction No. | Vapor Temp. | Liquid Temp. | Pressure (mm Hg) | Weight of Fraction | Reflux Ratio |
|---|---|---|---|---|---|
| 1 | 57–70° C | 88–89° C | 3.4–3.7 | 12.4 | 9:1 |
| 2 | 76 | 89 | 3.7 | 11.8 | 9:1 |
| 3 | 77 | 90 | 3.7 | 10.4 | 9:1 |
| 4 | 78 | 91 | 3.7 | 9.1 | 9:1 |
| 5 | 78 | 91 | 3.7 | 9.9 | 9:1 |
| 6 | 79 | 92 | 3.7 | 11.3 | 9:1 |
| 7 | 80 | 92 | 3.8 | 10.4 | 9:1 |
| 8 | 81 | 93 | 3.8 | 13.0 | 9:1 |
| 9 | 81 | 93 | 3.8 | 15.8 | 9:1 |
| 10 | 83 | 94 | 3.8 | 17.2 | 9:1 |
| 11 | 82 | 94 | 3.8 | 12.5 | 9:1 |
| 12 | 82 | 94 | 3.8 | 47.9 | 1:1 |
| 13 | 82 | 94 | 3.8 | 47.7 | 1:1 |
| 14 | 82 | 94 | 3.8 | 44.4 | 1:1 |
| 15 | 73 | 91 | 3.9 | 28.4 | 1:1 |
| 16 | 74 | 93 | 3.9 | 47.3 | 1:1 |
| 17 | 74 | 96 | 3.9 | 46.9 | 1:1 |
| 18 | 74 | 102 | 4.1 | 45.1 | 1:1 |
| 19 | 78 | 118 | 5.2 | 40.0 | 1:1 |
| 20 | 85 | 127 | 5.2 | 16.2 | 1:1 |
| 21 | 116 | 144 | 4.6 | 19.8 | 9:1 |
| 22 | 119 | 155 | 4.7 | 11.0 | 9:1 |
| 23 | 122 | 172 | 4.7 | 13.0 | 9:1 |
| 24 | 120 | 200 | 4.7 | 11.5 | 9:1 |

Fractions 15–19, as confirmed by infra-red, NMR and mass spectral analyses consists of more than 99% of a mixture of the compounds:

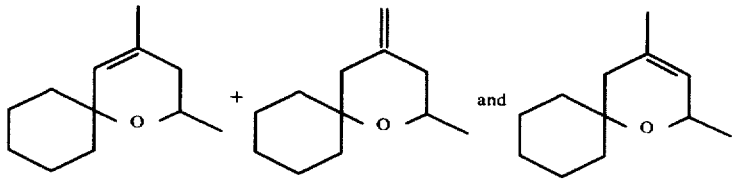

Figure 4:
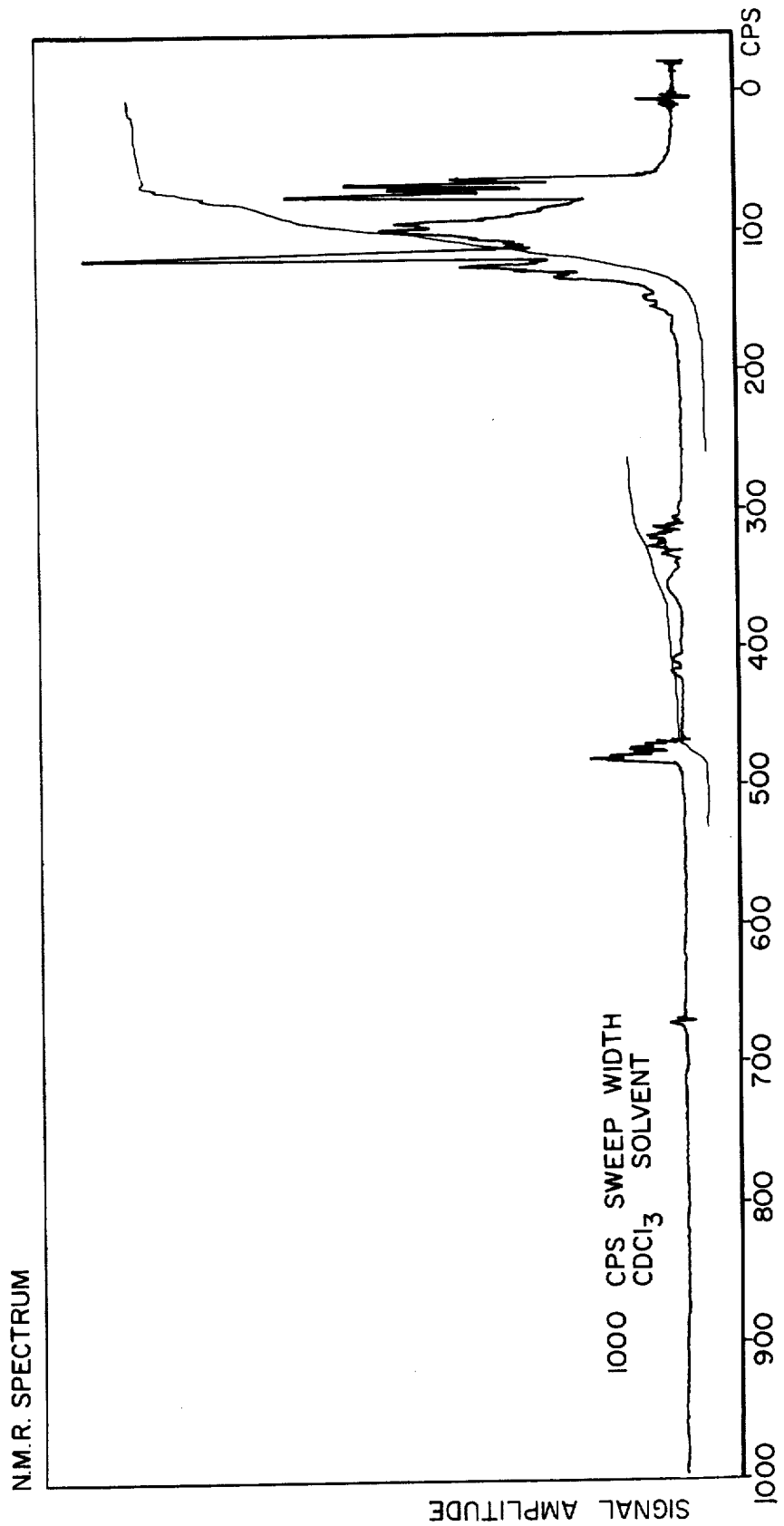
FIG. 4 represents the nuclear magnetic resonance spectrum for the product of Fraction 17 resulting from the fractional distillation of the product of Example IV, a mixture of 2-methyl-4-methylene-1-oxaspiro[5.5]undecane, 2,4-dimethyl-1-oxaspiro[5.5]undec-3-ene, 2,4-dimethyl-1-oxaspiro[5.5]undec-4-ene.

The NMR analysis data for Fraction 17 is set forth in FIG. 4.

Mass Spectral Data: Molecular ion, then in order of decreasing intensity: m/e = 180/137, 67, 43, 82, 41, 81.

Infra-Red Data: 400, 820, 910, 1000, 1010, 1030, 1050, 1075, 1090, 1110, 1140, 1150, 1160, 1175, 1180, 1260, 1320, 1350, 1360, 1375, 1440, 2850, 2920, 2980.

Nuclear Magnetic Resonance Data:

| | |
|---|---|
| 1.14 (d) | CH$_3$–C(H)–O– |
| 1.16 (d) | CH$_3$–C(H)–C– ‖ O |
| 1.62 (s) | =C–CH$_3$ |
| 1.98–1.40 (m) | –CH$_2$– |
| 3.60 (m) | H–C(H)–O– |
| 4.06 (m) | =C–C(H)–O |
| 4.64 (d) | –C=C–H ‖ H |
| 5.06 (m) | –C=C– ‖ H |

Fractions 21–24 as confirmed by infrared, NMR and means spectral analysis consists of the compound having the structure:

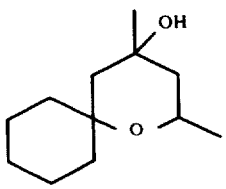

EXAMPLE V

Preparation of 2,4-Dimethyl-1-Oxaspiro(5.5) Undecane

Reaction:

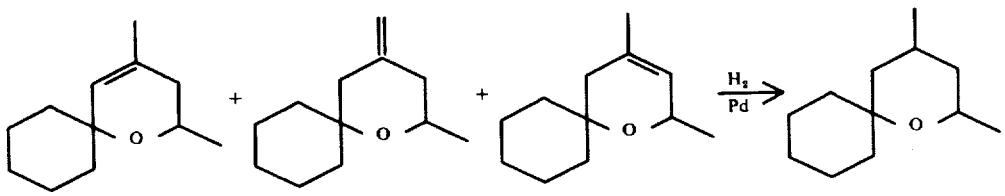

Into a 300 ml autoclave with a heating coil and shaker, the following materials are added:

| | |
|---|---|
| Isopropyl alcohol | 45 gms. |
| 5% Palladium on carbon catalyst | 0.6 gms. |
| Mixture of 2-methyl-4-methylene-1-oxaspiro[5.5]undecane, 2,4-dimethyl-1-oxaspiro[5.5]undec-3-ene and 2,4-dimethyl-1-oxaspiro[5.5]undec-4-ene produced according to | 45 gms. |

Example IV

The autoclave is then pressurized with hydrogen gas and operated at 100° C over a period of 21 hours periodically repressurizing the autoclave to 1000 psig.

The contents of the autoclave is then filtered and rushed over. The rushed over material is then distilled through a 2 inch splash column after adding thereto 5 gms. Primol, at a vapor temperature of 68° C and a pressure of 3.0 mm Hg.

Infrared and NMR analyses confirm the structure of the resulting product as being:

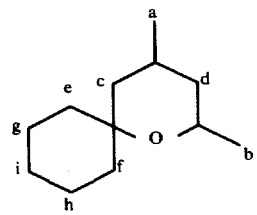

Infrared data: 810, 910, 990, 1000, 1030, 1040, 1055, 1070, 1090 1105, 1120, 1130, 1165, 1185, 1235, 1240, 1350, 1370, 1440, 2860, 2920 cm$^{-1}$.

| Nuclear Magnetic Resonance Data: | | |
|---|---|---|
| ppm | | Interpretation |
| 0.87 | (d) | protons in position at "a" in above structure (—CH$_3$) |
| 1.14 | (d) | protons in position at "b" in above structure (—CH$_3$) |
| 2.00–1.30 | (m) | protons in positions at "c", "d", "e", "f", "g", "h", "i" (—CH$_2$) |
| 3.64 | (m) | H–C(–O–) |

EXAMPLE VI

Dehydration of 4-Hydroxy-2,4-Dimethyl-1-Oxaspiro-(5.5) Undecane

Reaction:

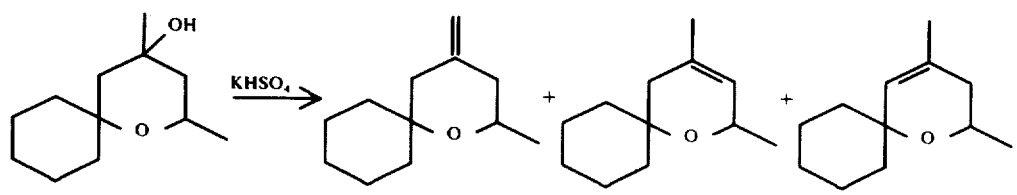

Into a 2 liter distillation flask fitted with a thermometer and a 12 inch Goodloe column (which in turn is fitted with an automatic head and fraction cutter) the following materials are placed:

| Amount | Ingredient |
|---|---|
| 1300 g | 4-hydroxy-2,4-dimethyl-1-oxaspiro(5.5) undecane |
| 65 g | Primol (See Note 5) |
| 65 g | KHSO$_4$ |
| 1 g | Ionol (See Note 6) |

At 3.9–5.2 mm Hg pressure and a vapor temperature of 73°–78° C the reaction mass is fractionated yielding a mixture of compounds having the structures:

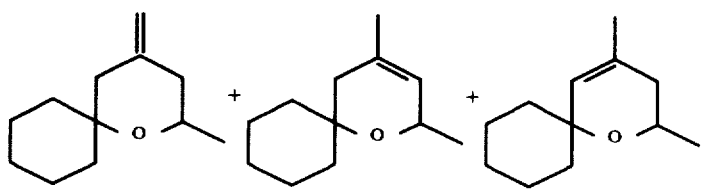

as confirmed by infrared analysis, mass spectral analysis and NMR analysis.

Note 5: Primol is a registered trademark identifying a hydrocarbon mineral oil produced by Exxon Incorporation of Linden, N.J.

Note 6: Ionol is a registered trademark identifying the compound 2,6-di-t-butyl-4-methylphenol.

EXAMPLE VII

PREPARATION OF MIXTURE OF 8,8,10-TRIMETHYL-4-METHYLENE-1-OXASPIRO[5.5]UNDECANE; 4,8,8,10-TETRAMETHYL-1-OXASPIRO[5.5]UNDEC-3-ENE; 4,8,8,10-TETRAMETHYL-1-OXASPIRO[5.5]UNDEC-4-ENE AND 4-HYDROXY-4,8,8,10-TETRAMETHYL-1-OXASPIRO[5.5]UNDECANE

Reaction:

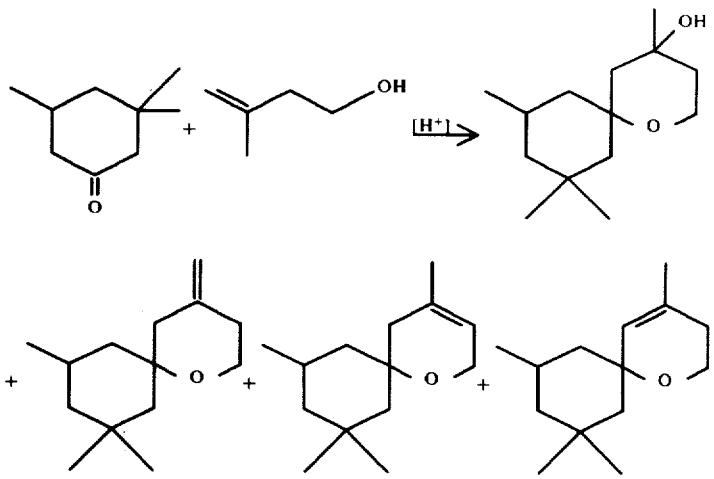

Into a 1 liter reaction flask equipped with stirrer, thermometer, reflux condenser and addition funnel is placed 250 gms. (1.95 moles) of 3,3,5-trimethyl cyclohexanone. In a separate vessel, 168 grams (1.95 moles) of 3-methyl-3-buten-1-ol is placed and 2 gms. of concentrated sulfuric acid is added thereto dropwise while maintaining the temperature of 10° C. The resulting mixture of sulfuric acid and 3-methyl-3-buten-1ol is then added over a period of one hour to the 3,3,5-trimethyl cyclohexanone which has been preheated to 80°–85° C, while maintaining the temperature in the range of 80°–85° C.

After the addition the reaction mass is stirred at 80°–85° C for a period of 9 hours.

The reaction mass is then cooled to room temperature and 100 ml of 10% aqueous NaOH is added thereto, yielding two phases; an aqueous and an organic phase. The organic phase is washed with one 100 ml portion of 10% aqueous sodium chloride.

The crude reaction product is then rushed over after adding thereto 10 gms. of Primol and 0.1 gms. of Ionol at a vapor temperature of 69°–153° C; a liquid temperature of 75°–200° C and a vacuum of 0.8–3.5 mm Hg.

The rushed over material is then fractionated after adding thereto 4.5 gms. of Primol, 0.1 gms. of Ionol and 0.5 gms. of triethanolamine as follows:

| Fraction No. | Vapor Temp. | Liquid Temp. | Pressure (mm Hg) | Weight of Fraction | Reflux Ratio |
|---|---|---|---|---|---|
| 1 | 49–51 | 74–76 | 3.7–3.4 | 19.3 | 20:1 |
| 2 | 51 | 77 | 3.7 | 20.1 | 20:1 |
| 3 | 51 | 79 | 4.0 | 20.3 | 20:1 |
| 4 | 51 | 83 | 3.9 | 19.5 | 20:1 |
| 5 | 51 | 88 | 4.0 | 22.3 | 20:1 |
| 6 | 51 | 98 | 4.0 | 22.4 | 20:1 |
| 7 | 54 | 107 | 4.0 | 6.1 | 20:1 |
| 8 | 68 | 110 | 3.0 | 6.7 | 20:1 |
| 9 | 74 | 116 | 3.0 | 3.5 | 20:1 |
| 10 | 82 | 120 | 3.0 | 8.4 | 20:1 |
| 11 | 82–89 | 111–113 | 3.5 | 20.1 | 20:1 |
| 12 | 90 | 118 | 3.6 | 26.7 | 20:1 |
| 13 | 92 | 129 | 3.7 | 21.3 | 20:1 |
| 14 | 106 | 141 | 3.7 | 9.8 | 20:1 |
| 15 | 115 | 154 | 3.5 | 6.8 | 20:1 |
| 16 | 118 | 163 | 3.5 | 12.8 | 20:1 |
| 17 | 146 | 189 | 3.5 | 13.3 | 20:1 |
| 18 | 162 | 202 | 3.0 | 6.0 | 20:1 |

Fraction 13 is confirmed by IR, mass spectral and NMR analyses to be a mixture of compounds having the structures:

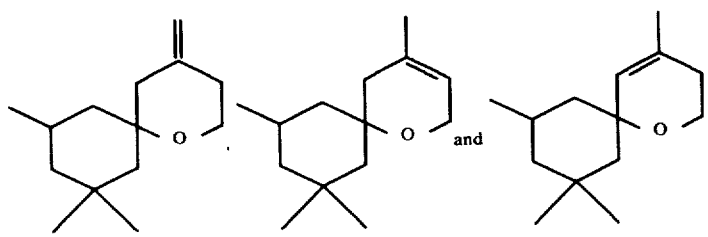

Figure 5:
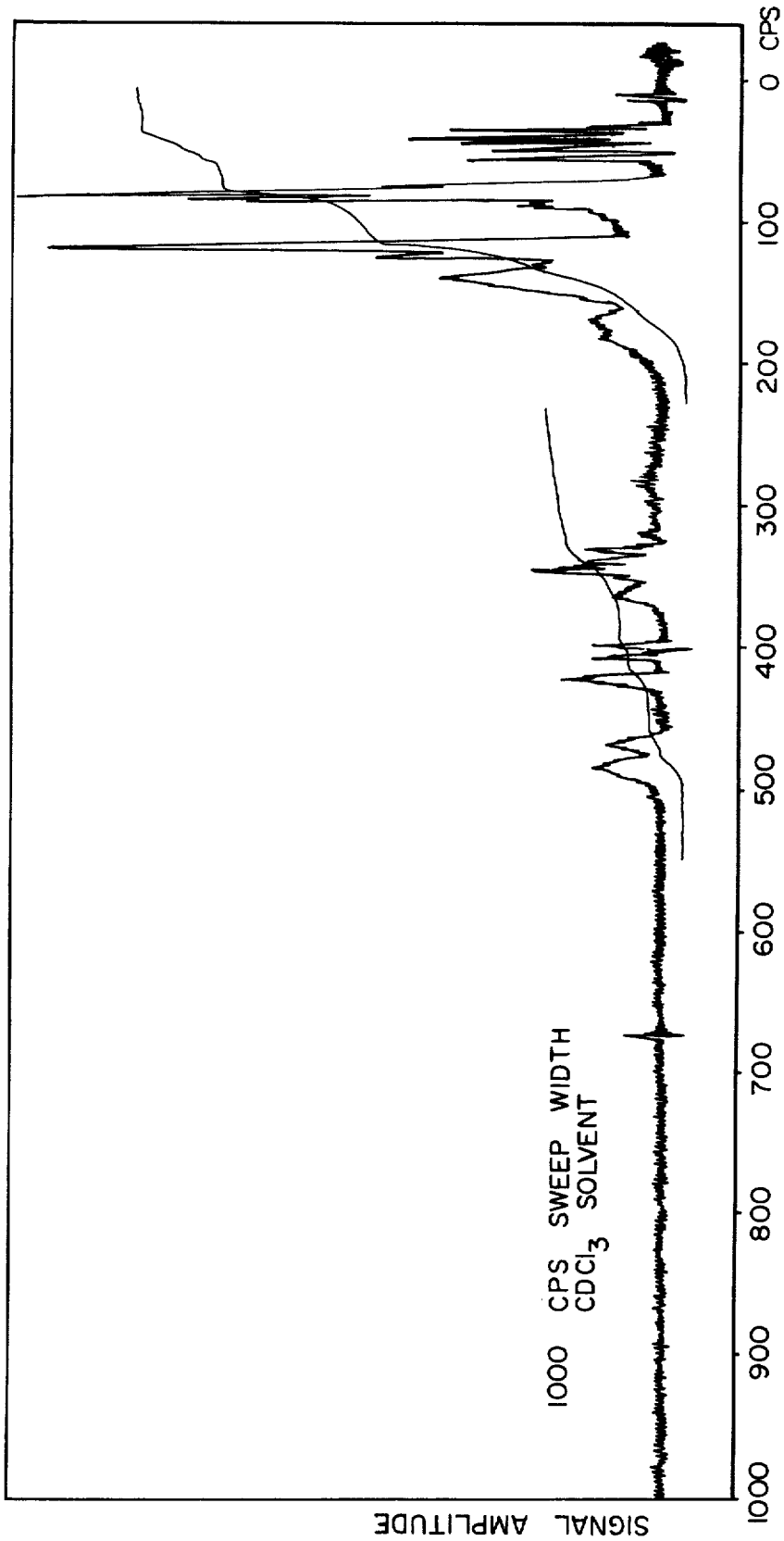
FIG. 5 represents the nuclear magnetic resonance spectrum for Fraction 10 resulting from the fractional distillation of the product of Example VII, a mixture of 8,8,10-trimethyl-4-methylene-1-oxaspiro[5.5]undecane, 4,8,8,10-tetramethyl-1-oxaspiro[5.5]undec-3-ene, 4,8,8,10-tetramethyl-1-oxaspiro[5.5]undec-4-ene.

The NMR spectrum for Fraction 10 is set forth in FIG. 5.

Mass Spectral Data: Molecular ion, then in decreasing intensity: m/e = 208/137, 68, 41, 83, 69, 39.

Infra-Red Data: 820, 890, 960, 980, 1020, 1050, 1075, 1100, 1125, 1160, 1170, 1180, 1210, 1225, 1260, 1360, 1380, 1415, 1425, 1430, 2880, 2920, 2970.

| Nuclear Magnetic Resonance Data: | |
|---|---|
| 0.86 (doublets): (3H) | $CH_3-\overset{H}{\underset{}{C}}$ |
| 1.22 gem dimethyl protons (6H) 1.67 (3H) 2.44–1.68 methylene and methine protons 3.86 (m) 4.14 (m) 4.60 (d) | $=C-CH_3$ $\begin{array}{c}CH_2-O-\\=C-CH_2-O\\ \diagdown \quad /H \\ -C=C \diagdown_H\end{array}$ |
| 5.22 (m) olefinic proton | |

EXAMPLE VIII

Dehydration of
4-Hydroxy-4,8,8,10-Tetramethyl-1-Oxaspiro (5.5.) Undecane

Reaction:

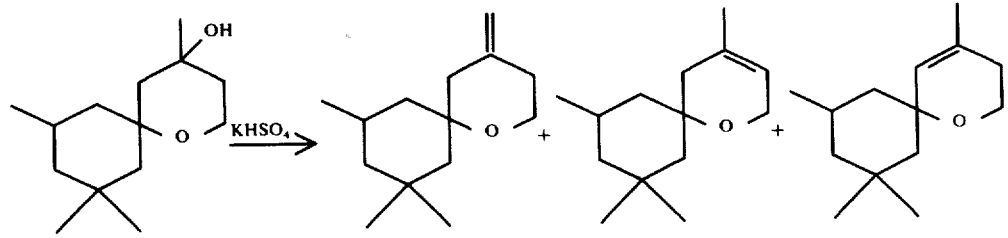

Into a 2 liter distillation flask fitted with a thermometer and a 12 inch Goodloe column (which in turn is fitted with an automatic head and fraction cutter) the following materials are placed:

| Amount | Ingredient |
|---|---|
| 1300 g | 4-hydroxy-4,8,8,10-tetramethyl-1-oxaspiro(5.5) undecane |
| 65 g | Primol (See Note 7) |
| 65 g | KHSO₄ |
| 1 g | Ionol (See Note 8) |

At 3.7 mm Hg pressure and a vapor temperature of 92° C the reaction mass is fractionated yielding a mixture of compounds having the structures:

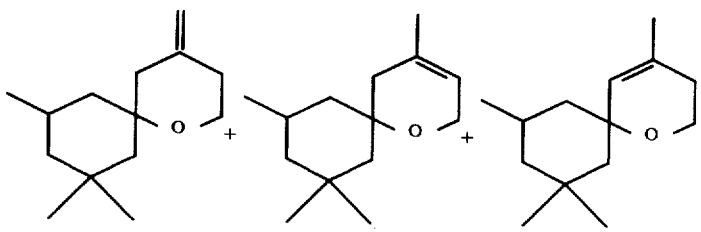

as confirmed by infrared analysis, mass spectral analysis and NMR analysis.

Note 7: Primol is a registered trademark identifying a hydrocarbon mineral oil produced by Exxon Inc. of Linden, N.J.

Note 8: Ionol is a registered trademark identifying the compound 2,6-di-t-butyl-4-methylphenol.

EXAMPLE IX

Preparation of Mixture
9-t-Butyl-4-Methylene-1-Oxaspiro[5.5]Undecane;
9-t-Butyl-4-Methyl-1-Oxaspiro[5.5]Undec-3-ene and
9-t-Butyl-4-Methyl-1-Oxaspiro[5.5]Undec-4-ene Reaction:

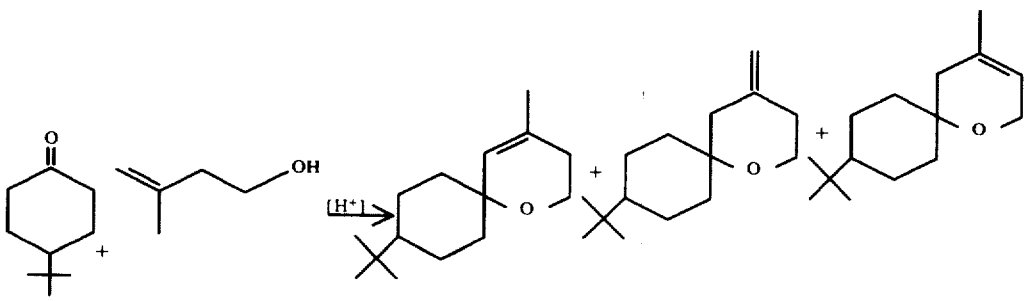

Into a 1 liter 3-necked reaction flask equipped with stirrer, thermometer, reflux condenser, Barrett trap and addition funnel is placed 284 gms. (2 moles) of t-butyl cyclohexanone and 125 ml cyclohexane. This mixture is then heated to 108° C and maintained at that temperature. In a separate reaction vessel, is placed 172 gms. (2 moles) of 3-methyl-3-buten-1-ol. 2 gms. of concentrated sulfuric acid is added thereto dropwise while maintaining the temperature of 10° C. The resulting mixture of sulfuric acid and 3-methyl-3-buten-1-ol is then added over a period of 1 hour to the t-butyl cyclohexanone solution, while maintaining the reaction mass temperature at reflux about (108° C).

After the addition, the reaction mass is stirred maintaining its temperature at about 108° C for a period of 4 hours, while collecting water (a reaction product) in the Barrett trap. 38 ml H$_2$O is collected after 4 hours.

The reaction mass is then cooled to room temperature and 2 g KOH is added thereto.

The crude reaction product is then rushed over after adding thereto 10 gms. of Primol and 0.1 gms. of Ionol at a vapor temperature of 105°–143° C; a liquid temperature of 121°–200° C and a vacuum of 2.9 mm Hg.

The rushed over material is then fractionated after adding thereto 4.5 gms. of Primol, 0.1 gms. of Ionol and 0.5 gms. of triethanolamine.

The fractional distillation data for the resulting reaction product is as follows:

| Fraction Number | Vapor Temp. | Liquid Temp. | Pressure (mm Hg) | Weight of Fr. | Reflux Ratio |
|---|---|---|---|---|---|
| 1 | 72–105° C | 126–132° C | 2.9 | 6.0 | 20:1 |
| 2 | 107 | 133 | 3.0 | 7.2 | 20:1 |
| 3 | 108 | 133 | 3.0 | 9.0 | 20:1 |
| 4 | 108 | 133 | 3.1 | 9.0 | 20:1 |
| 5 | 109 | 132 | 3.1 | 25.7 | 9:1 |
| 6 | 109 | 132 | 3.1 | 29.1 | 9:1 |
| 7 | 109 | 133 | 3.1 | 26.6 | 9:1 |
| 8 | 109 | 133 | 3.1 | 27.0 | 9:1 |
| 9 | 110 | 134 | 3.1 | 26.1 | 9:1 |
| 10 | 110 | 134 | 3.1 | 28.8 | 9:1 |
| 11 | 110 | 134 | 3.1 | 28.0 | 9:1 |
| 12 | 110 | 138 | 3.1 | 27.7 | 9:1 |
| 13 | 111 | 144 | 3.1 | 25.1 | 9:1 |
| 14 | 115 | 180 | 3.1 | 9.2 | 9:1 |
| 15 | 130 | 204 | 3.1 | 4.5 | 9:1 |

IR, NMR and mass spectral analysis confirms that the composition of bulked Fractions 5–14 consist of the following three compounds:

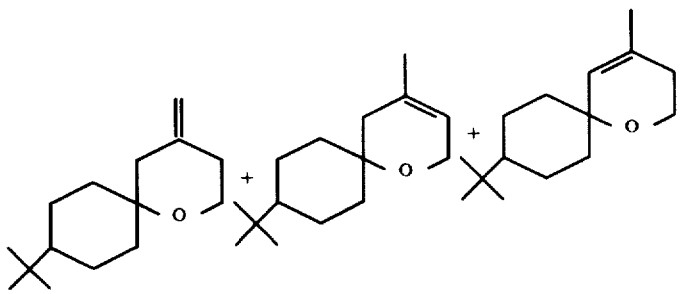

The NMR analysis for Fraction 13 is as follows:

| PEAK | INTERPRETATION |
| --- | --- |
| 0.80 ppm(s) | $\underset{\underset{CH_3}{\mid}}{\overset{\overset{CH_3}{\mid}}{CH_3-C-}}$ |
| 1.66(broad) | $=C-CH_3$ |
| 2.00 – 1.00(m) | $-CH_2-$ |
| 3.78(m) | $CH_2-O-$ |
| 4.04(m) | $=C-CH_2-O$ |
| 4.70(d) | $-C=C\underset{H}{\overset{H}{\diagup}}$ |

Figure 6:
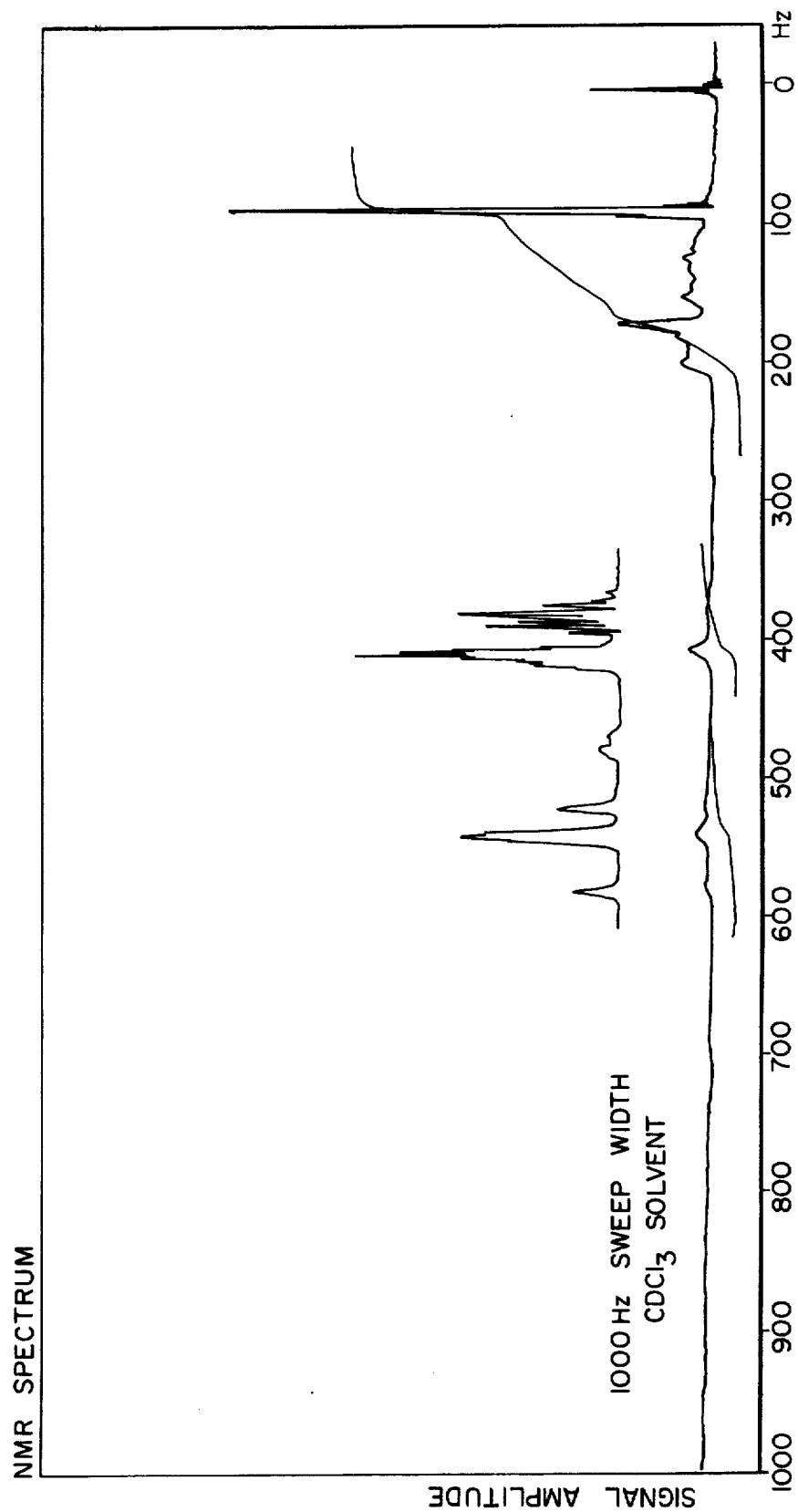
FIG. 6 represents the nuclear magnetic resonance spectrum for Fraction 13 resulting from the fractional distillation of the product of Example IX, a mixture of 9-t-butyl-4-methylene-1-oxaspiro[5.5]undecane, 9-t-butyl-4-methyl-1-oxaspiro[5.5]undec-3-ene and 9-t-butyl-4-methyl-1-oxaspiro[5.5]undec-4-ene.

The NMR spectrum for Fraction 13 is set forth in FIG. 6.

The infrared analysis for fraction 13 is as follows: 410, 780, 870, 930, 1010, 1035, 1080, 1105, 1145, 1160, 1195, 1215, 1240, 1360, 1380, 1440, 1465, 1475, 2820, 2860, 2930.

Figure 7:
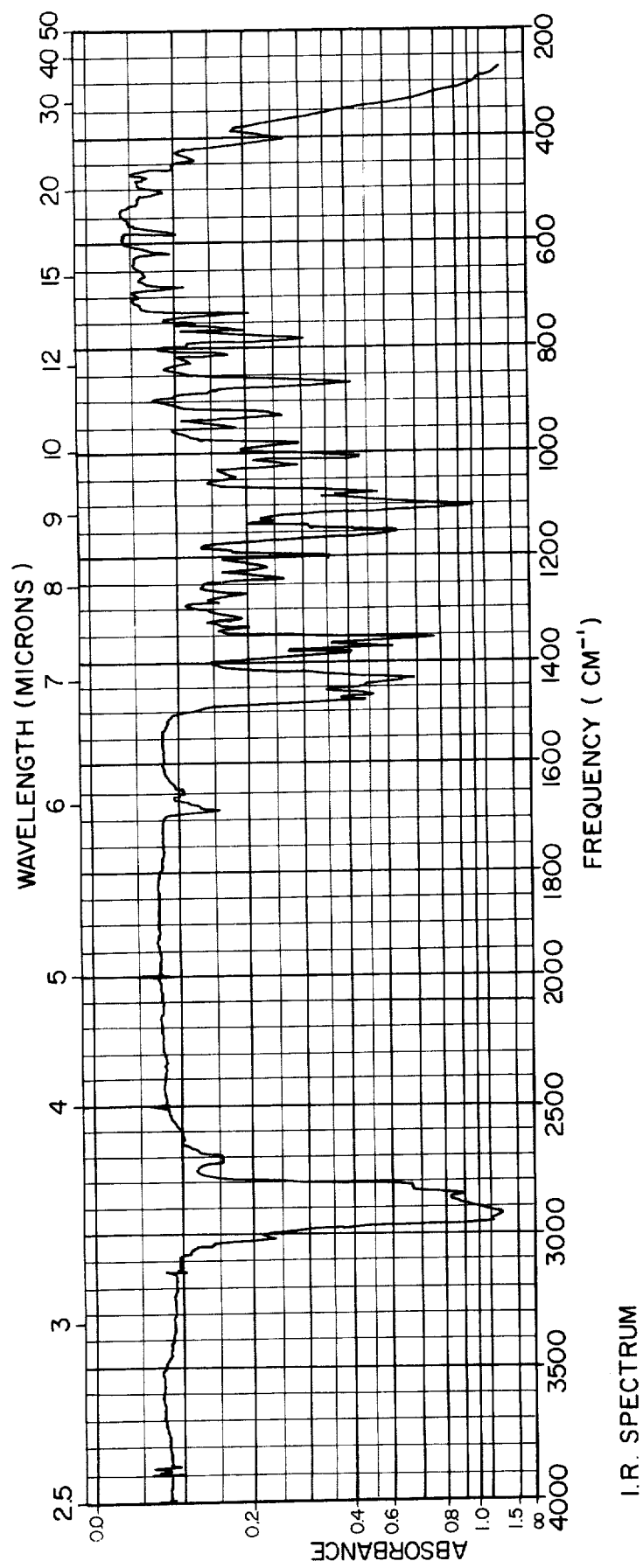
FIG. 7 is the infra-red spectrum for Fraction 13 resulting from the fractional distillation of the product of Example IX, a mixture of 9-t-butyl-4-methylene-1-oxaspiro[5.5]undecane, 9-t-butyl-4-methyl-1-oxaspiro[5.5]undec-3-ene and 9-t-butyl-4-methyl-1-oxaspiro[5.5]undec-4-ene.

The infra red spectrum for Fraction 13 of this mixture is set forth in FIG. 7.

The mass spectral analysis for Fraction 13 is as follows: (molecular ion, then is decreasing intensity): m/e= 222/123, 41, 57, 68, 55, 67.

Fraction 13 evaluated at 1ppm has a weedy, green, herbaceous aroma and a taste which gives an initial sweet effect changing to an astringent note. At 5ppm the mixture of Fraction 13 has a strong weedy, green aroma with vegetable green, over-ripe green pepper-like notes; and a taste wherein the vegetable character dominates having sweet artichoke-like undertones.

EXAMPLE X

Dehydration of
4-Hydroxy-4-Methyl-9-t-Butyl-1-Oxaspiro(5.5) Undecane

Reaction:

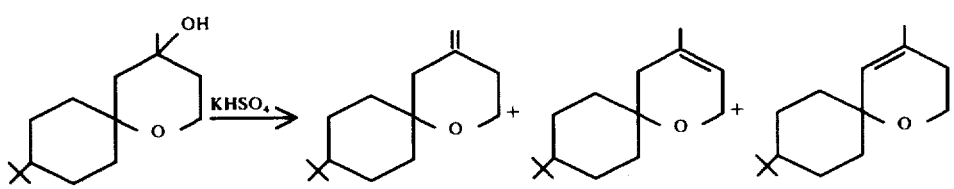

Into a 2 liter distillation flask fitted with a thermometer and a 12 inch Goodloe column (which in turn is fitted with an automatic head and fraction cutter) the following materials are placed:

| Amount | Ingredient |
| --- | --- |
| 1300 g | 4-hydroxy-4-methyl-9-t-butyl-1-oxaspiro(5.5) undecane |
| 65 g | Primol |
| 65 g | KHSO$_4$ |
| 1 g | Ionol |

At 3.1 mm Hg pressure and a vapor temperature of 109°–115° C the reaction mass is fractionated yielding a mixture of compounds having the structures:

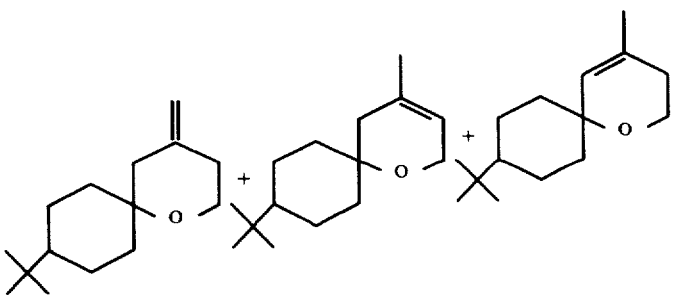

as confirmed by infrared analysis, mass spectral analysis and NMR analysis.

EXAMPLE XI

Hyacinth Perfume Formulation

The following mixture is prepared:

| Ingredients | Parts by Weight |
|---|---|
| Cinnamic alcohol | 40 |
| Heliotropin | 20 |
| Galaxolide (50% in diethyl phthalate) (1,3,4,6,7,8-hexahydro-4,6,6,7,8,8-hexamethyl-cyclopenta-gamma-2-benzopyran) | 10 |
| Dimethyl hydroquinone | 5 |
| Indol | 2 |
| Lyral ((4-(4-hydroxy-4-methyl-pentyl)-3-cyclohexene-1O-carboxaldehyde) | 70 |
| Amyl cinnamic aldehyde | 20 |
| Hexyl cinnamic aldehyde | 70 |
| Phenylethyl alcohol | 150 |
| Benzyl alcohol | 25 |
| Benzyl acetate | 50 |
| Geraniol coeur | 10 |
| Citronellol coeur | 20 |
| Aubepine (para-methoxy benzaldehyde) | 15 |
| Benzyl salicylate | 5 |
| Eugenol | 10 |
| Methyl eugenol | 5 |
| Terpineol | 15 |
| Isoeugenol | 30 |
| Galbanum coeur | 10 |
| Methyl anthranilate | 2 |
| Ylang extra | 10 |
| Nerolidol | 40 |
| Phenyl ethyl salicylate | 40 |
| Mixture of 2-methyl-4-methylene-1-oxaspiro[5.5]undecane, 2,4-dimethyl-1-oxaspiro[5.5]undec-3-ene and 2,4-dimethyl-1-oxaspiro[5.5]undec-4-ene produced according to Example IV. | 15 |
| Mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene produced according to Example VII | 25 |

The mixture of 2,4-dimethyl-1-oxaspiro[5.5] undec-3-ene, 2,4-dimethyl-1-oxaspiro[5.5]undec-4-ene and 2-methyl-4-methylene-1-oxaspiro[5.5]undecane imparts a green, sweet, floral, herbaceous top note to the hyacinth perfume formulation. The mixture of 4,8,8,10-tetramethyl-1-oxaspiro[5.5]undec-3-ene, 4,8,8,10-tetramethyl-1-oxaspiro[5.5]undec-4-ene and 8,8,10-trimethyl-4-methylene-1-oxaspiro[5.5]undecane imparts a green floral tone to the bottom note to the hyacinth perfume formulation.

EXAMPLE XII

Geranium Perfume Formulation

The following mixture is prepared:

| Ingredients | Parts by Weight |
|---|---|
| Geraniol coeur | 200 |
| Citronellol coeur | 350 |
| Linalool | 15 |
| Citronellyl formate | 50 |
| Citronellyl acetate | 10 |
| Geranyl acetate | 50 |
| Benzyl butyrate | 5 |
| 4-Methyl-1-oxaspiro(5.5) undecane | 40 |

-continued

| Ingredients | Parts by Weight |
|---|---|
| produced according to the process of Example II | |

The 4-methyl-1-oxaspiro(5.5) undecane imparts the green, minty top note so necessary for geranium bourbon to the geranium perfume formulation.

EXAMPLE XIII

Basil Perfume Formulation

The following mixture is prepared:

| Ingredients | Parts by Weight |
|---|---|
| Linalool | 45 |
| Methyl chavicol | 20 |
| Eugenol | 3 |
| Isoeugenol | 1 |
| Terpineol | 5 |
| Bisabolene | 3 |
| Nerolidol | 1 |
| Mixture of 4-methylene-1-oxaspiro[5.5]undecane, 4-methyl-1-oxaspiro[5.5]undec-3-ene and 4-methyl-1-oxaspiro[5.5]undec-4-ene produced according to Example IV | 15 |

The mixture of 4-methylene-1-oxaspiro[5.5] undecane, 4-methyl-1-oxaspiro[5.5]undec-3-ene and 4-methyl-1-oxaspiro[5.5]undec-4-ene imparts the green, herbal top note of basil to the basil perfume formulation.

EXAMPLE XIV

Use of 4-Methyl-1-Oxaspiro(5.5) Undecane as Flavorant

4-Methyl-1-oxaspiro(5.5) undecane added at the rate of 0.3 ppm to a "low quality" cup of hot tea provided by a vending machine improves the aroma and taste of the tea substantially. The flavored and unflavored teas are compared by a 5-member bench panel. The flavored tea is unanimously considered by the bench panel as having a fresher, more aromatic, honey-like aroma and a more pleasant fresher, aromatic taste.

When the 4-methyl-1-oxaspiro(5.5) undecane is added to the tea at the rate of 10 ppm, a pleasant, minty, cooling note (which is preferred over menthol by 4 our of the 5 members of the bench panel) occurs. The 4-methyl-1-oxaspiro(5.5) undecane is considered to give rise to a novel type of "cooling" taste different from menthol.

EXAMPLE XV

Raspberry Flavor Formulation

The following formulation is prepared:

| Ingredient | Parts by Weight |
|---|---|
| Raspberry ketone (oxyphenylon) | 4 |
| Vanillin | 1 |
| Maltol | 2 |
| Alpha-ionone | 0.5 |
| Iso butylacetate | 20 |
| Ethylbutyrate | 5.5 |
| Dimethyl sulfide | 1 |
| Acetic acid | 30 |
| Acetaldehyde | 16 |

-continued

| Ingredient | Parts by Weight |
|---|---|
| Propylene glycol | 920 |

When added at the rate of 1% to the above formulation the 4-methyl-1-oxaspiro(5.5) undecane adds a more natural character thereto. A 5-member bench panel unanimously agrees that the formulation containing 1% of 4-methyl-1-oxapsiro(5.5) undecane is more raspberry-kernel like; more piney; has a wild raspberry or herbaceous taste and has a natural berry character. The flavor formulation containing the 1% of 4-methyl-1-oxaspiro(5.5) undecane is unanimously preferred over the flavor formulation not containing any 4-methyl-1-oxaspiro(5.5) undecane. The flavor formulation are compared side-by-side at the rate of 40 ppm in water.

EXAMPLE XVI

The following mixture is prepared:

| Ingredients | Parts by Weight |
|---|---|
| Natural Raspberry Concentrate Juice | 2½% |
| Water | 85% |
| Sugar syrup (37.5° Baume) | 12½% |

The wild raspberry, herbaceous and seedy, raspberry kernel notes of this raspberry juice is imparted in increased strength by addition of 4-methyl-1-oxaspiro(5.5) undecane at the rate of from 20 parts per million up to 50 parts per million.

EXAMPLE XVII

To the raspberry formulation of Example XV, 4-methyl-1-oxaspiro(5.5) undecane at the rate of 0.2% is added. This material is then called the "test composition". The raspberry formulation without 4-methyl-1-oxaspiro(5.5) undecane is called the "control composition".

The test and control compositions are added to the food products described hereinafter in the proportions shown for 10 kilograms of material to be flavored:

| Pudding | 5–10 grams (0.15–.1%) |
|---|---|
| Cooked sugar | 15–20 grams (.15–2%) |

Cooked sugar — 100 ml of sugar syrup (prepared by dissolving 1 kilogram of sucrose in 600 ml of water) and 20 grams of glucose are mixed together and slowly heated to 145° C. The flavor is added and the mass allowed to cool and harden.

Pudding — To 500 ml of warmed milk are added with stirring a mixture of 60 grams sucrose and 3 grams of pectin. The mixture is boiled for a few seconds and the flavor is added. The mixture was allowed to cool.

The finished foodstuff samples are tested by a panel of trained persons who express their views about the flavor of the samples. All members of the panel prefer the test samples having a more distinguished wild raspberry aroma with taste of the wild raspberries and its herbaceous and kernel notes.

EXAMPLE XVIII

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes.

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with the mixture of 4-methylene-1-oxaspiro (5.5) undecane, 4-methyl-1-oxaspiro(5.5) undec-3-ene and 4-methyl-1-oxaspiro[5.5]undec-4-ene produced according to Example I at 100 ppm per cigarette. Another third of these model cigarettes are treated in the filter with the mixture of 4-methylene-1-oxaspiro[5.5]undecane, 4-methyl-1-oxaspiro[5.5]undec-3-ene and 4-methyl-1-oxaspiro[5.5]undec-4-ene at the rate of $2 \times 10^{-5}$ gm. and $3 \times 10^{-5}$ gm. When evaluated by paired comparison, the cigarettes treated both in the tobacco and in the filter with the mixture of 4-methyl-1-oxaspiro[5.5]undec-3-ene, 4-methyl-1-oxapsiro[5.5]undec-4-ene and 4-methylene-1-oxaspiro[5.5]undecane are found, in smoke flavor, to be more aromatic, more sweet, cooling (sensation in the mouth) and more tobacco like in character. In addition, there is a more cooling sensation in the aftertaste.

EXAMPLE XIX

A tobacco blend is made up by mixing the following materials:

| Ingredient | Parts by Weight |
|---|---|
| Bright | 40.1 |
| Burley | 24.9 |
| Maryland | 1.1 |
| Turkish | 11.6 |
| Stem (flue cured) | 14.2 |
| Glycerine | 2.8 |
| Water | 5.3 |

The above tobacco is used in producing cigarettes and the following formulation is compounded and incorporated into each of these cigarettes:

| Ingredient | Parts by Weight |
| --- | --- |
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model filter cigarettes at the rate of 0.1%. One-third of these model cigarettes are treated in the tobacco section with the 4-methyl-1-oxaspiro(5.5) undecane produced according to Example II at 100 ppm per cigarette. Another third of these model cigarettes are treated in the filter with the 4-methyl-1-oxaspiro(5.5) undecane at the rate of $2 \times 10^{-5}$ gm. and $3 \times 10^{-5}$ gm. When evaluated by paired comparison the cigarettes treated both in the tobacco and in the filter with the 4-methyl-1-oxaspiro(5.5) undecane are found in smoke flavor to be more aromatic, more sweet, cooling (sensation in the mouth) and more tobacco like in character. In addition, there is a more cooling sensation in the aftertaste.

EXAMPLE XX

Preparation of Soap Composition

One hundred grams of soap chips are mixed with one gram of the perfume composition of Example XI until a substantially homogeneous composition is obtained. The perfumed soap composition exhibits a hyacinth fragrance containing an excellent green, floral and herbaceous notes so essential to orange flower.

EXAMPLE XXI

Preparation of a Detergent Composition

A total of 100 grams of a detergent powder is mixed with 0.15 grams of the perfume composition of Example XI until a substantially homogeneous composition is prepared. This composition exhibits an hyacinth fragrance containing a green, floral and herbaceous notes essential to orange flower.

EXAMPLE XXII

Preparation of a Cosmetic Powder Composition

A cosmetic powder is prepared by mixing in a ball mill, 100 grams of talcum powder with 2 grams of the composition of Example XI. It has a hyacinth aroma with green, floral and herbaceous notes.

EXAMPLE XXIII

Perfumed Liquid Detergent

Concentrated liquid detergent with a hyacinth character is obtained containing 1.0%, 1.5% and 2.0% of the composition of Example XI. It is prepared by adding and homogeneously mixing the appropriate quantity of the composition of Example XI in the liquid detergent. The detergents all possess a hyacinth aroma with green, floral and herbaceous notes, the intensity increasing with greater concentrations of composition of Example XI.

EXAMPLE XXIV

Cologne

The composition of Example XI is incorporated in a cologne at a concentration of 2.5% in 85% aqueous ethanol; and into a handkerchief perfumes at a concentration of 20%( in 95% aqueous ethanol). A distinct and definite hyacinth fragrance containing green, floral and herbaceous notes essential to hyacinth is imparted to the cologne and to the handkerchief perfume.

EXAMPLE XXV

Cologne

The composition of Example XII is incorporated in a cologne at a concentration of 2.5% in 85% aqueous ethanol; and into a handkerchief perfume at a concentration of 20% (in 95% aqueous ethanol). The composition of Example XII affords a distinct and definite geranium bourbon fragrance containing green, minty top notes found in geranium to the handkerchief perfume and cologne.

EXAMPLE XXVI

Preparation of Soap Composition

One hundred grams of soap chips are mixed with one gram of the perfume composition of Example XII until a substantially homogeneous composition is obtained. The perfumed soap composition exhibits a geranium bourbon fragrance having a green, minty top note.

EXAMPLE XXVII

Preparation of a Detergent Composition

A total of 100 grams of a detergent powder is mixed with 0.15 grams of the perfume composition of Example XIII until a substantially homogeneous composition is prepared. This composition exhibits a basil fragrance having a green, herbal, note.

EXAMPLE XXVIII

PREPARATION OF A COSMETIC POWDER COMPOSITION

A cosmetic powder is prepared by mixing in a ball mill, 100 grams of talcum powder with 2.5 grams of the perfume composition of Example XII. It has a geranium bourbon fragrance with a green, minty top note.

EXAMPLE XXIX

PERFUMED LIQUID DETERGENT

Concentrated liquid detergent with a basil fragrance having a green, herbal top note is obtained containing 1.0%, 1.5% and 2.0% of the composition of Example XIII. It is prepared by adding and homogeneously mixing the appropriate quantity of the composition of Example XIII in the liquid detergent. The detergents all possess a basil aromas and green, herbal top notes, the intensity increasing with greater concentrations of composition of Example XIII.

EXAMPLE XXX

COLOGNE

The composition of Example XIII is incorporated in a cologne at a concentration of 2.5% in 85% aqueous ethanol; and into a handkerchief perfume at a concentration of 20% (in 95% aqueous ethanol). A distinct and definite basil aroma with green, herbal top notes is imparted to the cologne and to the handkerchief perfume.

EXAMPLE XXXI

PREPARATION OF SOAP COMPOSITION

One hundred grams of soap chips are mixed with 1 gram of the mixture of 4-methylene-1-oxaspiro [5.5]undecane, 4-methyl-1-oxaspiro[5.5]undec-3-ene and 4-methyl-1-oxaspiro[5.5]undec-4-ene prepared according to Example I until a substantially homogeneous composition is obtained. The perfumed soap composition exhibits a green, basil, floral, herbal and eucalyptol-aroma.

EXAMPLE XXXII

PREPARATION OF A DETERGENT COMPOSITION

A total of 100 grams of a detergent powder is mixed with 0.15 grams of the mixture of 4-methylene-1-oxaspiro[5.5]undecane, 4-methyl-1-oxaspiro [5.5]undec-3-ene and 4-methyl-1-oxaspiro[5.5]undec4-ene prepared according to Example I until a substantially homogeneous composition is prepared. This composition exhibits a green, basil, floral, herbal and eucalyptol-like aroma.

EXAMPLE XXXIII

PREPARATION OF A COSMETIC POWDER COMPOSITION

A cosmetic powder is prepared by mixing in a ball mill, 100 grams of talcum powder with 0.25 grams of the mixture of 4-methylene-1-oxaspiro[5.5] undecane, 4-methyl-1-oxaspiro[5.5]undec-3-ene and 4-methyl-1-oxaspiro[5.5]undec-4-ene prepared according to Example I. It has a pleasant green, basil-like, eucalyptol-like aroma with a floral undertone.

EXAMPLE XXXIV

PERFUMED LIQUID DETERGENT

Concentrated liquid detergent with a green, basil-like character is obtained containing 0.10%, 0.15% and 0.20% of the mixture of 4-methylene-1-oxaspiro[5.-5]undecane, 4-methyl-1-oxaspiro[5.5] undec-3-ene and 4-methyl-1-oxaspiro[5.5]undec-4-ene prepared according to Example I. It is prepared by adding and homogeneously mixing the appropriate quantity of the mixture of 4-methylene-1-oxaspiro [5.5]undecane, 4-methyl-1-oxaspiro[5.5]undec-3-ene and 4-methyl-1-oxaspiro[5.5]undec-4-ene prepared according to Example I in the liquid detergent. The detergents all possess green, basil-like, floral notes, the intensity increasing with greater concentrations of the mixture of 4-methylene-1-oxaspiro [5.5]undecane, 4-methyl-1-oxaspiro[5.5]undec-3-ene and 4-methyl-1-oxaspiro[5.-5]undec-4-ene prepared according to Example I.

EXAMPLE XXXV

COLOGNE

A mixture of 4-methylene-1-oxaspiro[5.5]undecane, 4-methyl-1-oxaspiro[5.5]undec-3-ene and 4-methyl-1-oxaspiro[5.5]undec-4-ene prepared according to Example I is incorporated in a cologne at a concentration of 2.5% in 85% aqueous ethanol; and into a handkerchief perfume at a concentration of 20% (in 95% aqueous ethanol). A distinct and definite basil-like, eucalyptol-like fragrance containing a green and floral top notes is imparted to the cologne and to the handkerchief perfume.

EXAMPLE XXXVI

PREPARATION OF SOAP COMPOSITION

One hundred grams of soap chips are mixed with one gram of 4-methyl-1-oxaspiro(5.5) undecane prepared according to Example II until a substantially homogeneous composition is obtained. The perfumed soap composition exhibits a basil-like, herbaceous and eucalyptol-like aroma.

EXAMPLE XXXVII

PREPARATION OF A DETERGENT COMPOSITION

A total of 100 grams of a detergent powder is mixed with 0.15 grams of 4-methyl-1-oxaspiro(5.5) undecane prepared according to Example II until a substantially homogeneous composition is prepared. This composition exhibits a basil-like, herbaceous and eucalyptol-like aroma.

EXAMPLE XXXVIII

PREPARATION OF A COSMETIC POWDER COMPOSITION

A cosmetic powder is prepared by mixing in a ball mill, 100 grams of talcum powder with 0.25 grams of 4-methyl-1-oxaspiro(5.5) undecane prepared according to Example II. It has a basil-like, herbaceous and eucalyptol-like aroma.

EXAMPLE XXXIX

PERFUMED LIQUID DETERGENT

Concentrated liquid detergent with a herbaceous character is obtained containing 0.10%, 0.15% and 0.20% of 4-methyl-1-oxaspiro(5.5) undecane prepared according to Example II. It is prepared by adding and homogeneously mixing the appropriate quantity of 4-methyl-1-oxaspiro(5.5) undecane prepared according to Example II in the liquid detergent. The detergents all possess basil-like, herbaceous and eucalyptol-like notes, the intensity increasing with greater concentrations of 4-methyl-1-oxaspiro (5.5) undecane prepared according to Example II.

EXAMPLE XL

COLOGNE

4-Methyl-1-oxaspiro(5.5) undecane prepared according to Example II is incorporated in a cologne at a concentration of 2.5% in 85% aqueous ethanol; and into a handkerchief perfume at a concentration of 20%(in 95% aqueous ethanol). A distinct and definite herbaceous fragrance containing basil-like and eucalyptol-like notes is imparted to the cologne and to the handkerchief perfume.

EXAMPLE XLI

PREPARATION OF SOAP COMPOSITION

One hundred grams of soap chips are mixed with one gram of the mixture of 2,4-dimethyl-1-oxaspiro [5.5]undec-3-ene, 2,4-dimethyl-1-oxaspiro[5.5]undec4-ene and 2-methyl-4-methylene-1-oxaspiro[5.5] undecane prepared according to Example IV until a substantially homogeneous composition is obtained.

The perfumed soap composition exhibits a pleasant green, herbaceous, sweet oily, slightly minty aroma.

EXAMPLE XLII

PREPARATION OF A DETERGENT COMPOSITION

One hundred grams of soap chips are mixed with one gram of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV until a substantially homogeneous composition is obtained. The perfumed soap composition exhibits a pleasant green, herbaceous, sweet oily, slightly minty aroma.

A cosmetic powder is prepared by mixing in a ball mill, 100 grams of talcum powder with 0.25 grams of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV. It has a pleasant green, herbaceous, sweet oily, slightly minty aroma.

EXAMPLE XLIV

PERFUMED LIQUID DETERGENT

Concentrated liquid detergent with a herbaceous character is obtained containing 0.10%, 0.15% and 0.20% of the mixture of 2,4-dimethyl-1-oxaspiro[5.5] undec-3-ene, 2,4-demethyl-1-oxaspiro [5,5] undec-4-ene and 2-methyl-4-methylene-1-oxaspiro[5.5]undecane prepared according to Example IV. It is prepared by adding and homogeneously mixing the appropriate quantity of the mixture of 2,4-dimethyl-1-oxaspiro[5.5]undec3-ene, 2,4-dimethyl-1-oxaspiro[5.5]undec-4-ene and 2-methyl-4-methylene-1-oxaspiro[5.5]undecane prepared according to Example IV in the liquid detergent. The detergents will possess a green, herbaceous, sweet oily, slightly minty aroma, the intensity increasing with greater concentrations of the mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV.

EXAMPLE XLV

COLOGNE

The mixture of 2,4-dimethyl-1-oxaspiro[5.5]undec-3-ene, 2,4-dimethyl-1-oxaspiro[5.5]undec-4-ene and 2-methyl-4-methylene-1-oxaspiro[5.5]undecane prepared according to Example IV is incorporated in a cologne at a concentration of 2.5% in 85% aqueous ethanol; and into a handkerchief perfume at a concentration of 20% (in 95% aqueous ethanol). A distinct and definite herbaceous fragrance containing a sweet, minty and green top notes is imparted to the cologne and to the handkerchief perfume.

EXAMPLE XLVI

PREPARATION OF SOAP COMPOSITION

One hundred grams of soap chips are mixed with one gram of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII until a substantially homogeneous composition is obtained. The perfumed soap composition exhibits a pleasant green, floral, minty and terpineol-like aroma.

EXAMPLE XLVII

PREPARATION OF A DETERGENT COMPOSITION

A total of 100 grams of a detergent powder is mixed with 0.15 grams of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII until a substantially homogeneous composition is prepared. This composition exhibits a pleasant green, floral, minty and terpineol-like aroma.

EXAMPLE XLVIII

PREPARATION OF A COSMETIC POWDER COMPOSITION

A cosmetic powder is prepared by mixing in a ball mill, 100 grams of talcum powder with 0.25 grams of the mixture of 8,8,10-trimethyl-4-methylene1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII. It has a green, floral, minty and terpineol-like aroma.

EXAMPLE XLIX

PERFUMED LIQUID DETERGENT

Concentrated liquid detergent with a green, minty character is obtained containing 0.10%, 0.15% and 0.20% of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII. It is prepared by adding and homogeneously mixing the appropriate quantity of the mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII in the liquid detergent. The detergents all possess a green, floral, minty and terpineol-like aroma, the intensity increasing with greater concentrations of the mixture of 8,8,10-trimethyl-4-methylene-1-oxaspiro[5.5]undecane, 4,8,8,10-tetramethyl-1-oxaspiro[5.5]undec-3-ene 4,8,8,10-tetramethyl-1-oxaspiro[5.5]undec-4-ene prepared according to Example VII.

EXAMPLE L

COLOGNE

The mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5]undec-4-ene prepared according to Example VII is incorporated in a cologne at a concentration of 2.5% in 85% aqueous ethanol; and into a handkerchief perfume at a concentration of 20% (in 95% aqueous ethanol). A distinct and definite green, minty flower fragrance containing a terpineol-like top note is imparted to the cologne and to the handkerchief perfume.

EXAMPLE LI

PREPARATION OF MIXTURE OF

7-ISOPROPYL-10-METHYL-4-METHYLENE-1-OXASPIRO[5.5]UNDECANE, 7-ISOPROPYL-4,10-DIMETHYL-1-OXASPIRO[5.5]UNDEC-3-ENE AND 7-ISOPROPYL-4,10-DIMETHYL-1-OXASPIRO[5.5]UNDEC-4-ENE

Reaction:

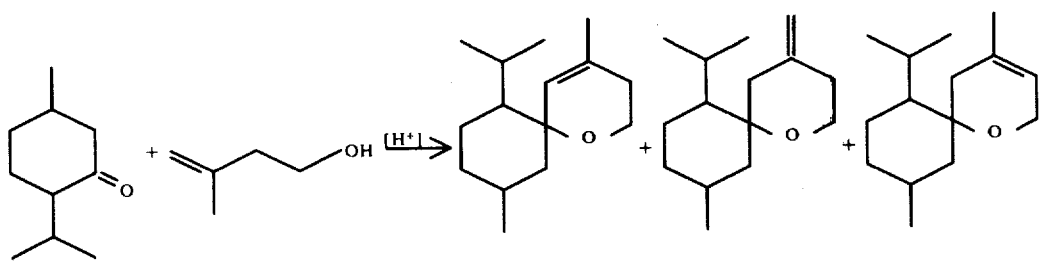

Into a 500 ml reaction flask equipped with stirrer, thermometer, reflux condenser, barrett trap and addition funnel is placed 154 g (1 mole) menthone, 75 ml cyclohexane and 1 g Ionol. The reaction mass is heated to reflux (105° C). At 10° C, 1 g concentrated sulfuric acid is added to 86 g (1 mole) of 3-methyl-3-buten-1-ol and the resulting mixture is added from the addition funnel to the reaction mass over a period of 10 minutes. The reaction mass is then maintained at reflux for a period of 27.5 hours. At the end of this period of time, 15 ml of water is collected. The reaction mass is cooled to room temperature and 2 g solid KOH flake is added thereto. The reaction mass is then rushed-over using 1 inch splash column at a vapor temperature of 111° C and a liquid temperature of 205° C at 2.9 mm Hg vacuum after adding thereto 10 g Primol.

The rushed-over material is then distilled using an 8 plate vigreux column after adding thereto 4.5 g Primol, 0.5 g triethanolamine and 1.0 g Ionox.

The fractional distillation data for the resulting reaction product is as follows:

| Fraction Number | Vapor Temperature | Liquid Temperature | Pressure (mm Hg) | Weight of Fraction | Reflux Ratio |
|---|---|---|---|---|---|
| 1 | 65–83° C | 107–112° C | 3.5 mm Hg | 2.8 g | 20:1 |
| 2 | 97° C | 113° C | 3.5 mm Hg | 2.1 g | 20:1 |
| 3 | 102° C | 115° C | 3.6 mm Hg | 2.0 g | 20:1 |
| 4 | 104° C | 118° C | 3.6 mm Hg | 6.2 g | 20:1 |
| 5 | 109° C | 135° C | 3.6 mm Hg | 6.1 g | 20:1 |
| 6 | 114° C | 147° C | 3.6 mm Hg | 7.5 g | 20:1 |
| 7 | 128° C | 250° C | 3.6 mm Hg | 4.6 g | 20:1 |

IR, NMR and Mass Spectral Analyses confirm that the composition of bulked fractions 2-7 consists of the following three compounds:

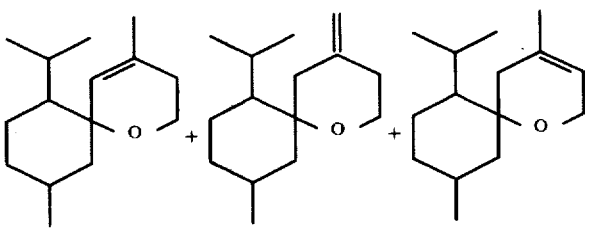

The NMR analysis for Fraction Number 5 is as follows:

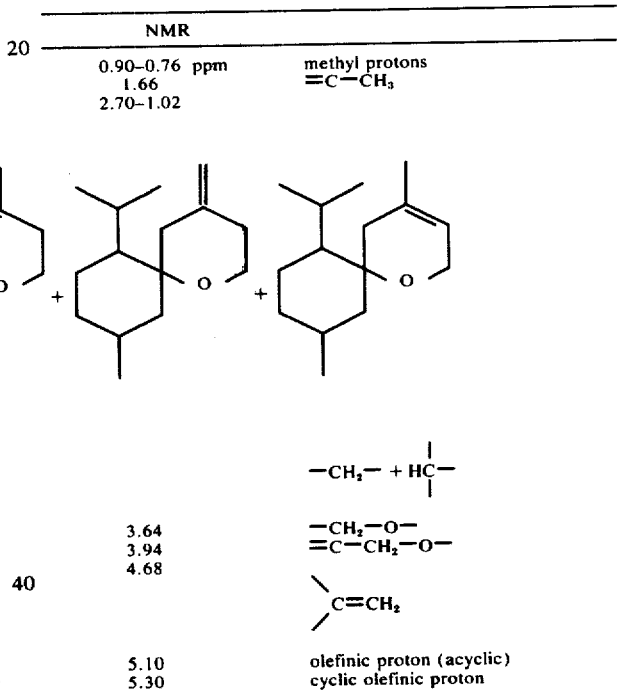

| NMR | |
|---|---|
| 0.90–0.76 ppm | methyl protons |
| 1.66 | =C—CH$_3$ |
| 2.70–1.02 | —CH$_2$— + HC— |
| 3.64 | —CH$_2$—O— |
| 3.94 | =C—CH$_2$—O— |
| 4.68 | \C=CH$_2$ / |
| 5.10 | olefinic proton (acyclic) |
| 5.30 | cyclic olefinic proton |

Figure 8:
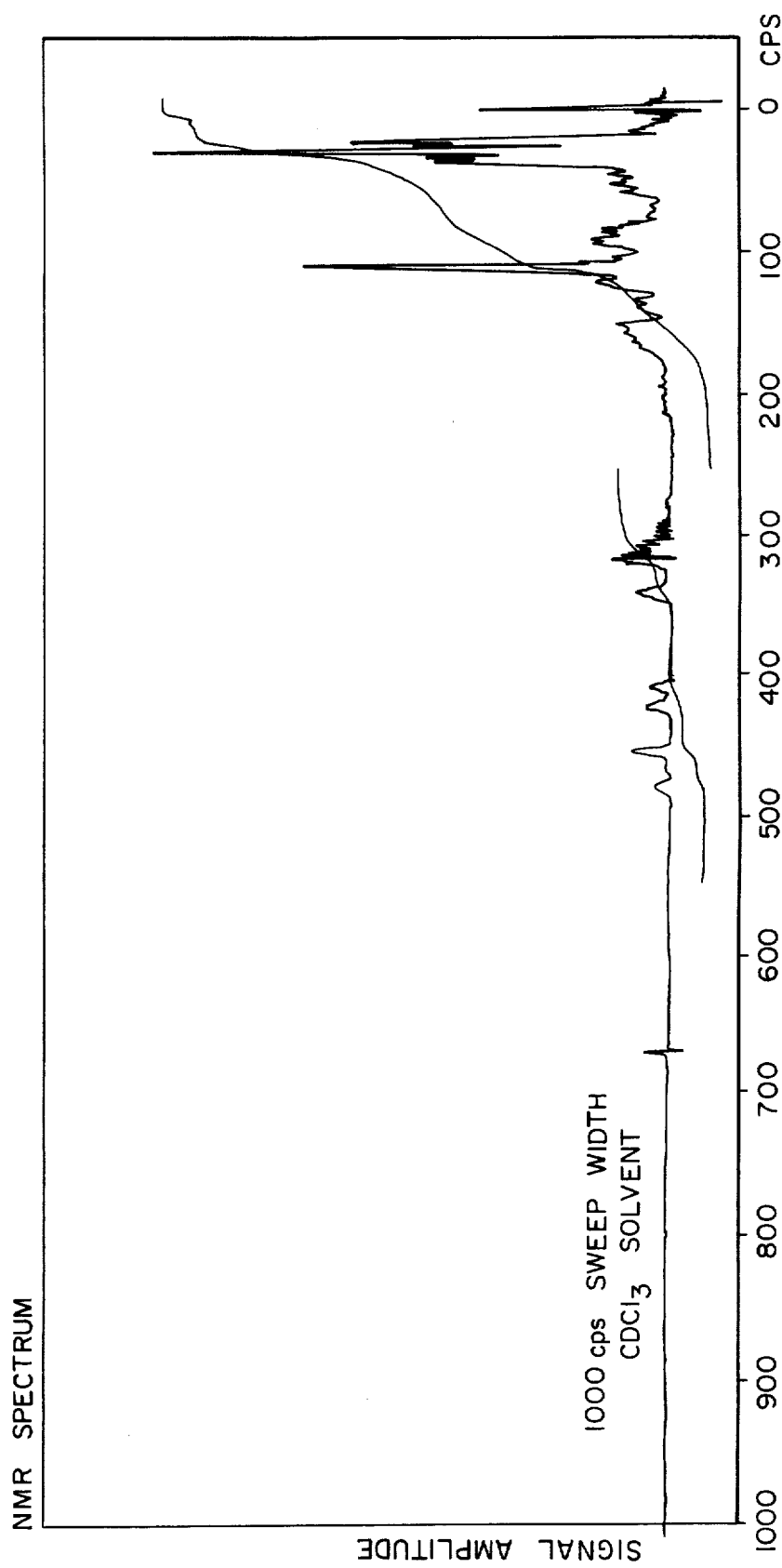
FIG. 8 is the nuclear magnetic resonance spectrum for Fraction 5 resulting from the fractional distillation of the product of Example LI, 7-isopropyl-10-methyl-4-methylene-1-oxaspiro[5.5]undecane, 7-isopropyl-4,10-dimethyl-1-oxaspiro[5.5]undec-3-ene and 7-isopropyl-4,10-dimethyl-1-oxaspiro[5.5]undec-4-ene.

The NMR spectrum for Fraction Number 5 is set forth in FIG. 8.

Figure 9:
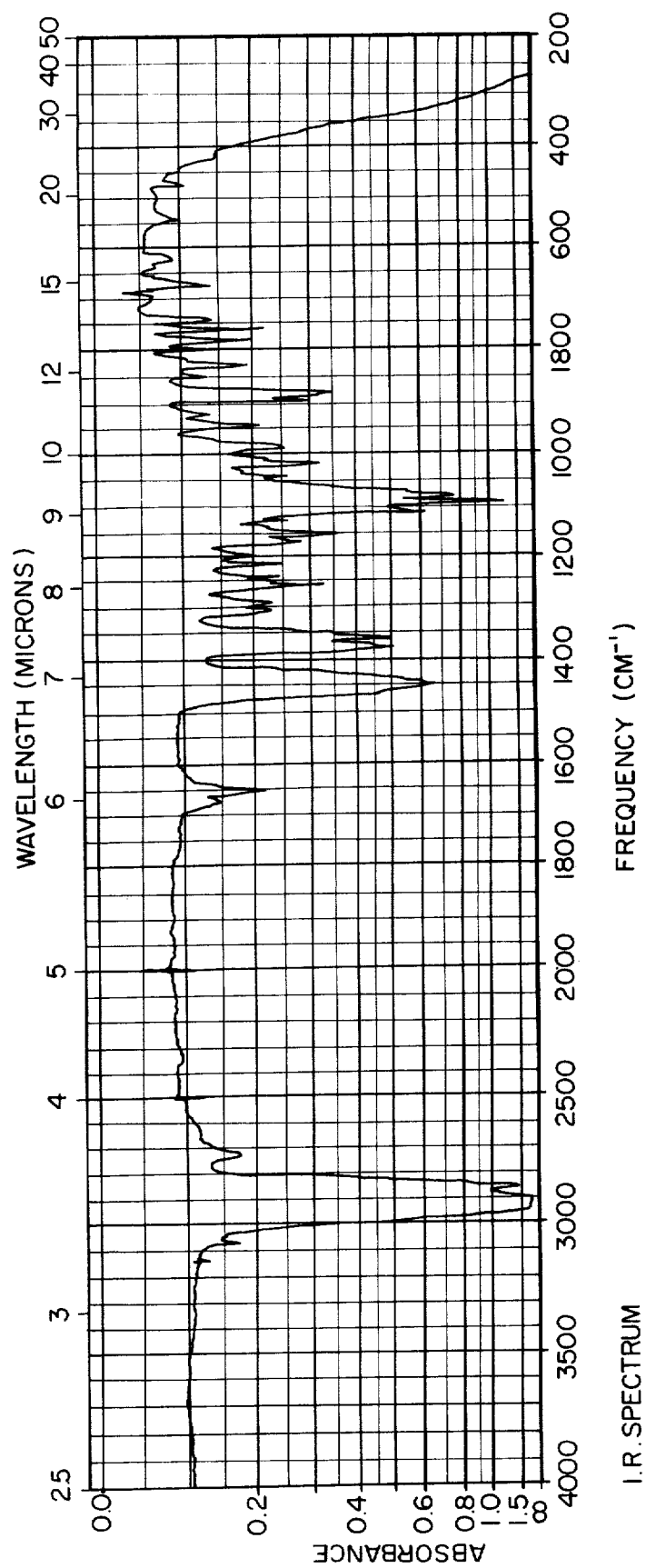
FIG. 9 is the infra-red spectrum for Fraction 5 resulting from the fractional distillation of the product of Example LI, the mixture of 7-isopropyl-10-methyl-4-methylene-1-oxaspiro[5.5]undecane, 7-isopropyl-4,10-dimethyl-1-oxaspiro[5.5]undec-3-ene and 7-isopropyl-4,10-dimethyl-1-oxaspiro[5.5]undec-4-ene.

The infra-red analysis for Fraction Number 5 is as follows: 880, 890, 1015, 1040, 1080, 1090, 1110, 1120, 1160, 1175, 1260, 1360, 1375, 1450, 2860, 2940 cm$^{-1}$ The infra-red spectrum for Fraction Number 5 of this mixture is set forth in FIG. 9.

The mass spectral analyses for Fraction Number 5 is as follows: (Molecular Ion, then in decreasing intensity): m/e = 222/137, 41, 69, 55, 222.

Fractions 4 and 5 are bulked and this bulked material, from a perfumery standpoint, has a minty, woody, cornmint note with a weedy topnote fragrance. Bulked Fractions 4 and 5 from a taste standpoint, have a damascenone-like, rosey, minty, aroma with floral, peach and tea nuances and a hay, tea, apple flavor with damascenone-like, cooling, spicy and astringent nuances.

EXAMPLE LII

PREPARATION OF 4,10-DIMETHYL-7-ISOPROPYL-1-OXASPIRO[5.5]UNDECANE

Reaction:

Into a 300 ml autoclave equipped with heating coil and shaker, the following materials are added:

| | |
|---|---|
| 5% Palladium on carbon catalyst | 0.15 gms. |
| Isopropyl alcohol | 9.2 gms. |
| Mixture of 7-isopropyl-10-methyl-4-methylene-1-oxaspiro[5.5]undecane, 7-isopropyl-4,10-dimethyl-1-oxaspiro[5.5]undec-3-ene and 7-isopropyl-4,10-dimethyl-1-oxaspiro[5.5]undec-4-ene produced according to Ex. LI | 7.5 gms. (0.03 moles) |

The autoclave is then pressurized with hydrogen gas over and operated at 100° C over a period of 3⅓ hours periodically repressurizing the autoclave to 50 psig.

The contents of the autoclave is then filtered and rushed-over. This rushed-over material is analyzed via GLC analysis yielding 5 peaks.

NMR, Mass Spectral and IR analyses yields the data that this material is primarily a compound having the structure:

NMR analysis is as follows:

| NMR | |
|---|---|
| 3.62 ppm (m) | —CH$_2$—O— |
| 2.50–1.20 | methylene and methine protons |
| 0.90 ppm | CH$_3$— (multiplicity of signals |

| NMR | |
|---|---|
| | due to isomeric forms) |

Figure 10:
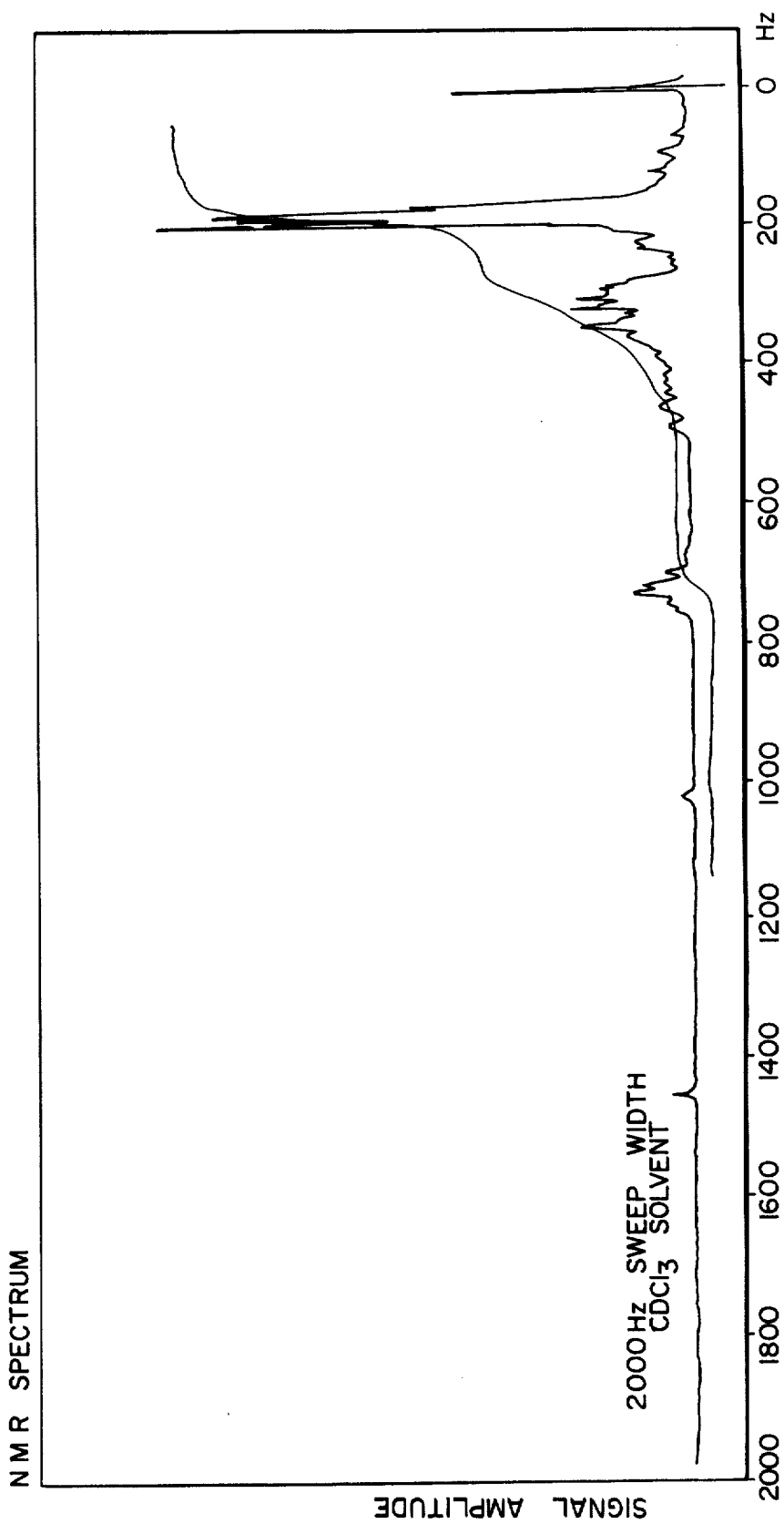
FIG. 10 is the nuclear magnetic resonance spectrum of the product of Example LII, 4,10-dimethyl-7-isopropyl-1-oxaspiro[5.5]undecane.

The NMR spectrum is set forth in FIG. 10.

The mass spectral analyses is as follows: m/e = 222/137, 41, 69, 222, 55, 43.

The subject material has a sweet, delicate rose, dried fruit, winey, apple, fruit aroma and sweet, apple, delicate rosey, juicey, dried fruit, yeasty and winey flavor insofar as its taste is concerned. This material also has a low-keyed, sweet, floral, fruity aroma insofar as its usefulness in perfumery is concerned.

EXAMPLE LIII

USE IN FLAVOR FORMULATION OF 7-ISOPROPYL-10-METHYL-4-METHYLENE-1-OXASPIRO[5.5]UNDECANE, 7-ISOPROPYL-4-10-DIMETHYL-1-OXASPIRO[5.5]UNDEC-3-ENE AND 7-ISOPROPYL-4,10-DIMETHYL-1-OXASPIRO[5.5]UNDEC-4-ENE

The following basic raspberry flavor formulation is produced by admixing the indicated ingredients:

| Ingredient | Parts by Weight |
|---|---|
| Vanillin | 2 |
| Maltol | 4 |
| Parahydroxybenzylacetone | 5 |
| Alpha-ionone (10% in propylene glycol) | 2 |
| Ethylbutyrate | 6 |
| Ethylacetate | 16 |
| Dimethyl sulfide | 1 |
| Isobutyl acetate | 14 |
| Acetic acid | 10 |
| Acetaldehyde | 10 |
| Propylene glycol | 930 |

To a portion of the foregoing formulation, 3% by weight of said formulation of the mixture of compounds, 7-isopropyl-10-methyl-4-methylene-1-oxaspiro[5.5]undecane, 7-isopropyl-4,10-dimethyl-1-oxaspiro[5.5]undec-3-ene and 7-isopropyl-4,10-dimethyl-10-oxaspiro[5.5]undec-4-ene of Example LI are added, and the flavor of the formulation containing such mixture and not containing such mixture are compared in water at the rate of 100 ppm.

The aroma topnotes and the taste of ripe raspberries, has a sweet, delicate rose reminiscent characteristic are present in the formulation containing the mixture of 7-isopropyl-10-methyl-4-methylene-1-oxaspiro[5.5]undecane, 7-isopropyl-4,10-dimethyl-10-oxaspiro[5.5]undec-4-ene. Therefore, the modified formulation with said mixture is preferred by all members of a blind taste panel. The formulation giving rise to a more natural-like raspberry flavor.

EXAMPLE LIV

Preparation of Reaction Product of Dihydro Verdyl Ketone and 3-Methyl-3-Buten-1-Ol Reaction:

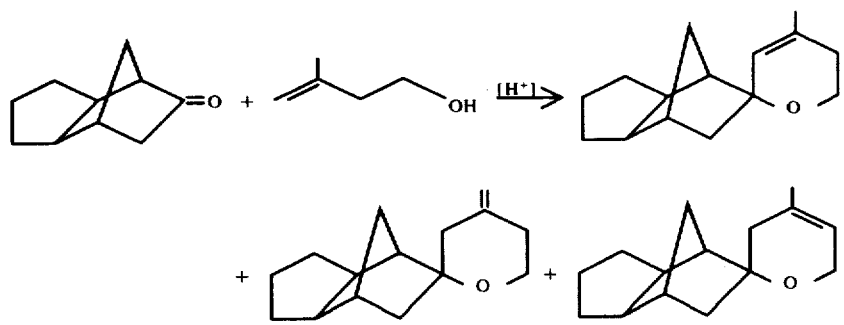

Into a 500 ml round bottom flask equipped with stirrer, condenser, addition funnel thermometer, Barrett Trap and heating mantel are placed the following ingredients:

| Ingredient | Parts by Weight |
| --- | --- |
| Dihydro-verdyl ketone having the structure: | 45 g (0.3 moles) |

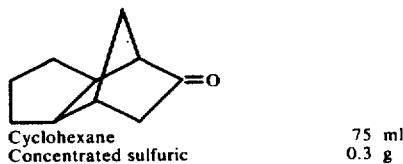

| Ingredient | Parts by Weight |
| --- | --- |
| Cyclohexane | 75 ml |
| Concentrated sulfuric acid | 0.3 g |

The resulting mixture is heated to reflux (86° C) and while this mixture is refluxing, 3-methyl-3-buten-1-ol is added dropwise with stirring over a 20 minute period, during which time the reaction temperature rises to 89° C. Refluxing is continuted until 6 ml of water is collected in the Barrett Trap. The reaction mass is then cooled to room temperature and 1 g of 50% sodium hydroxide is added thereto. The reaction mass is then rushed-over on a 2 inch splash column after adding thereto 5 g Primol. The rushed-over is at the following conditions:

| Fraction Number | Vapor Temperature | Liquid Temperature | Pressure (mm Hg) | Weight of Fraction |
| --- | --- | --- | --- | --- |
| 1 | 82–98° C | 110–123° C | 3.3–3.5 mm Hg | 8.0 g |
| 2 | 120° C | 135° C | 3.5 mm Hg | 9.2 g |
| 3 | 129° C | 149° C | 3.4 mm Hg | 16.7 g |
| 4 | 140° C | 192° C | 3.2 mm Hg | 12.9 g |
| 5 | 110° C | 203° C | 3.4 mm Hg | 2.4 g |

The rushed-over material is then admixed with 4.5 g Primol, 0.5 g of triethanolamine and 0.1 g Ionox. The resulting mixture is fractionated on a 8 plate vigreux column. The fractional distillation data for the resulting product is as follows:

| Fraction Number | Vapor Temperature | Liquid Temperature | Pressure (mm Hg) | Weight of Fraction | Reflux Ratio |
| --- | --- | --- | --- | --- | --- |
| 1 | 82–122° C | 132–137° C | 2.9–3.1 mm Hg | 6.6 | 20:1 |
| 2 | 122° C | 138° C | 3.0 mm Hg | 3.5 | 20:1 |
| 3 | 123° C | 139° C | 3.1 mm Hg | 3.0 | 20:1 |
| 4 | 123° C | 140° C | 3.1 mm Hg | 3.5 | 20:1 |
| 5 | 125° C | 141° C | 3.0 mm Hg | 3.1 | 20:1 |
| 6 | 125° C | 145° C | 3.0 mm Hg | 4.9 | 20:1 |
| 7 | 125° C | 160° C | 3.0 mm Hg | 4.7 | 20:1 |
| 8 | 125° C | 179° C | 3.0 mm Hg | 3.2 | 20:1 |
| 9 | 129° C | 191° C | 3.0 mm Hg | 3.6 | 20:1 |
| 10 | 139° C | 207° C | 3.0 mm Hg | 1.7 | 20:1 |

IR, NMR and Mass Spectral analyses confirm that the composition of bulked fractions 4-8 consists of the following three compounds:

The infra-red analysis for Fraction Numer 7 is as follows: 875, 1075, 1095, 1140, 1370, 1440, 1470, 2860, 2940 cm$^{-1}$.

Figure 11:
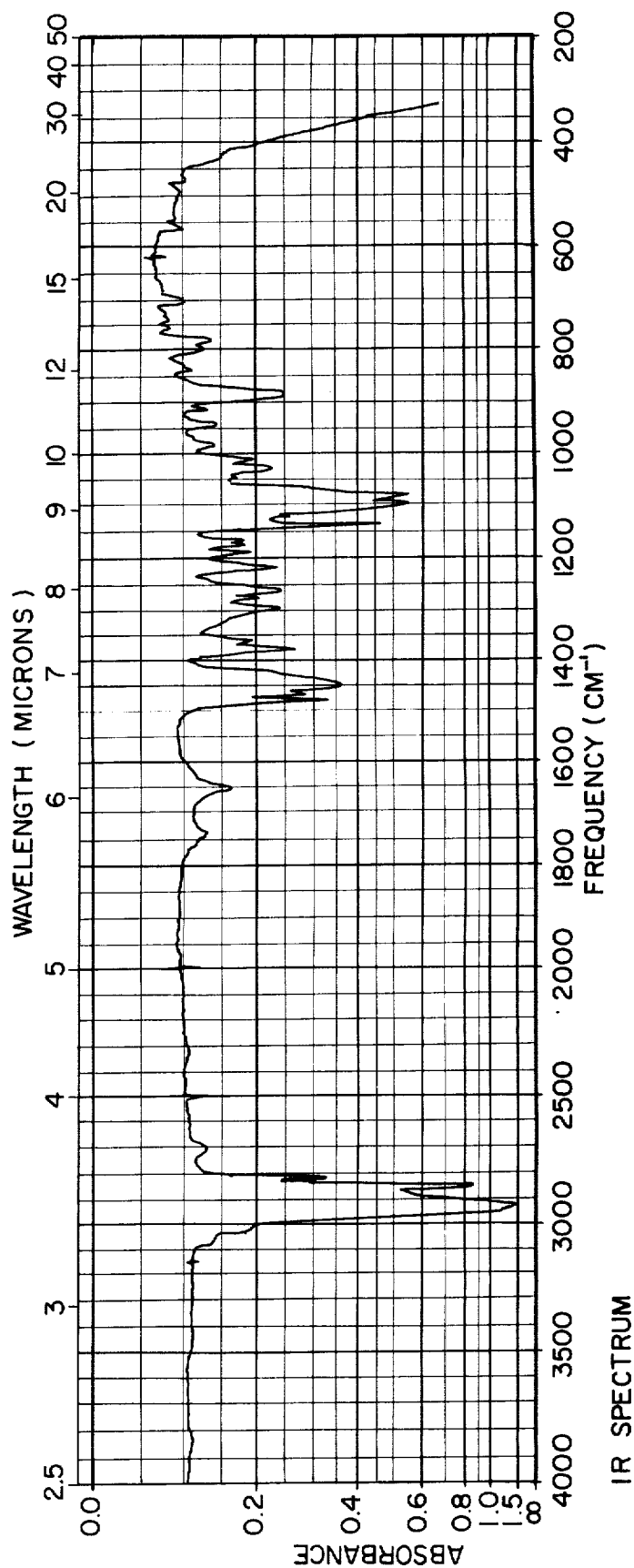
FIG. 11 is the infra-red spectrum for Fraction 4 resulting from the fractional distillation of the product of Example LIV, the reaction product of dihydro verdyl ketone and 3-methyl-3-buten-1-ol.

The infra-red spectrum for Fraction Number 4 of this mixture is set forth in FIG. 11.

The NMR analysis for Fraction Number 4 is as follows:

| NMR | |
|---|---|
| 5.40 ppm (m) | H C=C— |
| (i) | |
| 4.70 (d) | C=C $\begin{smallmatrix}H\\H\end{smallmatrix}$ |
| 3.90 (m) | =C—CH$_2$—O— |
| 3.70 (t) | —CH$_2$—O— |
| 2.60 – 0.70 (m) | methylene and methine protons |
| 1.60 (broadsinglet) | =C—CH$_3$— |

Figure 12:
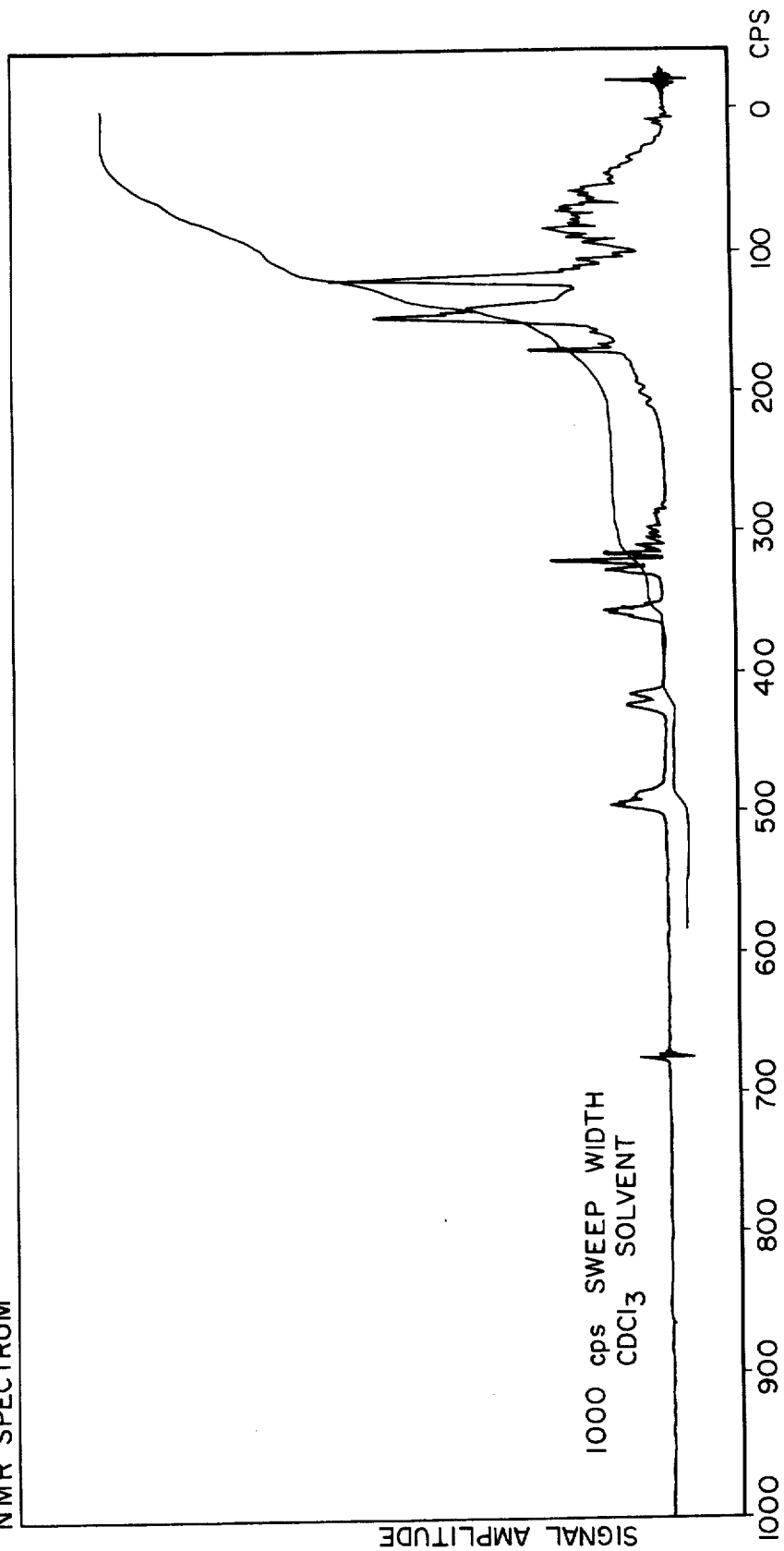
FIG. 12 is the nuclear magnetic resonance spectrum for Fraction 7 resulting from the fractional distillation of the product of Example LIV, the reaction product of dihydro verdyl ketone and 3-methyl-3-buten-1-ol.

The NMR spectrum for Fraction Number 7 is set forth in FIG. 12.

The Mass Spectral analysis for Fraction Number 7 is as follows: (Molecular Ion, then in decreasing intensity): m/e = 218/110, 149, 79, 67, 53, 95, 203.

Bulked Fraction Number 4–8 insofar as its perfumery use is concerned, has a green, floral, woody aroma with fruity and tomato nuances. Insofar as its taste characteristics are concerned, bulked Fractions Number 4–8 has a green, weedy aroma with green, weedy and fatty flavor characteristics at a concentration of 0.1 ppm.

EXAMPLE LV

Preparation of Reaction Product of Verdyl Ketone and 3-Methyl-3-Buten-1-ol

Reactions:

(ii)

Into a 500 ml round bottom flask equipped with stirrer, condenser, addition funnel, thermometer, Barrett Trap and heating mantel, the following materials are placed:

| | |
|---|---|
| Verdyl Ketone, a mixture of compounds having the structures: | 109 g (0.736 moles) |

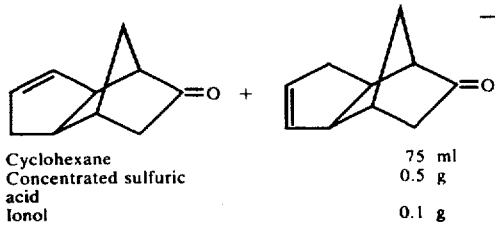

| Cyclohexane | 75 ml |
|---|---|
| Concentrated sulfuric acid | 0.5 g |
| Ionol | 0.1 g |

The resulting mixture is heated to reflux (93° C) and while at reflux 64 g (0.74 moles) of 3-methyl-3buten-1-ol is added dropwise with stirring thereto over a 30 minute period, during which time the reflux temperature rises to 95° C. The reaction mass is heated for a period of 12 hours, during which time 12 ml of water is collected. At the end of this time, the reaction mass is cooled to room temperature and 1 g of a 50% aqueous sodium hydroxide solution is added thereto.

The reaction mass is then rushed-over using a 2 inch splash column after adding thereto 5 g of Primol and 0.1 g Ionox. The rushed-over distillation data is as follows:

| Fraction Number | Vapor Temperature | Liquid Temperature | Pressure (mm Hg) | Weight of Fraction |
|---|---|---|---|---|
| 1 | 23-35° C | 40-105° C | 100 mm Hg | 87.9 |
| 2 | 111° C | 135° C | 3.0 mm Hg | 61.1 |
| 3 | 121° C | 145° C | 2.9 mm Hg | 34.8 |
| 4 | 164° C | 215° C | 2.9 mm Hg | 33.4 |

The resulting material is then fractionated using an 8 plate vigreux column after adding thereto 4.5 g Primol, 0.5 g triethanolamine and 0.1 g Ionox.

The fractional distillation data for the resulting product is as follows:

| Fraction Number | Vapor Temperature | Liquid Temperature | Pressure (mm Hg) | Weight of Fraction | Reflux Ratio |
|---|---|---|---|---|---|
| 1 | 51-78° C | 98-116° C | 2.9-2.5 mm Hg | 18.1 | 20:1 |
| 2 | 79° C | 137° C | 2.9 mm Hg | 25.2 | 20:1 |
| 3 | 117° C | 140° C | 2.7 mm Hg | 7.6 | 20:1 |
| 4 | 118° C | 142° C | 2.7 mm Hg | 8.2 | 20:1 |
| 5 | 118° | 149° C | 2.7 mm Hg | 8.6 | 20:1 |
| 6 | 120° C | 161° C | 2.7 mm Hg | 9.0 | 20:1 |
| 7 | 121° C | 167° C | 2.7 mm Hg | 10.4 | 20:1 |
| 8 | 122° C | 178° C | 2.7 mm Hg | 10.2 | 20:1 |
| 9 | 124° C | 184° C | 2.7 mm Hg | 8.0 | 20:1 |
| 10 | 124° C | 191° C | 2.7 mm Hg | 7.2 | 20:1 |
| 11 | 133° C | 228° C | 2.7 mm Hg | 4.1 | 20:1 |

IR, NMR and Mass Spectral analyses confirm that the composition of bulked Fractions Number 5-10 consists of the following six compounds:

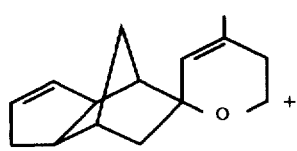 + 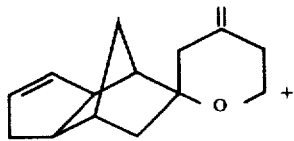 + 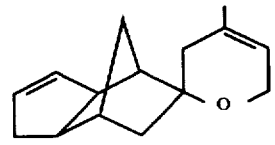

and

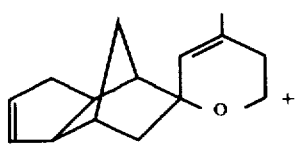 + 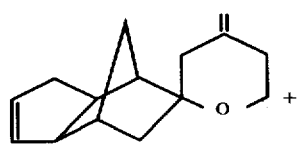 + 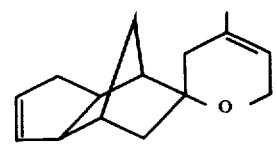

Figure 13:
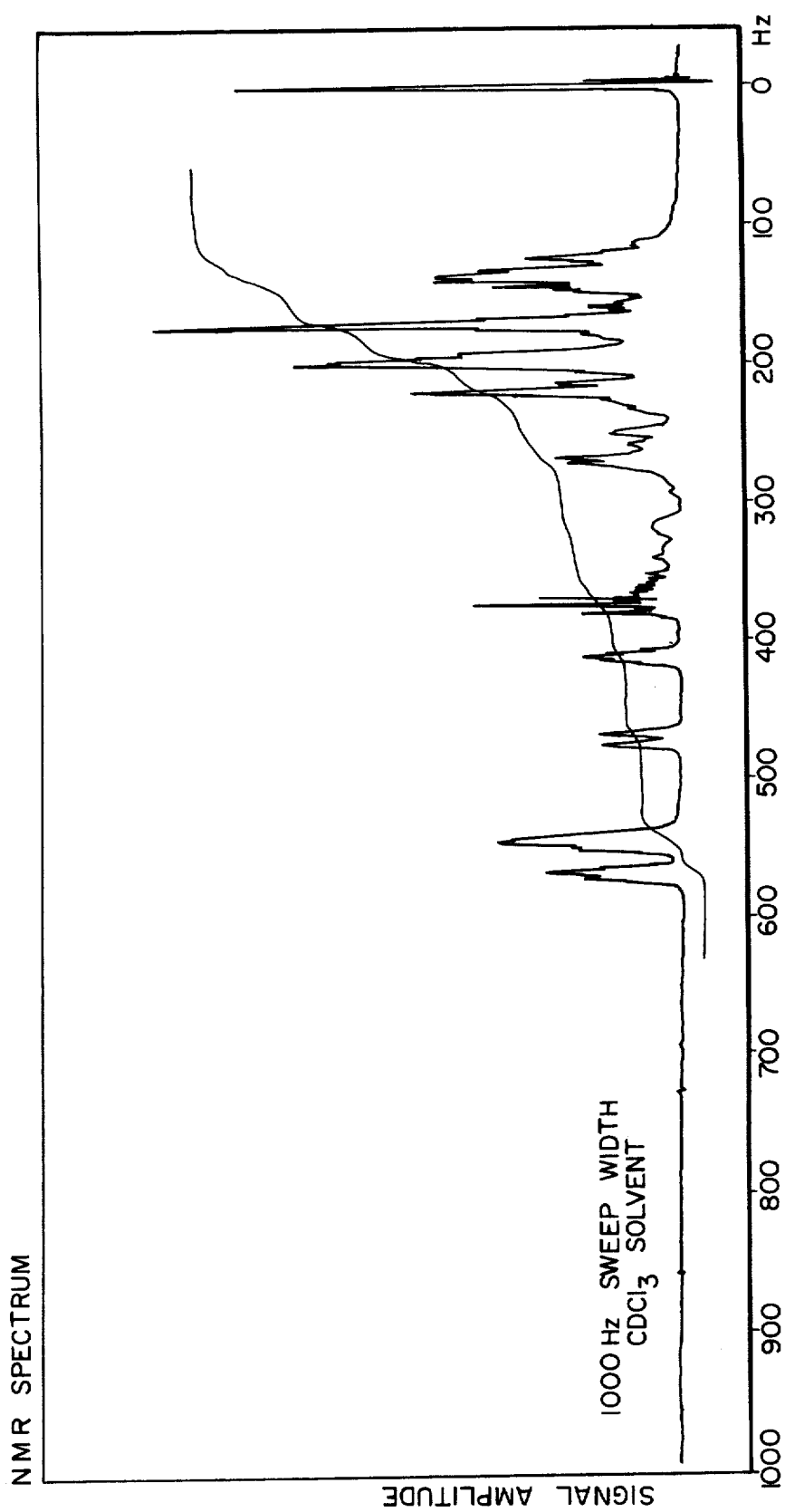
FIG. 13 is the nuclear magnetic resonance spectrum for Fraction 3 resulting from the fractional distillation of the product of Example LV, the reaction product of verdyl ketone and 3-methyl-3-buten-1-ol.

The NMR spectrum for Fraction Number 3 is set forth in FIG. 13.

Figure 14:
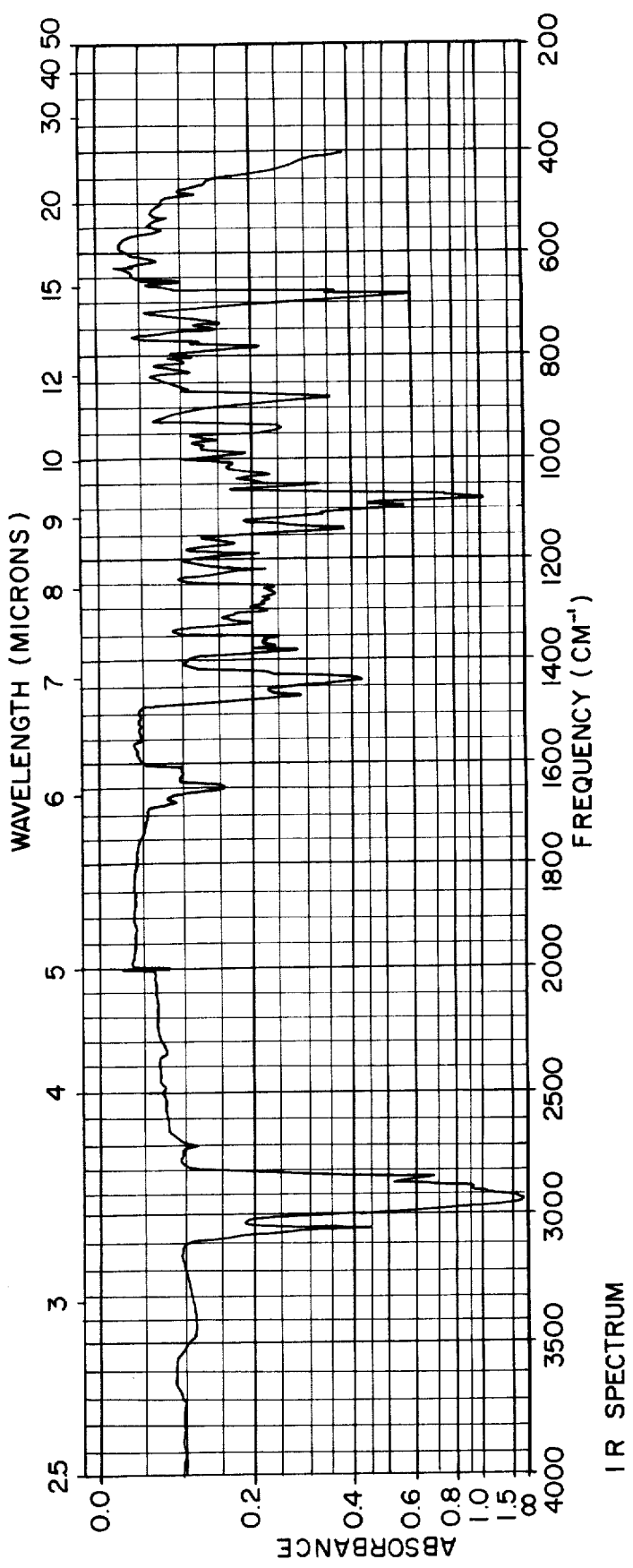
FIG. 14 is the infra-red spectrum for Fraction 3 resulting from the fractional distillation of the product of Example LV, the reaction product of verdyl ketone and 3-methyl-3-buten-1-ol.

The infra-red spectrum for Fraction Number 3 is set forth in FIG. 14.

The mass Spectral analysis for Fraction Number 3 is as follows: (Molecular Ion, then in decreasing intensity): m/e = 216/39, 216, 41, 149, 106, 67.

Bulked Fractions Number 5-10, from a perfumery standpoint, has a green, floral, mushroomy, rich fragrance with an underlying borneol note. Bulked Fractions Number 5-10 from a taste standpoint, has a weedy, green aroma, and a fatty, green, weedy flavor at 0.05 ppm.

EXAMPLE LVI

PRODUCT PRODUCED BY REACTION OF BETA-DECALONE AND 3-METHYL3-BUTEN-1-OL

Reaction:

stripped of solvent and rushedover using a 2 inch splash column. The resulting material is then fractionated using an 8 inch vigreux column after adding thereto 10.0 g of Primol and 0.1 ionox. The fractional distillation data for the resulting reaction product is as follows:

| Fraction Number | Vapor Temperature | Liquid Temperature | Pressure (mm Hg) | Weight of Fraction | Reflux Ratio |
|---|---|---|---|---|---|
| 1 | 83–86° C | 127–129° C | 2.8–3.2 mm Hg | 15.5 | 9:1 |
| 2 | 105° C | 116° C | 3.0 mm Hg | 16.5 | 9:1 |
| 3 | 119° C | 146° C | 3.0 mm Hg | 5.9 | 9:1 |
| 4 | 119° C | 146° C | 3.0 mm Hg | 12.3 | 9:1 |
| 5 | 120° C | 146° C | 3.0 mm Hg | 13.4 | 9:1 |
| 6 | 121° C | 146° C | 3.0 mm Hg | 15.6 | 9:1 |
| 7 | 122–123C | 145–151° C | 2.5 mm Hg | 26.5 | 9:1 |
| 8 | 124° C | 151° C | 2.5 mm Hg | 24.6 | 9:1 |
| 9 | 124° C | 152° C | 2.5 mm Hg | 24.8 | 9:1 |
| 10 | 124° C | 152° C | 2.5 mm Hg | 20.9 | 4:1 |
| 11 | 124° C | 154° C | 2.5 mm Hg | 31.2 | 4:1 |
| 12 | 124° C | 156° C | 2.5 mm Hg | 28.2 | 4:1 |
| 13 | 124° C | 181° C | 2.5 mm Hg | 30.3 | 4:1 |
| 14 | 124° C | 205° C | 2.5 mm Hg | 16.5 | 4:1 |
| 15 | 122° C | 220° C | 2.5 mm Hg | 3.0 | 4:1 |

Fractions Number 8–15 are bulked.

IR, NMR and Mass Spectral analyses confirm that the composition of the bulked Fractions Number 8–15 consists of the following 3 compounds:

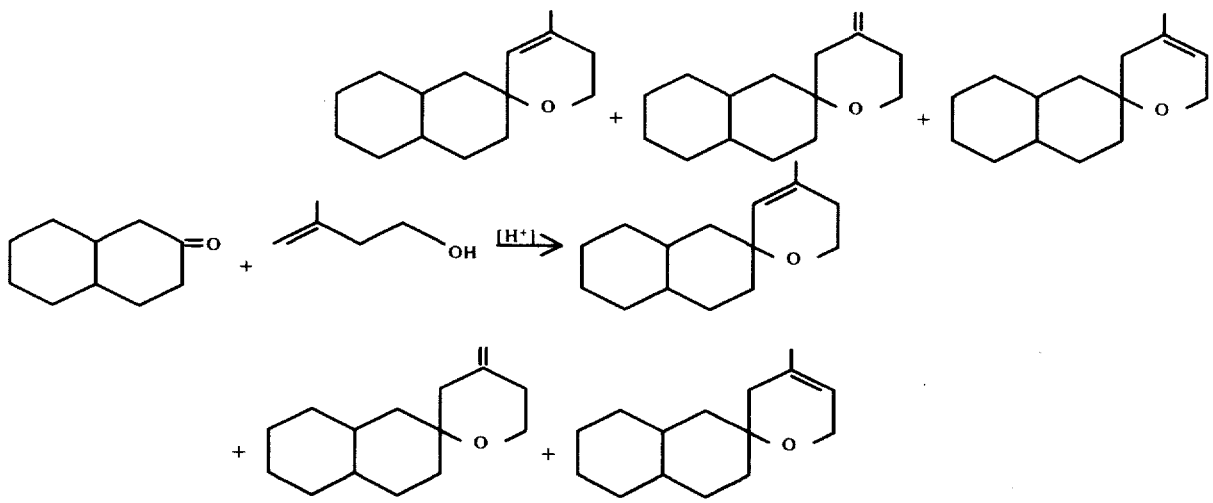

Into a 1-liter round bottom flask equipped with stirrer, thermometer, reflux condenser, addition funnel and Barrett Trap the following materials are placed:

| | |
|---|---|
| Beta-decalone | 309 g (2 moles) |
| Concentrated Sulfuric Acid | 1 g |
| Ionol | 0.1 g |
| Cyclohexane | 100 ml |

Figure 15:
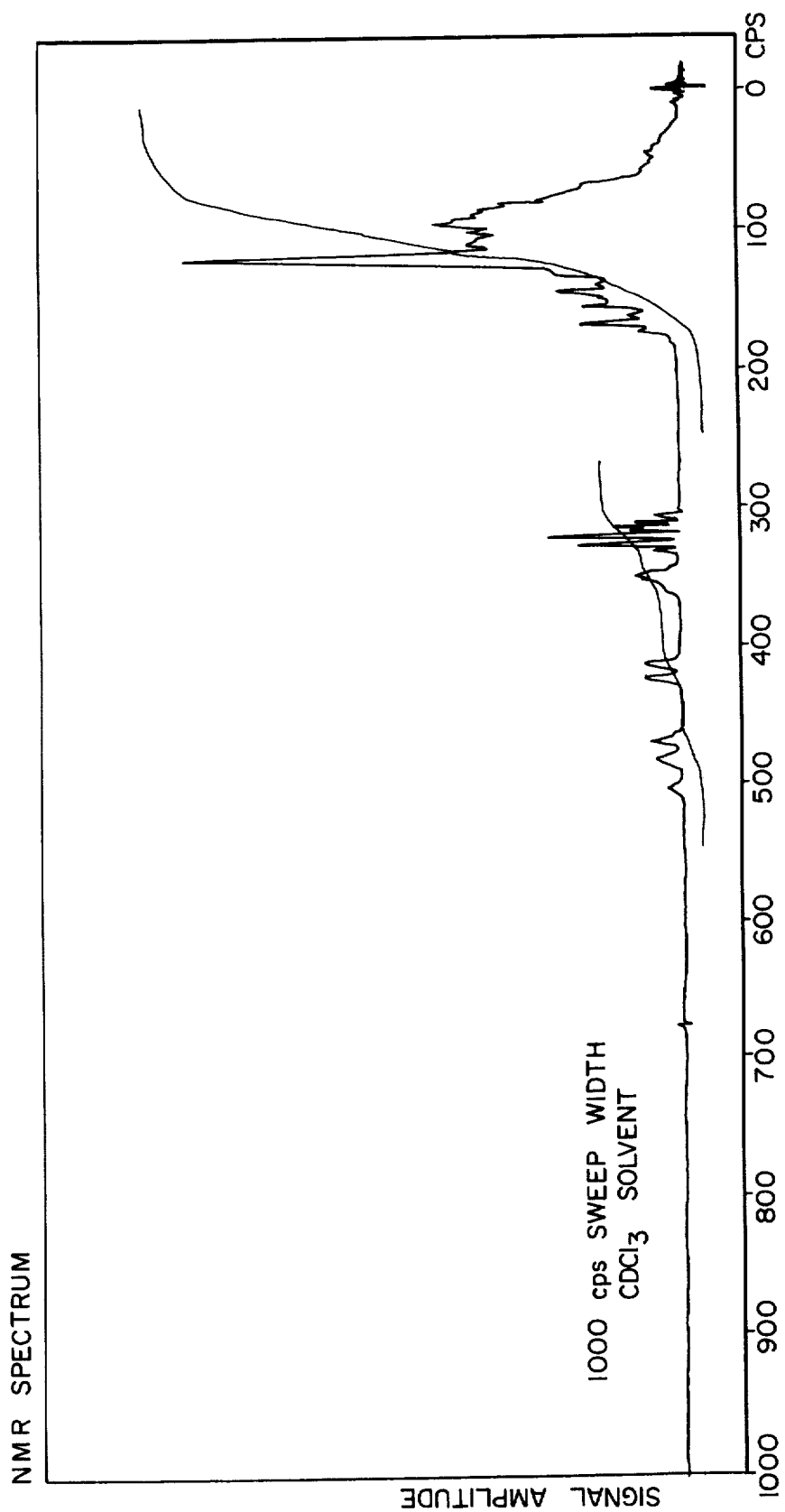
FIG. 15 is the nuclear magnetic resonance spectrum for the material of Fraction 9 resulting from the fractional distillation of the product of Example LVI, the reaction product of beta-decalone and 3-methyl-3-buten-1-ol.
Figure 16:
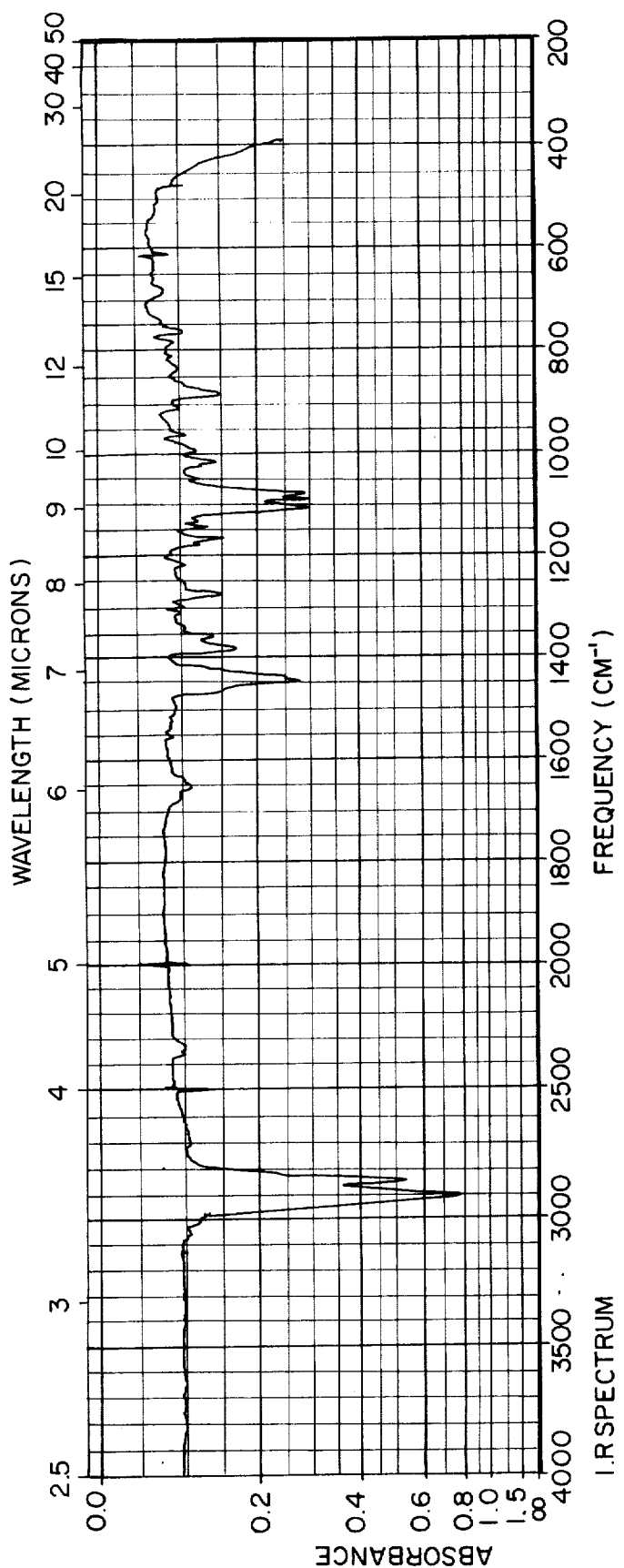
FIG. 16 is the infra-red spectrum for Fraction 9 resulting from the fractional distillation of the product of Example LVI, the reaction product of beta-decalone and 3-methyl-3-buten-1-ol.

The resulting mixture is heated to reflux and over a 2¼ hour period, while maintaining reflux, 172 g (1 mole) of 3-methyl-3- buten-1-ol is added to the reaction mass from the addition funnel. Refluxing is then continued for another 11½ hours, after which period of time the reaction mass is cooled to room temperature. 2 g of a 50% aqueous sodium hydroxide solution is then added and the resulting crude reaction product is The NMR spectrum for the material of Fraction Number 9 is set forth in FIG. 15.

The infra-red spectrum for Fraction Number 9 is set forth in FIG. Number 16.

The mass spectral analysis for Fraction Number 9 is as follows: (Molecular Ion, then in decreasing intensity): m/e = 220/123, 110, 68, 67, 111, 220.

Bulked Fractions Number 8–15 from a taste standpoint has a weedy, green aroma character and a weedy, green, fatty, sweet flavor character at 5 ppm.

EXAMPLE LVII

PREPARATION OF 9-T-BUTYL-4-METHYL-1-OXASPIRO[5.5]UNDECANE

Reaction:

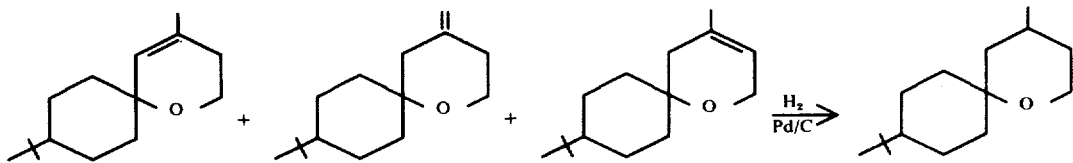

Into a Parr Shaker the following materials are placed:

| | |
|---|---|
| Mixture of 9-t-butyl-4-methylene-1-oxaspiro[5.5]undecane, 9-t-butyl-4-methyl-1-oxspiro[5.5]undec-3-ene and 9-t-butyl-4-methyl-1-oxaspiro[5.5]undec-ene prepared according to Example IX (bulked Fractions Number 5-14) | 111 g (0.5 moles) |
| 5% Palladium on carbon catalyst | 1 g |
| Isopropyl alcohol | 150 ml |

The Parr Shaker is then pressurized with hydrogen gas and operated at 100° C over a period of 21 hours. The contents of the Parr Shaker is then dissolved in 175 ml of ethanol using heating to reflux. The product of reaction then precipitates from the solution at 35° C. The ethanol-product slurry is then filtered and the precipitate, white crystals is then analysed using mass spectral, NMR and IR analyses. Mass spectral, NMR and IR analyses yield the information that the product is a compound having the structure:

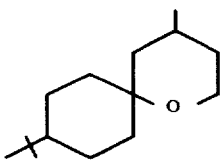

Figure 17:
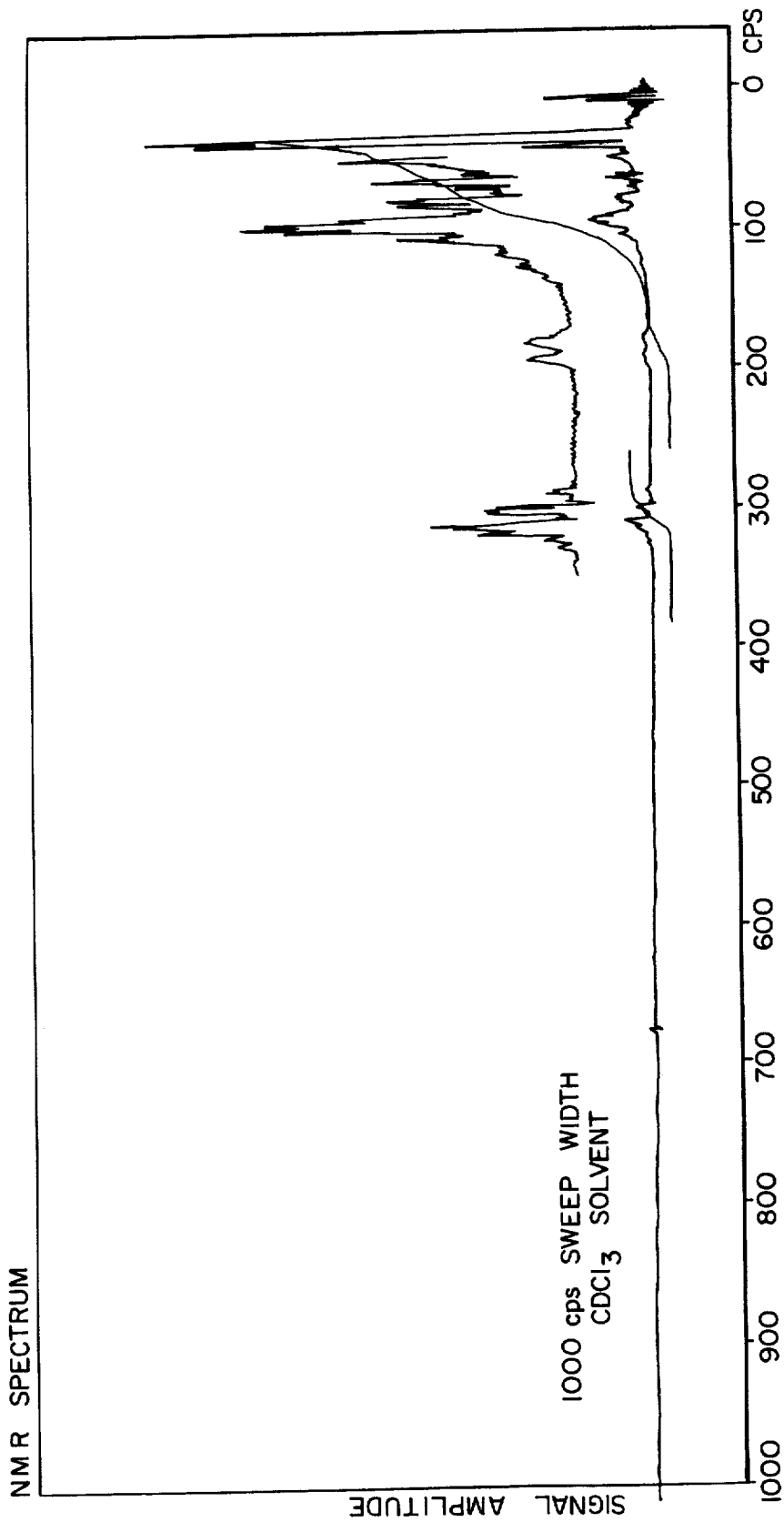
FIG. 17 is the nuclear magnetic resonance spectrum for the product of Example LVII, 9-t-butyl-4-methyl-1-oxaspiro[5.5]undecane.

The NMR spectrum for this product is set forth in FIG. 17.

Figure 18:
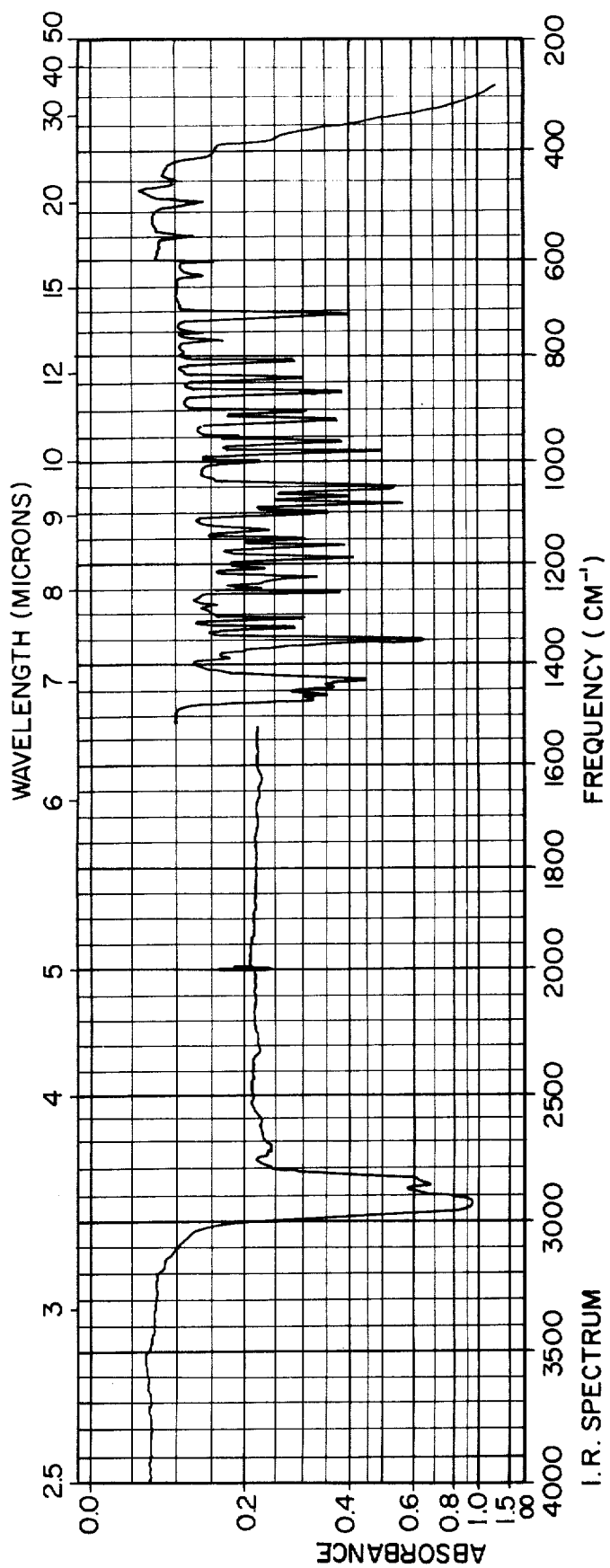
FIG. 18 is the infra-red spectrum for the product of Example LVII, 9-t-butyl-4-methyl-1-oxaspiro[5.5]undecane.

The infra-red spectrum for this product is set forth in FIG. 18.

Mass spectral data is as follows: (Molecular Ion, then in decreasing intensity): m/e = 224/125, 41, 55, 112, 57

The product insofar as its perfumery use is concerned, has a low-keyed floral, woody aroma reminiscent of hexenyl salicylate and also has buttery, sulfurous notes.

Insofar as its flavor is concerned, the resulting product has a green, floral, methyl salicyclate aroma and a methyl salicyclate-type, green, floral flavor with phenolic and astringent notes.

EXAMPLE LVIII

PREPARATION OF 4,8,8,10-TETRAMETHYL1-OXASPIRO[5.5] UNDECANE

Reaction:

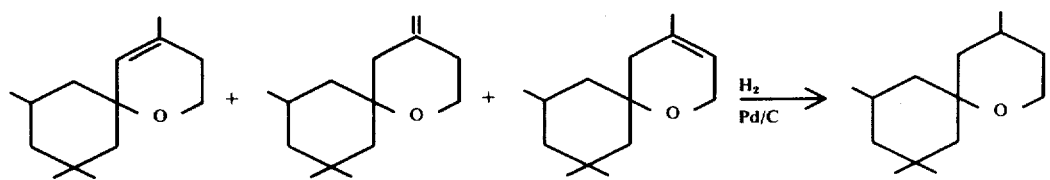

Into a Parr Shaker the following materials are placed:

| | |
|---|---|
| Mixture of 8,8,10-trimethyl-4-methylene-1-oxaspiro[5.5]undecane, 4,8,8,10-tetramethyl-1-oxaspiro[5.5]undec-3-ene and 4,8,8,10-tetramethyl-1-oxaspiro[5.5.]undec-4-ene prepared according to Example VII (Fraction Number 13) | 4.16 g (0.02 moles) |
| Isopropyl alcohol | 4 g |
| 5% Palladium on carbon catalyst | 0.04 g |

The Parr Shaker is pressurized with hydrogen gas and operated for a period of 13⅓ hours at 100° C, periodically repressurizing the Parr Shaker with hydrogen gas.

The contents of the Parr Shaker is then filtered and the filtrate is distilled through Bantamware distillation apparatus at 94°–95° C and 5.2 mm Hg pressure, yielding 3.3 g of product which has the structure:

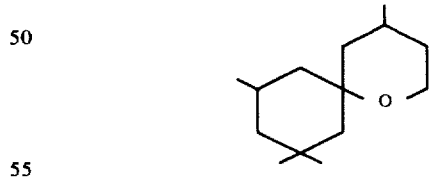

as confirmed by GLC, Mass Spectral, NMR and IR analyses.

Figure 19:
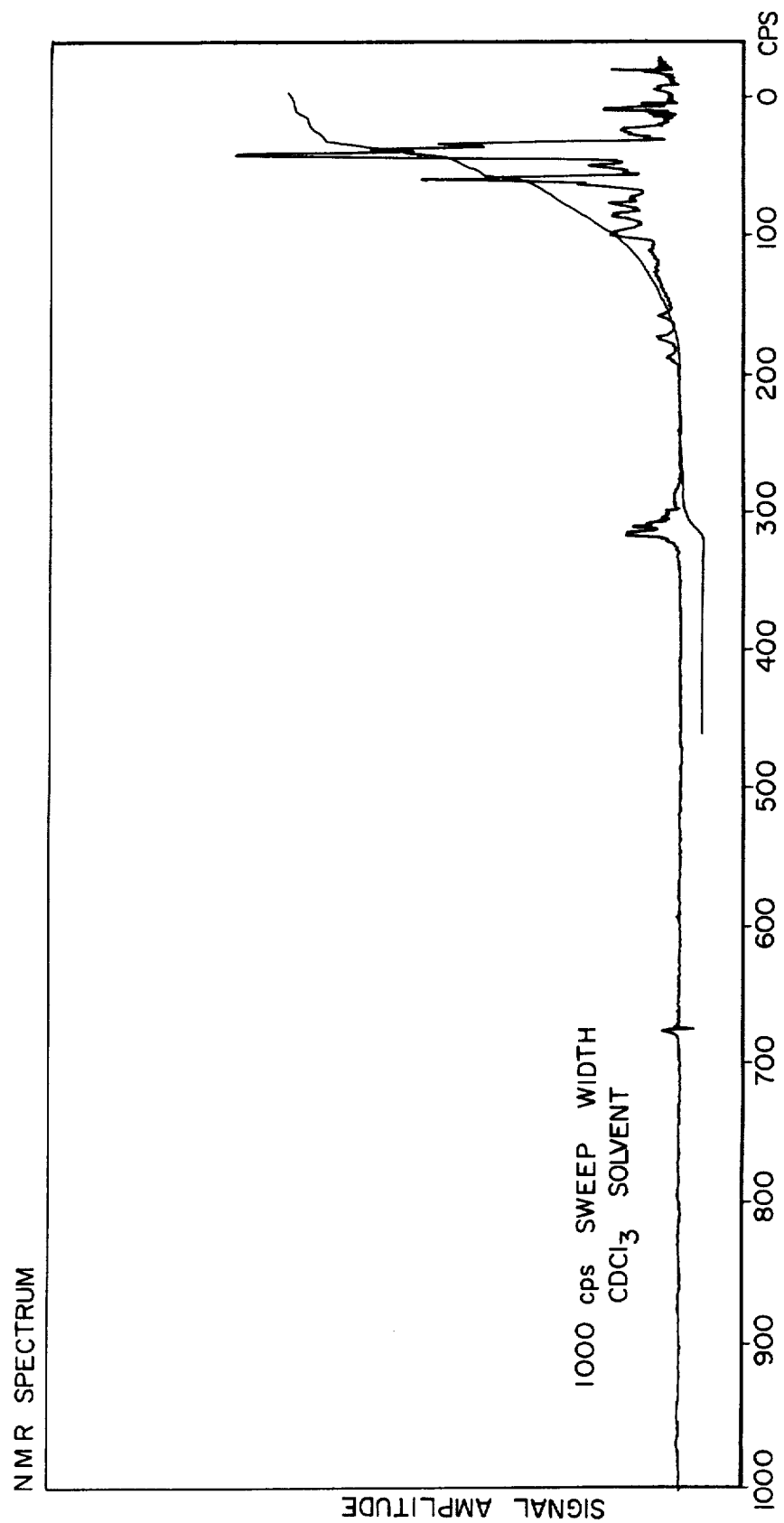
FIG. 19 is the nuclear magnetic resonance spectrum for the product of Example LVIII, 4,8,8,10-tetramethyl-1-oxaspiro[5.5]undecane.
Figure 20:
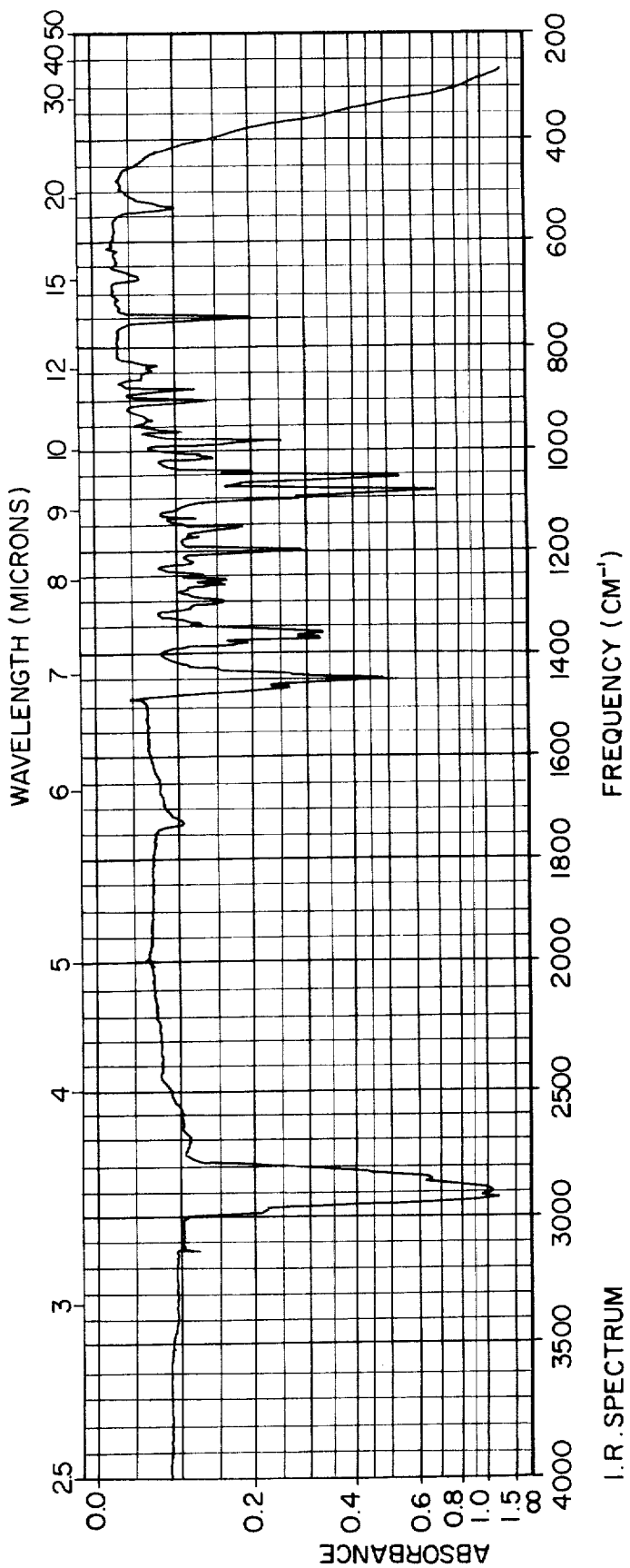
FIG. 20 is the infra-red spectrum for the product of Example LVIII, 4,8,8,10-tetramethyl-1-oxaspiro[5.5]undecane.

The NMR spectrum is set forth in FIG. 19.
The infra-red spectrum is set forth in FIG. 20.
Mass spectral data is as follows: (Molecular Ion, then in decreasing intensity): m/e = 210/139, 69, 153, 83, 55.

From a taste standpoint, this material has a sweet, fruity, berry aroma and a sweet fruity, berry flavor with cherry and green nuances at 5 ppm.

From a perfumery standpoint, this material has a fruity, strawberry, metallic note with underlying valeric notes. As it dries out it becomes more fruity, floral, sweet and "benzyl salicylate-like".

EXAMPLE LIX

PART A

10 Parts by weight of 50 Bloom pigskin gelatin is added to 90 parts by weight of water at a temperature of 150° F. The mixture is agitated until the gelatin completely dissolved and the solution is cooled to 120° F. 20 Parts by weight of the flavor produced according to the procedure of Example LIII is added to the solution which is then homogenized to form an emulsion having a particle size in the range of 2–5 microns. This material is kept at 120° F under which conditions the gelatin will not jell.

Coascervation is induced by adding, slowly and uniformly 40 parts by weight of a 20% aqueous solution of sodium sulphate. During coacervation, the gelatin molecules are deposited uniformly about each oil droplet as a nucleus.

Gelation is effected by pouring the heated coascervate mixture into 1,000 parts by weight of 7% aqueous solution of sodium sulphate at 65° F. The resulting jelled coascervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

PART B

The following mixture is prepared:

| Ingredient | Parts by Weight |
|---|---|
| Liquid flavor composition of Example LIII | 48.4 |
| Propylene glycol | 3 |
| Cab-O-Sil M-5 (Brand of Silica produced by the Cabot Corporation of 125 High Street Boston, Mass. 02110; Physical Properties: Surface Area: 200 m²/gm Nominal Particle Size: 0.012 microns Density: 2.3 lbs./cu.ft.) | 5.2 |

The Cab-O-Sil is dispersed in the liquid flavor composition of Example LIII with vigorous stirring, thereby resulting in viscous liquid. 48.4 Parts by weight of the powder flavor composition of Part A, supra, is then blended into the said viscous liquid, with stirring at 25° C for a period of 50 minutes resulting in a thixotropic sustained release flavor paste.

EXAMPLE LX

CHEWING GUM

100 Parts by weight of chicle are mixed with 4 parts by weight of the flavor prepared in accordance with Example LIX. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into length of 3 inches each. On chewing, the chewing gum has a pleasant long lasting raspberry flavor.

EXAMPLE LXI

CHEWABLE VITAMIN TABLETS

The flavor material produced according to the process of Example LIX is added to a Chewable Vitamin Tablet Formulation at a rate of 10.0 gm/kilogram which Chewable Vitamin Tablet Formulation is prepared as follows:

In a Hobart Mixer, the following materials are blended to homogeneity:

|  | Gms/1000 tablets |
|---|---|
| Vitamin C (ascorbic acid) as ascorbic acid-sodium ascorbate mixture 1:1 | 70.0 |
| Vitamin $B_1$ (thiamine mononitrate) as Rocoat thiamine mononitrate 33⅓% (Hoffman La Roche) | 4.0 |
| Vitamin $B_2$ (riboflavin) as Rocoat riboflavin 33⅓% | 5.0 |
| Vitamin $B_6$ (pyridoxine hydrochloride) as Rocoat pyridoxine hydrochloride 33⅓% | 4.0 |
| Niacinamide as Rocoat niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% Roche | 6.6 |
| d-Biotin | 0.044 |
| Certified lake color | 5.0 |
| Flavor of Example LIX | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 g dry Vitamin A Acetate and 0.6 g Vitamin D are then added as beadlets. The entire blend is then compressed using concave punches at 0.5 g each.

Chewing of the resultant tablets yields a pleasant, longlasting, consistently strong raspberry flavor for a period of 12 minutes.

EXAMPLE LXII

TOOTHPASTE FORMULATION

The following separate groups of ingredients are prepared:

| Parts by Weight | Ingredient |
|---|---|
| Group "A" | |
| 30.200 | Glycerin |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example LIX |
| 100.00 (Total) | |

PROCEDURE:
1. The ingredients in Group "A" are stirred and heated in a steam jacketed kettle to 160° F.
2. Stirring is continued for an additional three to five minutes to form a homogenous gel.
3. The powders of Group "B" are added to the gel, while mixing until a homogenous paste is formed.
4. With stirring, the flavor of "D" is added and lastly the sodium n-lauroyl sarcosinate.
5. The resultant slurry is then blended for one hour. The completed paste is then transferred to a three roller mill and then homogenized, and finally tubed.

The resulting toothpaste when used in a normal toothbrushing procedure yields a pleasant raspberry flavor, of constant strong intensity throughout said procedure (1–1.5 minutes).

EXAMPLE LXIII

PART A

20 Grams of 4-methyl-1-oxaspiro[5.5]undecane prepared according Example II is emulsified in a solution containing 300 gm gum acacia and 700 gm water. The emulsion is spraydried with a Bowen Lab Model Drier utilizing 250 c.f.m. of air with an inlet temperature of 500° F., an outlet temperature of 200° F., and a wheel speed of 50.0000 r.p.m.

PART B

The following mixture is prepared:

| Ingredient | Parts by Weight |
|---|---|
| 4-methyl-1-oxaspiro[5.5]undecane prepared according to Example II | 20 |
| Propylene glycol | 1 |
| Cab-O-Sil M-5 (Brand of Silica produced by the Cabot Corporation of 125 High Street, Boston, Mass. 02110; Physical Properties: Surface Area: 200 m²/gm Nominal Particle Size: 0.012 microns Density: 2.3 lbs./cu.ft.) | 3 |
| Ethyl cellulose | 3 |

The Cab-O-Sil and ethyl cellulose are dispersed in the 4-methyl-1-oxaspiro[5.5]undecane with vigorous stirring, thereby resulting in a viscous liquid. 65 Parts by weight of the powder flavor composition of Part A, supra, is then blended into the said viscous liquid, with stirring at 25° C for a period fo 30 minutes resulting in a dry, free flowing sustained release flavor powder.

EXAMPLE LXIV

CHEWING TOBACCO

Onto 100 pounds of tobacco for chewing (85% Wisconsin leaf and 15% Pennsylvania leaf) the following casing is sprayed at a rate of 30%.

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Flavor Material of Example LXII | 0.4 |

The resultant product is redried to a moisture content of 20%. On chewing, this tobacco has an excellent substantially consistent, long-lasting minty, cooling (20 minutes) nuance in conjunction with the main fruity tobacco note.

What we claim is:

1. A process for augmenting or enhancing the aroma or taste of a foodstuff comprising the step of adding to said foodstuff from 0.5 ppm up to about 0.1 percent by weight of said foodstuff of the spiropyran compound, 4-methyl-1- oxaspiro[5.5]undecane.

2. A flavor modifying composition consisting essentially of (i) from about 0.001 percent up to about 10 percent by weight based on the total weight of flavoring composition of the spiropyran compound, 4-methyl-1-oxaspiro [5.5] undecane and (ii) the remainder of said composition being a food flavor adjuvant selected from the group consisting of parahydroxy-benzyl acetone, vanillin, maltol, alpha-ionone, beta-ionone, isobutyl acetate, ethyl butyrate, dimethyl sulfide, acetic acid and acetaldehyde.

* * * * *